United States Patent
Israel et al.

(10) Patent No.: US 7,678,885 B2
(45) Date of Patent: Mar. 16, 2010

(54) RECOMBINANT BONE MORPHOGENETIC PROTEIN HETERODIMERS, COMPOSITIONS AND METHODS OF USE

(75) Inventors: David Israel, Concord, MA (US); Neil M. Wolfman, Dover, MA (US)

(73) Assignee: Genetics Institute, LLC, Cambridge, MA (US)

(*) Notice: Subject to any disclaimer, the term of this patent is extended or adjusted under 35 U.S.C. 154(b) by 1639 days.

(21) Appl. No.: 10/375,150

(22) Filed: Feb. 28, 2003

(65) Prior Publication Data

US 2003/0235888 A1 Dec. 25, 2003

Related U.S. Application Data

(60) Division of application No. 09/780,601, filed on Feb. 9, 2001, now Pat. No. 6,593,109, which is a division of application No. 08/469,411, filed on Jun. 6, 1995, now Pat. No. 6,190,880, which is a continuation of application No. 07/989,847, filed on Nov. 27, 1992, now Pat. No. 5,866,364, which is a continuation-in-part of application No. 07/864,692, filed on Apr. 7, 1992, now abandoned, which is a continuation-in-part of application No. 07/787,496, filed on Nov. 4, 1991, now abandoned.

(51) Int. Cl.
- C07K 14/00 (2006.01)
- C12N 15/00 (2006.01)
- C12N 1/20 (2006.01)
- C12P 21/00 (2006.01)

(52) U.S. Cl. .................. 530/350; 530/402; 435/69.1; 435/325; 435/70.1

(58) Field of Classification Search .................. None
See application file for complete search history.

(56) References Cited

U.S. PATENT DOCUMENTS

| | | |
|---|---|---|
| 2,465,357 A | 3/1949 | Correll et al. |
| 3,955,719 A | 5/1976 | Pheulpin |
| 4,191,747 A | 3/1980 | Scheicher |
| 4,294,753 A | 10/1981 | Urist |
| 4,394,370 A | 7/1983 | Jeffries |
| 4,399,216 A | 8/1983 | Axel et al. |
| 4,419,446 A | 12/1983 | Howley et al. |
| 4,434,094 A | 2/1984 | Seyedin et al. |
| 4,441,915 A | 4/1984 | Arndt et al. |
| 4,455,256 A | 6/1984 | Urist |
| 4,468,464 A | 8/1984 | Cohen et al. |
| 4,472,840 A | 9/1984 | Jefferies |
| 4,553,542 A | 11/1985 | Schenk et al. |
| 4,563,350 A | 1/1986 | Nathan et al. |
| 4,596,574 A | 6/1986 | Urist |
| 4,608,199 A | 8/1986 | Caplan et al. |
| 4,619,989 A | 10/1986 | Urist |
| 4,627,982 A | 12/1986 | Seyedin et al. |
| 4,642,120 A | 2/1987 | Nevo et al. |
| 4,662,884 A | 5/1987 | Stenaas |
| 4,681,763 A | 7/1987 | Nathanson |
| 4,703,008 A | 10/1987 | Lin |
| 4,727,028 A | 2/1988 | Santerre et al. |
| 4,737,578 A | 4/1988 | Evans |
| 4,758,233 A | 7/1988 | Phillips et al. |
| 4,761,471 A | 8/1988 | Urist |
| 4,766,067 A | 8/1988 | Biswas et al. |
| 4,767,628 A | 8/1988 | Hutchinson |
| 4,769,328 A | 9/1988 | Murray et al. |
| 4,774,228 A | 9/1988 | Seyedin et al. |
| 4,774,322 A | 9/1988 | Seyedin et al. |
| 4,784,055 A | 11/1988 | Langen et al. |
| 4,789,732 A | 12/1988 | Urist |
| 4,795,804 A | 1/1989 | Urist |
| 4,798,885 A | 1/1989 | Mason |
| 4,804,744 A | 2/1989 | Sen |
| 4,810,691 A | 3/1989 | Seyedin |
| 4,828,990 A | 5/1989 | Higashi |
| 4,843,063 A | 6/1989 | Seyedin |
| 4,851,521 A | 7/1989 | Della Valle et al. |
| 4,868,161 A | 9/1989 | Roberts |
| 4,877,864 A | 10/1989 | Wang et al. |
| 4,886,747 A | 12/1989 | Derynck |
| 4,908,204 A | 3/1990 | Robinson et al. |
| 4,920,962 A | 5/1990 | Proulx |
| 4,923,805 A | 5/1990 | Reddy et al. |
| 4,955,892 A | 9/1990 | Daniloff et al. |
| 4,963,146 A | 10/1990 | Li |

(Continued)

FOREIGN PATENT DOCUMENTS

EP 0 052 510 5/1982

(Continued)

OTHER PUBLICATIONS

Zhao et al. Development 125: 1103-1112, 1998.*

(Continued)

*Primary Examiner*—Jeffrey Stucker
*Assistant Examiner*—Aditi Dutt
(74) *Attorney, Agent, or Firm*—Finnegan, Henderson, Farabow, Garrett & Dunner LLP

(57) ABSTRACT

The present invention relates to a methods for producing recombinant heterodimeric BMP proteins useful in the field of treating bone defects, healing bone injury and in wound healing in general. The invention also relates to the recombinant heterodimers and compositions containing them.

2 Claims, 26 Drawing Sheets

U.S. PATENT DOCUMENTS

| | | | |
|---|---|---|---|
| 4,968,590 A | 11/1990 | Kuberasampath et al. |
| 4,992,274 A | 2/1991 | Robinson et al. |
| 5,011,486 A | 4/1991 | Aebischer et al. |
| 5,011,691 A | 4/1991 | Oppermann |
| 5,013,649 A | 5/1991 | Wang et al. |
| 5,019,087 A | 5/1991 | Nichols |
| 5,024,841 A | 6/1991 | Chu et al. |
| 5,026,381 A | 6/1991 | Li |
| 5,041,538 A | 8/1991 | Ling et al. |
| 5,071,834 A | 12/1991 | Burton et al. |
| 5,089,396 A | 2/1992 | Mason et al. |
| 5,102,807 A | 4/1992 | Burger et al. |
| 5,106,626 A | 4/1992 | Parsons et al. |
| 5,106,748 A | 4/1992 | Wozney et al. |
| 5,108,753 A | 4/1992 | Kuberasampath |
| 5,108,922 A | 4/1992 | Wang et al. |
| 5,116,738 A | 5/1992 | Wang et al. |
| 5,118,667 A | 6/1992 | Adams et al. |
| 5,124,316 A | 6/1992 | Antoniades et al. |
| 5,141,905 A | 8/1992 | Rosen et al. |
| 5,147,399 A | 9/1992 | Dellon et al. |
| 5,166,058 A | 11/1992 | Wang et al. |
| 5,166,190 A | 11/1992 | Mather et al. |
| 5,166,322 A | 11/1992 | Shaw et al. |
| 5,168,050 A | 12/1992 | Hammonds |
| 5,171,579 A | 12/1992 | Ron et al. |
| 5,187,076 A | 2/1993 | Wozney et al. |
| 5,187,263 A | 2/1993 | Murray et al. |
| 5,202,120 A | 4/1993 | Silver et al. |
| 5,206,028 A | 4/1993 | Li |
| 5,208,219 A | 5/1993 | Ogawa et al. |
| 5,215,893 A | 6/1993 | Mason et al. |
| 5,216,126 A | 6/1993 | Cox et al. |
| 5,217,867 A | 6/1993 | Evans et al. |
| 5,218,090 A | 6/1993 | Connors |
| 5,229,495 A | 7/1993 | Ichijo et al. |
| 5,256,418 A | 10/1993 | Kemp et al. |
| 5,258,494 A | 11/1993 | Oppermann et al. |
| 5,266,683 A * | 11/1993 | Oppermann et al. ........ 530/326 |
| 5,278,145 A | 1/1994 | Keller et al. |
| 5,284,756 A | 2/1994 | Grinna et al. |
| 5,286,654 A | 2/1994 | Cox et al. |
| 5,290,271 A | 3/1994 | Jernberg |
| 5,292,802 A | 3/1994 | Rhee et al. |
| 5,306,307 A | 4/1994 | Senter et al. |
| 5,308,889 A | 5/1994 | Rhee et al. |
| 5,324,519 A | 6/1994 | Dunn et al. |
| 5,324,775 A | 6/1994 | Rhee et al. |
| 5,328,955 A | 7/1994 | Rhee et al. |
| 5,352,715 A | 10/1994 | McMullin et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,875 A | 11/1994 | Wozney et al. |
| 5,399,346 A | 3/1995 | Anderson et al. |
| 5,399,677 A | 3/1995 | Wolfman et al. |
| 5,405,390 A | 4/1995 | O'Leary et al. |
| 5,411,941 A | 5/1995 | Grinna et al. |
| 5,413,989 A | 5/1995 | Ogawa et al. |
| 5,420,243 A | 5/1995 | Ogawa et al. |
| 5,422,340 A | 6/1995 | Ammann et al. |
| 5,447,725 A | 9/1995 | Damani et al. |
| 5,455,041 A | 10/1995 | Genco et al. |
| 5,455,329 A | 10/1995 | Wingender |
| 5,457,047 A | 10/1995 | Wingender |
| 5,457,092 A | 10/1995 | Schulter |
| 5,459,047 A | 10/1995 | Wozney et al. |
| 5,464,440 A | 11/1995 | Johannsson |
| 5,508,263 A | 4/1996 | Grinna et al. |
| 5,516,654 A | 5/1996 | Israel |
| 5,520,923 A | 5/1996 | Tjia et al. |
| 5,538,892 A | 7/1996 | Donahoe et al. |
| 5,543,394 A | 8/1996 | Wozney et al. |
| 5,545,616 A | 8/1996 | Woddruff |
| 5,547,854 A | 8/1996 | Donahoe et al. |
| 5,556,767 A | 9/1996 | Rosen et al. |
| 5,618,924 A | 4/1997 | Wang et al. |
| 5,631,142 A | 5/1997 | Wang et al. |
| 5,635,372 A | 6/1997 | Celeste et al. |
| 5,635,373 A | 6/1997 | Wozney et al. |
| 5,637,480 A | 6/1997 | Celeste et al. |
| 5,639,638 A | 6/1997 | Wozney et al. |
| 5,645,592 A | 7/1997 | Nicolais et al. |
| 5,648,467 A | 7/1997 | Trinchieri et al. |
| 5,650,494 A | 7/1997 | Cerletti et al. |
| 5,658,882 A | 8/1997 | Celeste et al. |
| 5,661,007 A | 8/1997 | Wozney et al. |
| 5,674,292 A | 10/1997 | Tucker et al. |
| 5,688,678 A | 11/1997 | Hewick et al. |
| 5,693,779 A | 12/1997 | Moos, Jr. et al. |
| 5,700,664 A | 12/1997 | Yang |
| 5,700,774 A | 12/1997 | Hattersley et al. |
| 5,700,911 A | 12/1997 | Wozney et al. |
| 5,703,043 A | 12/1997 | Celeste et al. |
| 5,728,679 A | 3/1998 | Celeste et al. |
| 5,750,651 A | 5/1998 | Oppermann et al. |
| 5,752,974 A | 5/1998 | Rhee et al. |
| 5,756,457 A | 5/1998 | Wang et al. |
| 5,786,217 A | 7/1998 | Tubo et al. |
| 5,813,411 A | 9/1998 | Van Bladel et al. |
| 5,827,733 A | 10/1998 | Lee et al. |
| 5,846,931 A | 12/1998 | Hattersley et al. |
| 5,849,880 A | 12/1998 | Wozney et al. |
| 5,866,364 A | 2/1999 | Israel et al. |
| 5,932,216 A | 8/1999 | Celeste et al. |
| 5,935,594 A | 8/1999 | Ringeisen et al. |
| 5,936,067 A | 8/1999 | Graham et al. |
| 5,939,323 A | 8/1999 | Valentini et al. |
| 5,939,388 A | 8/1999 | Rosen et al. |
| 5,965,403 A | 10/1999 | Celeste et al. |
| 5,972,368 A | 10/1999 | McKay |
| 5,986,058 A | 11/1999 | Lee et al. |
| 6,001,352 A | 12/1999 | Boyan et al. |
| 6,004,937 A | 12/1999 | Wood et al. |
| 6,027,919 A | 2/2000 | Celeste et al. |
| 6,034,061 A | 3/2000 | Rosen et al. |
| 6,034,062 A | 3/2000 | Thies et al. |
| 6,071,708 A * | 6/2000 | Jones et al. .................. 435/7.1 |
| 6,132,214 A | 10/2000 | Sohonen et al. |
| 6,150,328 A | 11/2000 | Wang et al. |
| 6,177,406 B1 | 1/2001 | Wang et al. |
| 6,187,742 B1 | 2/2001 | Wozney et al. |
| 6,190,880 B1 | 2/2001 | Israel et al. |
| 6,207,813 B1 | 3/2001 | Wozney et al. |
| 6,245,889 B1 | 6/2001 | Wang et al. |
| 6,284,872 B1 | 9/2001 | Celeste et al. |
| 6,287,816 B1 | 9/2001 | Rosen et al. |
| 6,291,206 B1 | 9/2001 | Wozney et al. |
| 6,331,612 B1 | 12/2001 | Celeste et al. |
| 6,340,668 B1 | 1/2002 | Celeste et al. |
| 6,432,919 B1 | 8/2002 | Wang et al. |
| 6,437,111 B1 | 8/2002 | Wozney et al. |
| 6,558,925 B2 | 5/2003 | Graham et al. |
| 6,586,388 B2 | 7/2003 | Oppermann et al. |
| 6,593,109 B1 | 7/2003 | Israel et al. |
| 6,610,513 B2 | 8/2003 | Wozney et al. |
| 6,613,744 B2 | 9/2003 | Wozney et al. |
| 6,623,934 B2 | 9/2003 | Celeste et al. |
| 6,699,471 B2 | 3/2004 | Radice et al. |
| 6,719,968 B2 | 4/2004 | Celeste et al. |

FOREIGN PATENT DOCUMENTS

| | | |
|---|---|---|
| EP | 0 058 481 | 8/1982 |
| EP | 0 121 976 | 10/1984 |
| EP | 0 128 041 | 12/1984 |
| EP | 0 148 155 | 7/1985 |
| EP | 0 155476 | 9/1985 |
| EP | 0 169 016 | 1/1986 |
| EP | 0 177 343 | 4/1986 |
| EP | 0 212 474 | 3/1987 |
| EP | 0 222 491 | 5/1987 |
| EP | 0 241 809 | 10/1987 |
| EP | 0 313 578 | 5/1989 |
| EP | 0 329 239 | 8/1989 |
| EP | 0 336 760 | 10/1989 |
| EP | 0 401 055 | 12/1990 |
| EP | 0 409 472 | 1/1991 |
| EP | 0 416 578 | 3/1991 |
| EP | 0 429 570 | 6/1991 |
| EP | 0 433 225 | 6/1991 |
| EP | 0 512 844 | 11/1992 |
| EP | 0 530 804 | 3/1993 |
| EP | 0 531 448 | 3/1993 |
| EP | 0 536 186 | 4/1993 |
| EP | 0 592 562 | 4/1994 |
| EP | 0 626 451 | 11/1994 |
| EP | 0 688 869 | 12/1995 |
| EP | 0 741 187 | 11/1996 |
| EP | 0 831 884 | 4/1998 |
| JP | 63-181770 A | 7/1988 |
| JP | 05-123390 A2 | 5/1993 |
| JP | 03-345189 | 7/1993 |
| JP | 05-277174 A2 | 10/1993 |
| WO | WO 84/01106 | 3/1984 |
| WO | WO 85/04173 | 9/1985 |
| WO | WO 86/00525 | 1/1986 |
| WO | WO 86/00639 | 1/1986 |
| WO | WO 87/00528 | 1/1987 |
| WO | WO 88/00205 | 1/1988 |
| WO | WO 89/09787 | 10/1989 |
| WO | WO 89/09788 | 10/1989 |
| WO | WO 89/10133 | 11/1989 |
| WO | WO 89/10409 | 11/1989 |
| WO | WO 90/03733 | 4/1990 |
| WO | WO 90/11366 | 10/1990 |
| WO | WO 91/02744 | 3/1991 |
| WO | WO 91/04274 | 4/1991 |
| WO | WO 91/05802 | 5/1991 |
| WO | WO 91/10444 | 7/1991 |
| WO | WO 91/17777 | 11/1991 |
| WO | WO 91/18047 | 11/1991 |
| WO | WO 91/18098 | 11/1991 |
| WO | WO 92/05198 | 4/1992 |
| WO | WO 92/05199 | 4/1992 |
| WO | WO 92/07004 | 4/1992 |
| WO | WO 92/07073 | 4/1992 |
| WO | WO 92/09697 | 6/1992 |
| WO | WO 92/14481 | 9/1992 |
| WO | WO 92/15323 | 9/1992 |
| WO | WO 92/20793 | 11/1992 |
| WO | WO 92/22319 | 12/1992 |
| WO | WO 93/00049 | 1/1993 |
| WO | WO 93/00050 | 1/1993 |
| WO | WO 93/00432 | 1/1993 |
| WO | WO 93/04692 | 3/1993 |
| WO | WO 93/05751 | 4/1993 |
| WO | WO 93/06872 | 4/1993 |
| WO | WO 93/09228 | 5/1993 |
| WO | WO 93/09229 | 5/1993 |
| WO | WO 93/09802 | 5/1993 |
| WO | WO 93/13206 | 7/1993 |
| WO | WO 93/16099 | 8/1993 |
| WO | WO 93/19177 | 9/1993 |
| WO | WO 93/20858 | 10/1993 |
| WO | WO 94/01557 | 1/1994 |
| WO | WO 94/03200 | 2/1994 |
| WO | WO 94/06449 | 3/1994 |
| WO | WO 94/11502 | 5/1994 |
| WO | WO 94/15949 | 7/1994 |
| WO | WO 94/15965 | 7/1994 |
| WO | WO 94/15966 | 7/1994 |
| WO | WO 94/21681 | 9/1994 |
| WO | WO 94/24285 | 10/1994 |
| WO | WO 94/26892 | 11/1994 |
| WO | WO 94/26893 | 11/1994 |
| WO | WO 95/01801 | 1/1995 |
| WO | WO 95/01802 | 1/1995 |
| WO | WO 95/05846 | 3/1995 |
| WO | WO 95/07982 | 3/1995 |
| WO | WO 95/10539 | 4/1995 |
| WO | WO 95/10611 | 4/1995 |
| WO | WO 95/12664 | 5/1995 |
| WO | WO 95/15966 | 6/1995 |
| WO | WO 95/16035 | 6/1995 |
| WO | WO 95/33830 | 12/1995 |
| WO | WO 96/01845 | 1/1996 |
| WO | WO 96/02559 | 2/1996 |
| WO | WO 96/36710 | 11/1996 |
| WO | WO 96/38570 | 12/1996 |
| WO | WO 96/39170 | 12/1996 |
| WO | WO 96/39203 | 12/1996 |
| WO | WO 96/40883 | 12/1996 |
| WO | WO 97/15321 | 5/1997 |
| WO | WO 97/22308 | 6/1997 |
| WO | WO 97/34626 | 9/1997 |
| WO | WO 97/40137 | 10/1997 |
| WO | WO 97/45532 | 12/1997 |
| WO | WO 97/48275 | 12/1997 |
| WO | WO 97/49412 | 12/1997 |
| WO | WO 98/16641 | 4/1998 |
| WO | WO 98/31788 | 7/1998 |
| WO | WO 98/34951 | 8/1998 |
| WO | WO 98/40113 | 9/1998 |
| WO | WO 98/49296 | 11/1998 |
| WO | WO 99/01159 | 1/1999 |
| WO | WO 99/24070 | 5/1999 |
| WO | WO 99/31120 | 6/1999 |
| WO | WO 99/37320 | 7/1999 |
| WO | WO 99/38543 | 8/1999 |
| WO | WO 99/45949 | 9/1999 |
| WO | WO 00/37124 | 6/2000 |
| WO | WO 00/43781 A | 7/2000 |

OTHER PUBLICATIONS

Takada et al. Jour Biol Chem 278: 43229-43235, 2003.*
Wells et al. Biochemistry 29: 8509-8517, 1990.*
Ngo et al. the Protein Folding Problem and Tertiary Structure Prediction, 492-495, 1994.*
Bork et al. Genome Res 10: 398-400, 2000.*
Skolnick et al. Trends in Biotech 18: 34-39, 2000.*
Doerks et al. Trends in Genetics 14: 248-250, 1998.*
Smith et al. Nature Biotechnology 15: 1222-1223, 1997.*
Brenner SE. Trends in Genetics 15: 132-133, 1999.*
Bork et al. Trends in Genetics 12: 425-427, 1996.*
Chakrabarti et al. Gene 77: 87-93, 1989.*
Aiba et al., *Blood*, 90:3923-3930 (1997).
Alberts et al., *Molecular Biology of the Cell, Third Ed., Garland Publishing, Inc.*, New York, NY, pp. 1142 (1994).
Amizuka et al., *J. Cell Biol.*, 126:1611-1623 (1994).
Attisano et al., *Cell*, 68:97-108 (1992).
Baird et al., *Biochem. Biophys. Res. Comm.*, 138:476-482 (1986).
Barres. B.A. et al., *Development*, 118:283-295 (1993).
Basler, K. et al., *Cell*, 73:687-702 (1993).
Beck et al., *Growth Factors*, 2:273-282 (1990).
Belo et al., *Mech. Devel.*, 68:45-57 (1997).

Bendig, *Genetic Engineering*, 7:91-127 (1988).
Biben et al., *Develop. Biol.*, 194:135-151 (1998).
Bignami et al., *Brain Res.*, 43:429-435 (1972).
Bignami, A. et al., *Plasticity and Regeneration of the Nervous System*, 197-206 (1991).
Bolton et al., *Biochem J.*, 133:529 (1973).
Border et al., *J. Clin. Invest.*, 90:1-7 (1992).
Bouwmeester et al., *Nature*, 382:595-601 (1996).
Bowen-Pope et al., *J. Biol. Chem.*, 257:5161 (1982).
Bowie et al., *Science*, 247:1306-1310 (1990).
Brown et al., *J. Immunol.*, 142:679 (1989).
Broxmeyer et al., *PNAS*, 85:9052 (1988).
Bruder et al., *J. Cell Biochem.*, 56:283-294 (1994).
Burt, D.W., *BBRC*, 184:590-595 (1992).
Campoccia et al., *Biomaterials*, 19:2101-27 (1998).
Caplan, A., *Bone Repair and Regeneration*, 21:429-435 (1994).
Celeste et al., *J. Bone Mineral Res.*, 9:suppl. 5136 (1994).
Celeste et al., *PNAS*, 87:9843-9847 (1990).
Chang et al., *J. Biol. Chem.*, 269:28227-28234 (1994).
Conlon et al., *Development*, 120:1919 (1994).
Conlon et al., *Development*, 111:969 (1991).
Collignon et al., *Nature*, 381:155 (1996).
Creighton, T.E., *Proteins: Structure and Molecular Principles*, W.H. Freeman and Co., New York (1983).
Cunningham et al., *PNAS*, 89:11740-11744 (1992).
Dagert et al., *Gene*, 6:23 (1979).
Dale et al., *EMBO J.*, 12:4471 (1993).
D'Alessandro et al., *Growth Factors*, 11:53-69 (1994).
D'Allesandro et al., *J. Bone Mineral Res.*, (6) Suppl: 1:S153 (1991).
DeWulf et al., *Endocrinology*, 136:2652-2663 (1995).
Dexter et al., *Nature*, 344:380 (1990).
DiLeone et al., *Genetics*, 148:401-408 (1998).
Doctor et al., *Dev. Biol.*, 151:591-605 (1992).
Ducy et al., *Kidney Intl.*, 57:2207-2214 (2000).
Dunn et al., *Cancer Cells*, 3:227-234 (1985).
Ebner et al., *Science*, 260:1344-1348 (1993).
Estevez et al., *Nature*, 365:644-649 (1993).
Eto et al., *Biochem. Biophys. Res. Comm.*, 142:1095 (1987).
Fainsod et al., *Mech. Dev.*, 1:39-50 (1997).
Fallon et al., *J. Cell Biol.*, 100:198-207 (1985).
Fenton et al., *Endocrinology*, 129:1762-1768 (1991).
Finch et al., *PNAS*, 94:6770-6775 (1997).
Frishchauf et al., *J. Mol. Biol.*, 170:827-842 (1983).
Frommel et al., *J. Mol. Evol.*, 24:233-257 (1985).
Gamer et al., *Develop. Biol.*, 208:222-232 (1999).
Geisert et al., *Develop. Biol.*, 143:335-345 (1991).
Gerhart et al., *Trans. Othop. Res. Soc.*, 16:172 (1991).
Gething et al., *Nature*, 293:620-625 (1981).
Gitelman et al., *J. Cell. Biol.*, 126:1595-1609 (1994).
Goodman, R., *Methods for Serum-Free Culture of Neuronal and Lymphoid Cells*, 23-36 (1984).
Gough et al., *EMBO J.*, 4:645-653 (1985).
Graham et al., *EMBO*, 15:6505-6515 (1996).
Graham et al., *Growth Factors*, 7:151-160 (1992).
Graham et al., *J. Biol. Chem.*, 269:4974-4978 (1994).
Graham et al., *Nature*, 344:442 (1990).
Guigon et al., *Chem. Abstracts*, 96:36, Abstract No. 115633h (1982).
Guigon et al., *Cancer Res.*, 42:638 (1982).
Hammonds et al., *Mol. Endocrin.*, 149-155, vol. 4, (1990).
Harrison et al., *Exp. Cell Res.*, :340-345 (1991), vol. 192.
Hasimoto et al., *J. Biol. Chem.*, 267:7203-7206 (1992).
He et al., *Develop. Dynamics*, 196:133-142 (1993).
Hebda et al., *J. Invest. Dermatol.*, 91:440-445 (1988).
Hefti et al., *J. Neurobiol.*, 25:1418-1435 (1994).
Hemmati-Brinvanlou et al., *Nature*, 359:609-614 (1992).
Hoang et al., *J. Biol. Chem.*, 271:26131-26137 (1996).
Hollnagel et al., *Calcified Tissue Int'l*, 56:430 (1995).
Hunkapiller et al., *Meth. Enzymol.*, 91:399-413 (1983).
Inouye et al., *Mol. Cell. Endocrinol.*, 90:1 (1992).
Iwasaki, *J. Biol. Chem.*, 271:17360-5 (1996).
Janowska-Wieczorek et al., *Biol. Abstracts, Reviews-Reports-Meetings*, 33:61402 (1987).
Jonhagen et al., *Dement. Cogn. Disord.*, 9:246-257 (1998).

Joyce et al, *J. Cell Biochem.*, Suppl.17E:136, Abstract R504 (1993).
Kalyani et al., *J. Neuroscience*, 18:7856-7869 (1998).
Karaplis et al., *Mol. Endocrin.*, 4:441-446 (1990).
Karaplis et al., *Genes & Development*, 8:277-289 (1994).
Katagiri et al., *J. Cell Biol.*, 127:1755-1766 (1994).
Kaufman et al., *Mol. Cell Biol.*, 2:1304-1319 (1982).
Kaufman et al., *Mol. Cell Biol.*, 5:1750-1759 (1985).
Kaufman et al., *J. Mol. Biol.*, 159:601-629 (1982).
Kaufman et al., *PNAS*, 82:689-693 (1985).
Kingsley et al., *Cell*, 71:399-410 (1992).
Kingsley et al., *Genes & Development*, 8:133-146 (1994).
Klein-Nulend et al., *Tissue Engineering*, 4:305-313 (1998).
Klein et al., *Brain Res.* 875:144-151 (2000).
Kliot et al., *Exper. Neur.*, 109:57-69 (1990).
Koenig et al., *Mol. Cell Biol.*, 14:5961-5974 (1994).
Koopman et al., *JBC*, 273:33267-33272, (1998).
Krueger, G.G., , *N. E. J. Med.*, 328:1845-1846 (1993).
LaPan et al., Program and Abstract, 13th Ann. Mtg of the AM Society of Bone and Min. Res., Aug. 24-28, p. 5153, Abstract No. 280, Mary Ann Liebert, Inc. NY (1991).
Lathe, J., *J. Mol. Biol.*, 183:1-12 (1985).
Lawn et al., *Cell*, 15:1157-1174 (1978).
Lefer et al., *PNAS*, 90:1018-22 (1993.
LeMaire et al., *Trends in Genetics*, 12:525-531 (1996).
Leslie M., *Nurse Practitioner*, 24:38, 41-8 (1999).
Lewin, *Science*, 237:1570 (1987).
Leyns et al., *Cell*, 88:747-756 (1997).
Lin et al., *Cell*, 68:775-785 (1992).
Lin et al., *Science*, 260:1130-1132 (1993).
Lipes et al., *PNAS*, 85:9704 (1988).
Lodish et al., *Mol. Cell Biol.*, 3rd Ed., W.H. Freeman & Co., p266 (1995).
Lopez-Coviella et al., *J. Physiol. Paris.*, 92:460-461 (1998).
Lopez-Coviella et al., *Science*, 289:313-316 (2000).
Lopez-Coviella et al., *Xth International Symposium on Cholinergic Mechanisms* (1998).
Lopez-Coviella et al., *Soc. Neurosci. Abstracts*, 25:517 (1999).
Lord et al., *Brit. J. Haematol.*, 34:441 (1976).
Lorimore et al., *Leuk. Res.*, 14:481-489 (1990).
Lowe et al., *Nature*, 381:158 (1996).
Lucas et al., *Differentiation*, 37:47-52 (1988).
Luthman et al., *Nucl. Acids Res.*, 11:1295-1308 (1983).
Luyten et al., *J. Biol. Chem.*, 264:13377-13380 (1989).
Luyten et al., *Exp. Cell. Res.*, 210(2):224-229 (1994).
Lyons et al., *PNAS*, 86:4554-4558 (1989).
Mangin et al., *PNAS*, 85:597-601 (1988).
Mangin et al., Gene, 95:195-202 (1990).
Maniatis et al., *Mol. Cloning, A Laboratory Manual, Cold Spring Harbor Laboratory*, CSH., N.Y.:310-323, 387-389 & 404-433 (1982).
Mantel et al., *PNAS*, 90:2232-2236 (1993).
Mansour et al., J. Neurosci. Res., 25:300-377 (1990).
Marieb, E.N., *In Human Anatomy and Physiology*, 2nd Ed., The Benjamin/Cummings Publishing Co., pp. 373-375 (1992).
Mark, *J. Cell. Biol.*, 130:701-10 (1995).
Marra et al., *EMBL Database*, Accession No. AA120122 (1996).
Martin et al., *Crit. Rev. Biochem. Mol. Biol.*, 26:377-395 (1991).
Mason et al., *Nature*, 318:659-663 (1985).
Massague et al., *Trends in Cell Biol.*, 4:172-178 (1994).
Massague et al., *Cell*, 69:1067-1070 (1992).
Massague et al., *Cell*, 49:437-438 (1987).
Mathews et al., *Cell*, 65:973-982 (1991).
Matsuzaki et al., *J. Biol. Chem.*, 268:12719-12723 (1993).
Matzuk et al., *Nature*, 360:313 (1992).
McConahey et al., *Int. Arch. Allergy*, 29:185-189 (1966).
McDonald et al., *Cell*, 73:421-424 (1993).
Miller et al., *J. Immunol.*, 143:2907 (1989).
Miller et al., *Genetic Engineering*, 8:277-298 (1986).
Miyazono et al., *Gen Bank Record No.* Z23154 (1993).
Morii et al., *J. Biol. Chem.*, 258:12749-12752 (1983).
Mullins et al., *Nature*, 303:856-858 (1984).
Nabeshima et al., *Alz Dis. And Assoc. Disord.* 14(Suppl. 1):S39-S46 (2000).

Nakamura et al., *J. Biol. Chem.*, 267:18924-18928 (1992).
Nakao et al., *Mol. Cell Biol.*, 10:3646-3658 (1990).
Nakatani T., *Jap. J. Clin. Med.*, 52:824-33 (1994).
Nathan et al., *J. Cell Biol.*, 113:981-986 (1991).
Neuhaus et al., *Mech. Dev.*, 80:181-184 (1999).
Nirschl, R., *American Orthopaedic Society for Sports Medicine*, Leadbetter, W. et al., eds, Ch. 13:577-585 (1989).
Ngo et al., *Merz et al., eds., Brickhauser, Boston*, Springer Verlag, pp. 433-434 & 492-495 (1994).
Noble et al., *J. Neuroscience*, 4:1892-1903 (1984).
Obaru et al., *J. Biochem.*, 99:885 (1986).
Ogawa et al., *J. Biol. Chem.*, 267:14233 (1992).
Ohura et al., *J. Biomed. Mat. Res.*, 30:193-200 (1996).
Ohura et al., *J. Biomed. Mat. Res.*, 44: 168-175 (1999).
Okayama et al., *Mol. Cell Biol.*, 2:161-170 (1982).
Ozkaynak et al., *EMBO Journal*, 9:2085-2093 (1990).
Padgett et al., *Nature*, 325:81-84 (1987).
Paralkar, et al., *J. Cell Biol.*, 119:1721-1728 (1992).
Park et al., *J. Biol. Chem.*, 271:8161-9 (1996).
Patel et al., Pharmacotherapy of Cognitive Impairment in Alzheimer's Disease: A Review:81-95 (1992).
Perides et al., *J. Biol. Chem.*, 269:765-770 (1994).
Perides et al., *PNAS*, 89:10326-10330 (1992).
Peyron, J.G. *J. Rheumatol. Suppl.*, 27:2-3 (1991).
Pierce et al., *J. Clin. Investig.*, 96:1336-50 (1995).
Pollock, *J. Biol. Chem.*, 271:8008-14 (1996).
Pragnell et al., *Blood*, 72:196-201 (1988).
2001-2002 Progress Report on Alzheimer's Disease, *National Institute on Aging; NIH*:1-51 (2002).
Rabin et al., *Mol. Cell. Biol.*, 13:2203-2213 (1993).
Ralph et al., *Cancer Res.*, 37:546 (1977).
Ralph et al., *J. Immunol.*, 114:898 (1975).
Rattner et al., *PNAS*, 94:2859-2863 (1997).
Reddi, A. *JBJS*, 83-A:S1-1:S1-S6 (2001).
Reddi et al., *Osteoporosis, Academic Press*, pp. 281-287 (1996).
Reddi et al., *PNAS*, 69:1601 (1972).
Reeck, *Cell*, 50:667 (1987).
Roberts et al., *PNAS*, 83:4167-4171 (1986).
Robertson et al., *Biochem. Biophys. Res. Commun.*, 149:744-749 (1987).
Rodeo et al., *Orthopaedic Res. Soc.*, 41$^{st}$ Annual Mtg, Orlando, Florida, p288 (1995).
Rodeo, et al., *J. Bone Joint Surg.*, 75-A:1795-1803 (1993).
Rosen et al., *Trends in Genetics*, 8:97-102 (1992).
Rosen et al., *Connect Tissue Res.*, 20:313-9 (1989).
Rubin et al., *Science*, 287:2204-2215 (2000).
Rudinger, *Peptide Hormones*, Parsons (ed.), U Park Press, Baltimore: 1-7 (1976).
Sakai et al., *PNAS*, 87:8378-8382 (1990).
Salic et al., *Development*, 124:4739-4748 (1997).
Sambrook et al., *Mol. Cloning: A Laboratory Manual*, 2$^{nd}$ Ed., vols. 1, 2 and 3, Cold Spring Harbor Laboratory Press: Cold Spring Harbor, New York, USA (1989).
Sampath et al., *J. Biol Chem.*, 267:20352-20362 (1992).
Sampath et al., *J. Biol Chem.*, 265:13198-13205 (1990).
Sampath et al., *PNAS*, 84:7109-7113 (1987).
Sampath et al., *PNAS*, 80:6591-6595 (1983).
Sampath et al., *Exp. Cell. Res.*, 143:460-64 (1982).
Sato et al., *Clin. Orthopaedics Related Res.*, 183:180-187 (1984).
Saukkonon et al., *J. Exp. Med.*, 171:439 (1990).
Schubert et al., *Nature*, 344:868-870 (1990).
Schulz et al., *Principles of Protein Structure*, Springer-Verlag New York, Inc., New York:14-16 (1979).
Shah, et al., *J. Cell Sci.*, 108:985-1002 (1995).
Shimasaki et al., *PNAS*, 85:4218-4222 (1988).
Shipley et al., *Cancer Res.*, 46:2068-2071 (1986).
Shoda et al., *Growth Factors*, 8:165-172 (1993).
Smith et al., *Brain Res.*, 543:111-122 (1991).
Smith et al., *Dev. Biol.*, 138:377-390 (1990).
Smith et al., *J. Neurochem.*, 60:1453-1466 (1993).
Sompayrac et al., *PNAS*, 78:7575-7578 (1981).
Song et al., *Mol. Biol. Cell*, 5:384a (1994) and 34$^{th}$ Ann. Mtg of the American Soc. for Cell Biol., San Francisco, CA (1994).
Sporn et al., *Nature*, 332:217-219 (1988).
Sporn et al., *Science*, 233:532-534 (1986).
Storm et al., *Nature*, 368:639-642 (1994).
Sugino et al., *J. Biol. Chem.*, 268:15579 (1993).
Suggs et al., *PNAS*, 78:6613-6617 (1981).
Sumitomo et al., *Biochem. Biophys. Acta.*, 208:1 (1995).
Sumitomo et al., *DNA Sequence-J. DNA Sequence and Mapping* 3:297-302 (1993).
Suzuki et al., *Proc Natl Acad Sci USA* 91:10255-59 (1994).
Tabas et al., *Genomics*, 9:283-289 (1991).
Takagi et al., *Clin. Orthopaed. Related Res.*, 171:224-231 (1982).
Taniguchi et al., *PNAS*, 77:5230-5233 (1980).
Tatusova et al., *FEMS Microbiol. Lett.*, 174:247-250, 1999.
Ten Dijke et al., *J. Biol. Chem.*, 269:16985-16988 (1994).
Ten Dijke et al., *EMBL Z22534* (Apr. 6, 1993).
Ten Dijke et al., *EMBL Sequence Database, European Molecular Biology Laboratory* (Basel, CH), Accession No. Z22535 (1993).
Ten Dijke et al., *EMBL Sequence Database, European Molecular Biology Laboratory* (Basel, CH), Accession No. Z22536 (1993).
Thies et al., *J. Bone Min. Res.*, 5:305 (1990).
Thies et al., *Endocrinol.*, 130:1318-1324 (1992).
Thomsen et al., *Trends in Genetics*, 13:209-211 (1997).
Thomsen et al., *Cell*, 74:433-441 (1993).
Tona et al., *J. Histochem. Cytochem.*, 41:591-599 (1993).
Toriumi et al., *Arch. Otolaryngol. Head Neck Surg.*, 117:1101-1112 (1991).
Tsuchida et al., *PNAS*, 90:11242-11246 (1993).
Tsukazaki et al., *Calcif. Tissue Int.*, 57:196-200 (1995).
Tuszynski, *Cell Transplantation*, 9:629-636 (2000).
Ueno et al., *PNAS*, 84:8282-8286 (1987).
Ulrich et al., *EMBO J.*, 3:361-364 (1984).
Urdal et al., *PNAS*, 81:6481-6485 (1984).
Urist et al., *Fed. Proceed.*, Bethesda, MD, US, :746 (1985), 44.
Urist et al., *PNAS*, 81:371-375 (1984).
Urist et al., *Clin. Orthopaed. and Related Res.*, 187: 277-280 (1984).
Urist et al., *Proc. Soc. Exper. Biol. & Med.*, :194 (1983), 173.
Urist et al., *Science*, 220:680-686 (1983).
Urist et al., *PNAS*, 70:3511 (1973).
Urist et al., *Clin. Orthoped. Rel. Res.*, 214:295-304, (1987).
Urlaub et al., *PNAS*, 77:4216-20 (1980).
Vukicevic et al. *PNAS*, 93:9021-6 (1996).
Wall et al., *J. Cell Biol.*, 120:493-502 (1993).
Wang et al., *Cell*, 67:797-805 (1991).
Wang et al., *J. Cell Biochem.*, Suppl. 15, Part E, p. 161, Abstract Q020 (1991).
Wang et al., *PNAS*, 87:2220-2224 (1990).
Wang et al., *PNAS*, 85:9484-9488 (1988).
Wang, E.A., *Trends in Biotech.*, 11:379-383 (1993).
Wang et al., *Cell*, 88:757-766 (1997).
Wang et al., *Stroke*, 32:2170-2178 (2001).
Weeks et al., *Cell*, 51:861-867 (1987).
Wells, *Biochemistry*, 29:8509-8517 (1990).
Wharton et al., *PNAS*, 88:9214-9218 (1991).
Wolpe et al., *FASEB J.*, 3:2565-2573 (1989).
Wolpe et al., *J. Biochem. Suppl. O*, Abstract H141, 13 Part C:21 (1989).
Wolpe et al., *J. Exp. Med.*, 167:570 (1988).
Wong et al., *Science*, 228:810-815 (1985).
Woo et al., *PNAS*, 75:3688-3691 (1978).
Wood et al., *PNAS*, 82:1585-1588 (1985).
Wozney et al., *J. Cell Sci.*, Suppl. 13:149-156 (1990).
Wozney, *Mol. Reproduction & Develop.*, 32:160-167 (1992).
Wozney et al., *Science*, 242:1528-1534 (1988).
Wozney, J.M., *Prog. Growth Factor Res.*, 1:267-280 (1989).
Wozney et al., *Handbook of Exp. Pharm.*, eds., G.R. Mundy and T.J. Martin; Springer-Verlag, Berlin, Chapter 20, 107:725-748 (1993).
Wozney, *Cell. & Mol. Biol. Bone*, pp. 131-167 (1993) (Academic Press, Inc.).
Wozney et al., *J. Cell Biochem.*, Suppl. 16F:76 Abstract (1992).
Wozney *Spine*, 27:S2-S8 (2002).
Wright et al., *Leukemia Res.*, 4:537 (1980).
Wright et al., *Cell Tissue Kinet.*, 18:193 (1985).
Xu et al., *Proc Natl Acad Sci USA*, 91:7957-61 (1994).

Yamaguchi et al., *Nippon Rinsho*, 50:1932-1938 (1992).
Yamaji et al., *Biochem. Biophys. Res. Comm.*, 205:1944-1951 (1994).
Zipfel et al., *J. Immunol.*, 142:1582 (1989).

Zheng et al., *Path. Res. Pract.*, 188:1104-1121 (1992).
Zhou et al., *Nature*, 361:543-547 (1993).

\* cited by examiner

```
         10         20         30         40         50         60         70
GTCGACTCTA GAGTGTGTGT CAGCACTTGG CTGGGGACTT CTTGAACTTG CAGGGAGAAT AACTTGCGCA 80         90        100        110        120        130        140
CCCCACTTTG CGCCGGTGCC TTTGCCCCAG CGGAGCCTGC TTCGCCATCT CCGAGCCCCA CCGCCCCTCC 150        160        170        180        190        200        210
ACTCCTCGGC CTTGCCCGAC ACTGAGACGC TGTTCCCAGC GTGAAAAGAG AGACTGCGCG GCCGGCACCC 220        230        240        250        260        270        280
GGGAGAAGGA GGAGGCAAAG AAAAGGAACG GACATTCGGT CCTTGCGCCA GGTCCTTTGA CCAGAGTTTT 290        300        310        320        330        340        350
TCCATGTGGA CGCTCTTTCA ATGGACGTGT CCCCGCGTGC TTCTTAGACG GACTGCGGTC TCCTAAAGGT
```

```
   (1)             370             385             400
CGACC ATG GTG GCC GGG ACC CGC TGT CTT CTA GCG TTG CTG CTT CCC CAG GTC
      MET Val Ala Gly Thr Arg Cys Leu Leu Ala Leu Leu Leu Pro Gln Val 415             430             445
CTC CTG GGC GGC GCG GCT GGC CTC GTT CCG GAG CTG GGC CGC AGG AAG TTC GCG
Leu Leu Gly Gly Ala Ala Gly Leu Val Pro Glu Leu Gly Arg Arg Lys Phe Ala
                        (24)
460             475             490             505
GCG GCG TCG TCG GGC CGC CCC TCA TCC CAG CCC TCT GAC GAG GTC CTG AGC GAG
Ala Ala Ser Ser Gly Arg Pro Ser Ser Gln Pro Ser Asp Glu Val Leu Ser Glu 520             535             550             565
TTC GAG TTG CGG CTG CTC AGC ATG TTC GGC CTG AAA CAG AGA CCC ACC CCC AGC
Phe Glu Leu Arg Leu Leu Ser MET Phe Gly Leu Lys Gln Arg Pro Thr Pro Ser 580             595             610
AGG GAC GCC GTG GTG CCC CCC TAC ATG CTA GAC CTG TAT CGC AGG CAC TCA GGT
Arg Asp Ala Val Val Pro Pro Tyr MET Leu Asp Leu Tyr Arg Arg His Ser Gly 625             640             655             670
CAG CCG GGC TCA CCC GCC CCA GAC CAC CGG TTG GAG AGG GCA GCC AGC CGA GCC
Gln Pro Gly Ser Pro Ala Pro Asp His Arg Leu Glu Arg Ala Ala Ser Arg Ala
```

FIG. 1

```
                    685                     700                     715
AAC ACT GTG CGC AGC TTC CAC CAT GAA GAA TCT TTG GAA GAA CTA CCA GAA ACG
Asn Thr Val Arg Ser Phe His His Glu Glu Ser Leu Glu Glu Leu Pro Glu Thr 730                     745                     760                     775
AGT GGG AAA ACA ACC CGG AGA TTC TTC TTT AAT TTA AGT TCT ATC CCC ACG GAG
Ser Gly Lys Thr Thr Arg Arg Phe Phe Phe Asn Leu Ser Ser Ile Pro Thr Glu 790                     805                     820               835
GAG TTT ATC ACC TCA GCA GAG CTT CAG GTT TTC CGA GAA CAG ATG CAA GAT GCT
Glu Phe Ile Thr Ser Ala Glu Leu Gln Val Phe Arg Glu Gln MET Gln Asp Ala 850                     865                     880
TTA GGA AAC AAT AGC AGT TTC CAT CAC CGA ATT AAT ATT TAT GAA ATC ATA AAA
Leu Gly Asn Asn Ser Ser Phe His His Arg Ile Asn Ile Tyr Glu Ile Ile Lys 895                     910                     925                     940
CCT GCA ACA GCC AAC TCG AAA TTC CCC GTG ACC AGA CTT TTG GAC ACC AGG TTG
Pro Ala Thr Ala Asn Ser Lys Phe Pro Val Thr Arg Leu Leu Asp Thr Arg Leu 995                     970                     985
GTG AAT CAG AAT GCA AGC AGG TGG GAA AGT TTT GAT GTC ACC CCC GCT GTG ATG
Val Asn Gln Asn Ala Ser Arg Trp Glu Ser Phe Asp Val Thr Pro Ala Val MET 1000                    1015                    1030                    1045
CGG TGG ACT GCA CAG GGA CAC GCC AAC CAT GGA TTC GTG GTG GAA GTG GCC CAC
Arg Trp Thr Ala Gln Gly His Ala Asn His Gly Phe Val Val Glu Val Ala His 1060                    1075                    1090                   1105
TTG GAG GAG AAA CAA GGT GTC TCC AAG AGA CAT GTT AGG ATA AGC AGG TCT TTG
Leu Glu Glu Lys Gln Gly Val Ser Lys Arg His Val Arg Ile Ser Arg Ser Leu
                                                                        (249)
CAC CAA GAT GAA CAC AGC TGG TCA CAG ATA AGG CCA TTG CTA GTA ACT TTT GGC
His Gln Asp Glu His Ser Trp Ser Gln Ile Arg Pro Leu Leu Val Thr Phe Gly
                                                                        (266)
      1165                    1180                    1195                    1210
CAT GAT GGA AAA GGG CAT CCT CTC CAC AAA AGA GAA AAA CGT CAA GCC AAA CAC
His Asp Gly Lys Gly His Pro Leu His lys Arg Glu Lys Arg Gln Ala Lys His
                                                                        (283)
            1225                    1240                    1255
AAA CAG CGG AAA CGC CTT AAG TCC AGC TGT AAG AGA CAC CCT TTG TAC GTG GAC
Lys Gln Arg Lys Arg Leu Lys Ser Ser Cys Lys Arg His Pro Leu Tyr Val Asp
                                  (296)
1270                    1285                    1300                    1315
TTC AGT GAC GTG GGG TGG AAT GAC TGG ATT GTG GCT CCC CCG GGG TAT CAC GCC
Phe Ser Asp Val Gly Trp Asn Asp Trp Ile Val Ala Pro Pro Gly Tyr His Ala
```

FIG. 1 (CON'T)

```
                1330                    1345                    1360                    1375
       TTT TAC TGC CAC GGA GAA TGC CCT TTT CCT CTG GCT GAT CAT CTG AAC TCC ACT
       Phe Tyr Cys His Gly Glu Cys Pro Phe Pro Leu Ala Asp His Leu Asn Ser Thr 1390                    1405                    1420
       AAT CAT GCC ATT GTT CAG ACG TTG GTC AAC TCT GTT AAC TCT AAG ATT CCT AAG
       Asn His Ala Ile Val Gln Thr Leu Val Asn Ser Val Asn Ser Lys Ile Pro Lys 1435                    1450                    1465                    1480
       GCA TGC TGT GTC CCG ACA GAA CTC AGT GCT ATC TCG ATG CTG TAC CTT GAC GAG
       Ala Cys Cys Val Pro Thr Glu Leu Ser Ala Ile Ser MET Leu Tyr Leu Asp Glu 1495                    1510                    1525
       AAT GAA AAG GTT GTA TTA AAG AAC TAT CAG GAC ATG GTT GTG GAG GGT TGT GGG
       Asn Glu Lys Val Val Leu Lys Asn Tyr Gln Asp MET Val Val Glu Gly Cys Gly

1540(396)     1553      1563      1573      1583      1593      1603
   TGT CGC TAGTACAGCA AAATTAAATA CATAAATATA TATATATATA TATATTTTAG AAAAAAGAAA
   Cys Arg

AAAA
```

FIG. 1 (CON'T)

```
          10         20         30         40         50         60         70
CTCTAGAGGG CAGAGGAGGA GGGAGGGAGG GAAGGAGCGC GGAGCCCGGC CCGGAAGCTA GGTGAGTGTG 80         90        100        110        120        130        140
GCATCCGAGC TGAGGGACGC GAGCCTGAGA CGCCGCTGCT GCTCCGGCTG AGTATCTAGC TTGTCTCCCC 150        160        170        180        190        200        210
GATGGGATTC CCGTCCAAGC TATCTCGAGC CTGCAGCGCC ACAGTCCCCG GCCCTCGCCC AGGTTCACTG 220        230        240        250        260        270        280
CAACCGTTCA GAGGTCCCCA GGAGCTGCTG CTGGCGAGCC CGCTACTGCA GGGACCTATG GAGCCATTCC 290        300        310        320        330        340        350
GTAGTGCCAT CCCGAGCAAC GCACTGCTGC AGCTTCCCTG AGCCTTTCCA GCAAGTTTGT TCAAGATTGG 360        370        380        390        400        (1)
CTGTCAAGAA TCATGGACTG TTATTATATG CCTTGTTTTC TGTCAAGACA CC ATG ATT CCT
                                                         MET Ile Pro
     417                432                447                462
GGT AAC CGA ATG CTG ATG GTC GTT TTA TTA TGC CAA GTC CTG CTA GGA GGC GCG
Gly Asn Arg MET Leu Met Val Val Leu Leu Cys Gln Val Leu Leu Gly Gly Ala 477                492                507
AGC CAT GCT AGT TTG ATA CCT GAG ACG GGG AAG AAA AAA GTC GCC GAG ATT CAG
Ser His Ala Ser Leu Ile Pro Glu Thr Gly Lys Lys Lys Val Ala Glu Ile Gln 522                537                552                567
GGC CAC GCG GGA GGA CGC CGC TCA GGG CAG AGC CAT GAG CTC CTG CGG GAC TTC
Gly His Ala Gly Gly Arg Arg Ser Gly Gln Ser His Glu Leu Leu Arg Asp Phe 582                597                612                627
GAG GCG ACA CTT CTG CAG ATG TTT GGG CTG CGC CGC CGC CCG CAG CCT AGC AAG
Glu Ala Thr Leu Leu Gln MET Phe Gly Leu Arg Arg Arg Pro Gln Pro Ser Lys 642                657                672
AGT GCC GTC ATT CCG GAC TAC ATG CGG GAT CTT TAC CGG CTT CAG TCT GGG GAG
Ser Ala Val Ile Pro Asp Tyr MET Arg Asp Leu Tyr Arg Leu Gln Ser Gly Glu
```

*FIG. 2*

```
      687                  702                  717                  732
GAG GAG GAA GAG CAG ATC CAC AGC ACT GGT CTT GAG TAT CCT GAG CGC CCG GCC
Glu Glu Glu Glu Gln Ile His Ser Thr Gly Leu Glu Tyr Pro Glu Arg Pro Ala 747                  762                  777
AGC CGG GCC AAC ACC GTG AGG AGC TTC CAC CAC GAA GAA CAT CTG GAG AAC ATC
Ser Arg Ala Asn Thr Val Arg Ser Phe His His Glu Glu His Leu Glu Asn Ile 792                  807                  822                  837
CCA GGG ACC AGT GAA AAC TCT GCT TTT CGT TTC CTC TTT AAC CTC AGC AGC ATC
Pro Gly Thr Ser Glu Asn Ser Ala Phe Arg Phe Leu Phe Asn Leu Ser Ser Ile 852                  867                  882                  897
CCT GAG AAC GAG GTG ATC TCC TCT GCA GAG CTT CGG CTC TTC CGG GAG CAG GTG
Pro Glu Asn Glu Val Ile Ser Ser Ala Glu Leu Arg Leu Phe Arg Glu Gln Val 912                  927                  942
GAC CAG GGC CCT GAT TGG GAA AGG GGC TTC CAC CGT ATA AAC ATT TAT GAG GTT
Asp Gln Gly Pro Asp Trp Glu Arg Gly Phe His Arg Ile Asn Ile Tyr Glu Val 957                  972                  987                  1002
ATG AAG CCC CCA GCA GAA GTG GTG CCT GGG CAC CTC ATC ACA CGA CTA CTG GAC
MET Lys Pro Pro Ala Glu Val Val Pro Gly His Leu Ile Thr Arg Leu Leu Asp 1017                 1032                 1047
ACG AGA CTG GTC CAC CAC AAT GTG ACA CGG TGG GAA ACT TTT GAT GTG AGC CCT
Thr Arg Leu Val His His Asn Val Thr Arg Trp Glu Thr Phe Asp Val Ser Pro 1062                 1077                 1092                 1107
GCG GTC CTT CGC TGG ACC CGG GAG AAG CAG CCA AAC TAT GGG CTA GCC ATT GAG
Ala Val Leu Arg Trp Thr Arg Glu Lys Gln Pro Asn Tyr Gly Leu Ala Ile Glu 1122                 1137                 1152                 1167
GTG ACT CAC CTC CAT CAG ACT CGG ACC CAC CAG GGC CAG CAT GTC AGG ATT AGC
Val Thr His Leu His Gln Thr Arg Thr His Gln Gly Gln His Val Arg Ile Ser 1182                 1197                 1212
CGA TCG TTA CCT CAA GGG AGT GGG AAT TGG GCC CAG CTC CGG CCC CTC CTG GTC
Arg Ser Leu Pro Gln Gly Ser Gly Asn Trp Ala Gln Leu Arg Pro Leu Leu Val 1227                 1242                 1257                 1272
ACC TTT GGC CAT GAT GGC CGG GGC CAT GCC TTG ACC CGA CGC CGG AGG GCC AAG
Thr Phe Gly His Asp Gly Arg Gly His Ala Leu Thr Arg Arg Arg Arg Ala Lys 1287                 1302                 1317
CGT AGC CCT AAG CAT CAC TCA CAG CGG GCC AGG AAG AAG AAT AAG AAC TGC CGG
Arg Ser Pro Lys His His Ser Gln Arg Ala Arg Lys Lys Asn Lys Asn Cys Arg
    (293)
```

FIG. 2 (CON'T)

```
1332                1347                1362                1377
CGC CAC TCG CTC TAT GTG GAC TTC AGC GAT GTG GGC TGG AAT GAC TGG ATT GTG
Arg His Ser Leu Tyr Val Asp Phe Ser Asp Val Gly Trp Asn Asp Trp Ile Val 1392                1407                1422                1437
GCC CCA CCA GGC TAC CAG GCC TTC TAC TGC CAT GGG GAC TGC CCC TTT CCA CTG
Ala Pro Pro Gly Tyr Gln Ala Phe Tyr Cys His Gly Asp Cys Pro Phe Pro Leu 1452                1467                1482
GCT GAC CAC CTC AAC TCA ACC AAC CAT GCC ATT GTG CAG ACC CTG GTC AAT TCT
Ala Asp His Leu Asn Ser Thr Asn His Ala Ile Val Gln Thr Leu Val Asn Ser 1497                1512                1527                1542
GTC AAT TCC AGT ATC CCC AAA GCC TGT TGT GTG CCC ACT GAA CTG AGT GCC ATC
Val Asn Ser Ser Ile Pro Lys Ala Cys Cys Val Pro Thr Glu Leu Ser Ala Ile 1557                1572                1587
TCC ATG CTG TAC CTG GAT GAG TAT GAT AAG GTG GTA CTG AAA AAT TAT CAG GAG
Ser MET Leu Tyr Leu Asp Glu Tyr Asp Lys Val Val Leu Lys Asn Tyr Gln Glu 1602                1617    (408)    1636       1646       1656
ATG GTA GTA GAG GGA TGT GGG TGC CGC TGAGATCAGG CAGTCCTTGA GGATAGACAG
MET Val Val Glu Gly Cys Gly Cys Arg 1666       1676       1686       1696       1706       1716       1726
ATATACACAC CACACACACA CACCACATAC ACCACACACA CACGTTCCCA TCCACTCACC CACACACTAC 1736       1746       1756       1766       1776       1786       1796
ACAGACTGCT TCCTTATAGC TGGACTTTTA TTTAAAAAAA AAAAAAAAAA AATGGAAAAA ATCCCTAAAC 1806       1816       1826       1836       1846       1856       1866
ATTCACCTTG ACCTTATTTA TGACTTTACG TGCAAATGTT TTGACCATAT TGATCATATA TTTTGACAAA 1876       1886       1896       1906       1916       1926       1936
ATATATTTAT AACTACGTAT TAAAAGAAAA AAATAAAATG AGTCATTATT TTAAAAAAAA AAAAAAACT

1946
CTAGAGTCGA CGGAATTC
```

FIG. 2 (CON'T)

```
                 10         20         30         40         50
        GTGACCGAGC GGCGCGGACG GCCGCCTGCC CCCTCTGCCA CCTGGGGCGG 60         70         80         90         99
        TGCGGGCCCG GAGCCCGGAG CCCGGGTAGC GCGTAGAGCC GGCGCG ATG
                                                           MET
                                                           (1)

108         117         126         135         144
CAC GTG CGC TCA CTG CGA GCT GCG GCG CCG CAC AGC TTC GTG GCG
His Val Arg Ser Leu Arg Ala Ala Ala Pro His Ser Phe Val Ala 153         162         171         180         189
CTC TGG GCA CCC CTG TTC CTG CTG CGC TCC GCC CTG GCC GAC TTC
Leu Trp Ala Pro Leu Phe Leu Leu Arg Ser Ala Leu Ala Asp Phe 198         207         216         225         234
AGC CTG GAC AAC GAG GTG CAC TCG AGC TTC ATC CAC CGG CGC CTC
Ser Leu Asp Asn Glu Val His Ser Ser Phe Ile His Arg Arg Leu 243         252         261         270         279
CGC AGC CAG GAG CGG CGG GAG ATG CAG CGC GAG ATC CTC TCC ATT
Arg Ser Gln Glu Arg Arg Glu MET Gln Arg Glu Ile Leu Ser Ile 288         297         306         315         324
TTG GGC TTG CCC CAC CGC CCG CGC CCG CAC CTC CAG GGC AAG CAC
Leu Gly Leu Pro His Arg Pro Arg Pro His Leu Gln Gly Lys His 333         342         351         360         369
AAC TCG GCA CCC ATG TTC ATG CTG GAC CTG TAC AAC GCC ATG GCG
Asn Ser Ala Pro MET Phe MET Leu Asp Leu Tyr Asn Ala MET Ala 378         387         396         405         414
GTG GAG GAG GGC GGC GGG CCC GGC GGC CAG GGC TTC TCC TAC CCC
Val Glu Glu Gly Gly Gly Pro Gly Gly Gln Gly Phe Ser Tyr Pro 423         432         441         450         459
TAC AAG GCC GTC TTC AGT ACC CAG GGC CCC CCT CTG GCC AGC CTG
Tyr Lys Ala Val Phe Ser Thr Gln Gly Pro Pro Leu Ala Ser Leu 468         477         486         495         504
CAA GAT AGC CAT TTC CTC ACC GAC GCC GAC ATG GTC ATG AGC TTC
Gln Asp Ser His Phe Leu Thr Asp Ala Asp MET Val MET Ser Phe 513         522         531         540         549
GTC AAC CTC GTG GAA CAT GAC AAG GAA TTC TTC CAC CCA CGC TAC
Val Asn Leu Val Glu His Asp Lys Glu Phe Phe His Pro Arg Tyr
```

*FIG. 3*

```
      558           567           576           585           594
CAC CAT CGA GAG TTC CGG TTT GAT CTT TCC AAG ATC CCA GAA GGG
His His Arg Glu Phe Arg Phe Asp Leu Ser Lys Ile Pro Glu Gly 603           612           621           630           639
GAA GCT GTC ACG GCA GCC GAA TTC CGG ATC TAC AAG GAC TAC ATC
Glu Ala Val Thr Ala Ala Glu Phe Arg Ile Tyr Lys Asp Tyr Ile 648           657           666           675           684
CGG GAA CGC TTC GAC AAT GAG ACG TTC CGG ATC AGC GTT TAT CAG
Arg Glu Arg Phe Asp Asn Glu Thr Phe Arg Ile Ser Val Tyr Gln 693           702           711           720           729
GTG CTC CAG GAG CAC TTG GGC AGG GAA TCG GAT CTC TTC CTG CTC
Val Leu Gln Glu His Leu Gly Arg Glu Ser Asp Leu Phe Leu Leu 738           747           756           765           774
GAC AGC CGT ACC CTC TGG GCC TCG GAG GAG GGC TGG CTG GTG TTT
Asp Ser Arg Thr Leu Trp Ala Ser Glu Glu Gly Trp Leu Val Phe 783           792           801           810           819
GAC ATC ACA GCC ACC AGC AAC CAC TGG GTG GTC AAT CCG CGG CAC
Asp Ile Thr Ala Thr Ser Asn His Trp Val Val Asn Pro Arg His 828           837           846           855           864
AAC CTG GGC CTG CAG CTC TCG GTG GAG ACG CTG GAT GGG CAG AGC
Asn Leu Gly Leu Gln Leu Ser Val Glu Thr Leu Asp Gly Gln Ser 873           882           891           900           909
ATC AAC CCC AAG TTG GCG GGC CTG ATT GGG CGG CAC GGG CCC CAG
Ile Asn Pro Lys Leu Ala Gly Leu Ile Gly Arg His Gly Pro Gln 918           927           936           945           954
AAC AAG CAG CCC TTC ATG GTG GCT TTC TTC AAG GCC ACG GAG GTC
Asn Lys Gln Pro Phe MET Val Ala Phe Phe Lys Ala Thr Glu Val 963           972           981           990           999
CAC TTC CGC AGC ATC CGG TCC ACG GGG AGC AAA CAG CGC AGC CAG
His Phe Arg Ser Ile Arg Ser Thr Gly Ser Lys Gln Arg Ser Gln
                              (293)
      1008          1017          1026          1035          1044
AAC CGC TCC AAG ACG CCC AAG AAC CAG GAA GCC CTG CGG ATG GCC
Asn Arg Ser Lys Thr Pro Lys Asn Gln Glu Ala Leu Arg MET Ala
                                   ‾‾‾ ‾‾‾ ‾‾‾ ‾‾‾ ‾‾‾ ‾‾‾
      1053          1062          1071          1080          1089
AAC GTG GCA GAG AAC AGC AGC AGC GAC CAG AGG CAG GCC TGT AAG
Asn Val Ala Glu Asn Ser Ser Ser Asp Gln Arg Gln Ala Cys Lys
```

FIG. 3 (CON'T)

```
      1098            1107            1116            1125            1134
AAG CAC GAG CTG TAT GTC AGC TTC CGA GAC CTG GGC TGG CAG GAC
Lys His Glu Leu Tyr Val Ser Phe Arg Asp leu Gly Trp Gln Asp 1143            1152            1161            1170            1179
TGG ATC ATC GCG CCT GAA GGC TAC GCC GCC TAC TAC TGT GAG GGG
Trp Ile Ile Ala Pro Glu Gly Tyr Ala Ala Tyr Tyr Cys Glu Gly 1188            1197            1206            1215            1224
GAG TGT GCC TTC CCT CTG AAC TCC TAC ATG AAC GCC ACC AAC CAC
Glu Cys Ala Phe Pro Leu Asn Ser Tyr MET Asn Ala Thr Asn His 1233            1242            1251            1260            1269
GCC ATC GTG CAG ACG CTG GTC CAC TTC ATC AAC CCG GAA ACG GTG
Ala Ile Val Gln Thr Leu Val His Phe Ile Asn Pro Ile Ser Val 1278            1287            1296            1305            1314
CCC AAG CCC TGC TGT GCG CCC ACG CAG CTC AAT GCC ATC TCC GTC
Pro Lys Pro Cys Cys Ala Pro Thr Gln Leu Asn Ala Ile Ser Val 1323            1332            1341            1350            1359
CTC TAC TTC GAT GAC AGC TCC AAC GTC ATC CTG AAG AAA TAC AGA
Leu Tyr Phe asp Asp Ser Ser Asn Val Ile Leu lys Lys Tyr Arg 1368            1377            1386            1399
AAC ATG GTG GTC CGG GCC TGT GGC TGC CAC TAGCTCCTCC
Asn MET VAl Val Arg Ala Cys Gly Cys His
                                    (431)

1409      1419      1429      1439      1448
GAGAATTCAG ACCCTTTGGG GCCAAGTTTT TCTGGATCCT CCATTGCTC
```

FIG. 3 (CON'T)

```
            10          20          30          40          50
   CGACCATGAG AGATAAGGAC TGAGGGCCAG GAAGGGGAAG CGAGCCCGCC 60          70          80          90         100
   GAGAGGTGGC GGGGACTGCT CACGCCAAGG GCCACAGCGG CCGCGCTCCG 110         120         130         140         150
   GCCTCGCTCC GCCGCTCCAC GCCTCGCGGG ATCCGCGGGG GCAGCCCGGC 159         168         177         186         195
   CGGGCGGGG ATG CCG GGG CTG GGG CGG AGG GCG CAG TGG CTG TGC
              MET Pro Gly Leu Gly Arg Arg Ala Gln Trp Leu cys
              (1)

204         213         222         231         240
   TGG TGG TGG GGG CTG CTG TGC AGC TGC TGC GGG CCC CCG CCG CTG
   Trp Trp Trp Gly Leu Leu Cys Ser Cys Cys Gly Pro Pro Pro Leu 249         258         267         276         285
   CGG CCG CCC TTG CCC GCT GCC GCG GCC GCC GCC GCC GGG GGG CAG
   Arg Pro Pro Leu pro Ala Ala Ala Ala Ala Ala Ala Gly Gly Gln 294         303         312         321         330
   CTG CTG GGG GAC GGC GGG AGC CCC GGC CGC ACG GAG CAG CCG CCG
   Leu Leu Gly Asp Gly Gly Ser Pro Gly Arg Thr Glu Gln Pro Pro 339         348         357         366         375
   CCG TCG CCG CAG TCC TCC TCG GGC TTC CTG TAC CGG CGG CTC AAG
   Pro Ser Pro Gln Ser Ser Ser Gly Phe Leu Tyr Arg Arg Leu Lys 384         393         402         411         420
   ACG CAG GAG AAG CGG GAG ATG CAG AAG GAG ATC TTG TCG GTG CTG
   Thr Gln Glu Lys Arg Glu MET gln Lys Glu Ile Leu Ser Val Leu 429         438         447         456         465
   GGG CTC CCG CAC CGG CCC CGG CCC CTG CAC GGC CTC CAA CAG CCG
   Gly Leu Pro His Arg Pro Arg Pro Leu His Gly Leu Gln Gln Pro
```

*FIG. 4*

```
            474         483         492         501         510
CAG CCC CCG GCG CTC CGG CAG CAG GAG GAG CAG CAG CAG CAG CAG
Gln Pro Pro Ala Leu Arg Gln Gln Glu glu Gln Gln Gln Gln Gln 519         528         537         546         555
CAG CTG CCT CGC GGA GAG CCC CCT CCC GGG CGA CTG AAG TCC GCG
Gln Leu Pro Arg Gly Glu Pro Pro Pro Gly Arg Leu Lys Ser Ala 564         573         582         591         600
CCC CTC TTC ATG CTG GAT CTG TAC AAC GCC CTG TCC GCC GAC AAC
Pro Leu Phe MET Leu Asp Leu Tyr Asn Ala Leu Ser Ala Asp Asn 609         618         627         636         645
GAC GAG GAC GGG GCG TCG GAG GGG GAG AGG CAG CAG TCC TGG CCC
Asp Glu asp Gly Ala Ser Glu Gly Glu Arg Gln Gln Ser Trp Pro 654         663         672         681         690
CAC GAA GCA GCC AGC TCG TCC CAG CGT CGG CAG CCG CCC CCG GGC
His Glu Ala Ala Ser Ser Ser Gln Arg Arg Gln Pro Pro Pro Gly 699         708         717         726         735
GCC GCG CAC CCG CTC AAC CGC AAG AGC CTT CTG GCC CCC GGA TCT
Pro Pro Gly Ala Ala His Pro Leu Asn Arg Lys Ser Leu Leu Ala 744         753         762         771         780
GGC AGC GGC GGC GCG TCC CCA CTG ACC AGC GCG CAG GAC AGC GCC
Gly Ser Gly Gly Ala Ser Pro Leu Thr Ser Ala Gln Asp Ser Ala 789         798         807         816         825
TTC CTC AAC GAC GCG GAC ATG GTC ATG AGC TTT GTG AAC CTG GTG
Phe Leu Asn Asp Ala Asp MET Val MET Ser Phe Val Asn Leu Val 834         843         852         861         870
GAG TAC GAC AAG GAG TTC TCC CCT CGT CAG CGA CAC CAC AAA GAG
Glu Tyr Asp Lys Glu Phe Ser Pro Arg Gln Arg His His Lys Glu 879         888         897         906         915
TTC AAG TTC AAC TTA TCC CAG ATT CCT GAG GGT GAG GTG GTG ACG
Phe Lys Phe Asn leu Ser Gln Ile Pro Glu Gly Glu Val Val Thr 924         933         942         951         960
GCT GCA GAA TTC CGC ATC TAC AAG GAC TGT GTT ATG GGG AGT TTT
Phe Arg Ile Tyr Lys Asp Cys Val MEt Ala Ala Glu Gly Ser Phe
```

*FIG. 4 (CON'T)*

```
          969           978           987           996          1005
AAA AAC CAA ACT TTT CTT ATC AGC ATT TAT CAA GTC TTA CAG GAG
Lys Asn Gln Thr Phe Leu Ile Ser Ile Tyr Gln Val Leu Gln Glu 1014          1023          1032          1041          1050
CAT CAG CAC AGA GAC TCT GAC CTG TTT TTG TTG GAC ACC CGT GTA
His Gln His Arg Asp Ser Asp Leu Phe Leu Leu Asp Thr Arg Val 1059          1068          1077          1086          1095
GTA TGG GCC TCA GAA GAA GGC TGG CTG GAA TTT GAC ATC ACG GCC
Val Trp Ala Ser Glu Glu Gly Trp Leu Glu Phe Asp Ile Thr Ala 1104          1113          1122          1131          1140
ACT AGC AAT CTG TGG GTT GTG ACT CCA CAG CAT AAC ATG GGG CTT
Thr Ser Asn Leu Trp Val Val Thr Pro Gln His Asn MET Gly Leu 1149          1158          1167          1176          1185
CAG CTG AGC GTG GTG ACA AGG GAT GGA GTC CAC GTC CAC CCC CGA
Gln Leu Ser Val Val Thr Arg Asp Gly Val His Val His Pro Arg 1194          1203          1212          1221          1230
GCC GCA GGC CTG GTG GGC AGA GAC GGC CCT TAC GAT AAG CAG CCC
Ala Ala Gly Leu Val Gly Arg Asp Gly Pro Tyr Asp Lys Gln Pro 1239          1248          1257          1266          1275
TTC ATG GTG GCT TTC TTC AAA GTG AGT GAG GTC CAC GTG CGC ACC
Phe MET Val Ala Phe Phe Lys Val Ser Glu Val His Val Arg Thr 1284          1293          1302          1311          1320
ACC AGG TCA GCC TCC AGC CGG CGC CGA CAA CAG AGT CGT AAT CGC
Thr Arg Ser Ala Ser Ser Arg Arg Arg Gln Gln Ser Arg Asn Arg
                                         (382)
         1329          1338          1347          1356          1365
TCT ACC CAG TCC CAG GAC GTG GCG CGG GTC TCC AGT GCT TCA GAT
Ser The Gln Ser Gln Asp Val Ala Arg Val Ser Ser Ala Ser Asp
(388)
         1374          1383          1392          1401          1410
TAC AAC AGC AGT GAA TTG AAA ACA GCC TGC AGG AAG CAT GAG CTG
Tyr Asn Ser Ser Glu Leu Lys Thr Ala Cys Arg Lys His Glu Leu
                                                 (412)
         1419          1428          1437          1446          1455
TAT GTG AGT TTC CAA GAC CTG GGA TGG CAG GAC TGG ATC ATT GCA
Tyr Val Ser Phe Gln Asp Leu Gly Trp Gln Asp Trp Ile Ile Ala
```

FIG. 4 (CON'T)

```
            1464            1473            1482            1491            1500
CCC AAG GGC TAT GCT GCC AAT TAC TGT GAT GGA GAA TGC TCC TTC
Pro Lys Gly Tyr Ala Ala Asn Tyr Cys Asp Gly Glu Cys Ser Phe 1509            1518            1527            1536            1545
CCA CTC AAC GCA CAC ATG AAT GCA ACC AAC CAC GCG ATT GTG CAG
Pro Leu Asn Ala His MET Asn Ala Thr Asn His Ala Ile Val Gln 1554            1563            1572            1581            1590
ACC TTG GTT CAC CTT ATG AAC CCC GAG TAT GTC CCC AAA CCG TGC
Thr Leu Val His Leu MET Asn Pro Glu Tyr Val Pro Lys Pro Cys 1599            1608            1617            1626            1635
TGT GCG CCA ACT AAG CTA AAT GCC ATC TCG GTT CTT TAC TTT GAT
Cys Ala Pro Thr Lys Leu Asn Ala Ile Ser Val Leu Tyr Phe Asp 1644            1653            1662            1671            1680
GAC AAC TCC AAT GTC ATT CTG AAA AAA TAC AGG AAT ATG GTT GTA
Asp Asn Ser Asn Val Ile Leu Lys Lys Tyr Arg Asn MET Val Val 1689            1698            1708            1718            1728
AGA GCT TGT GGA TGC CAC TAACTCGAAA CCAGATGCTG GGACACACA
Arg Ala Cys Gly Cys His
                   (513)
            1738            1748            1758            1768            1778
TTCTGCCTTG GATTCCTAGA TTACATCTGC CTTAAAAAAA CACGGAAGCA 1788            1798            1808            1818            1828
CAGTTGGAGG TGGGACGATG AGACTTTGAA ACTATCTCAT GCCAGTGCCT 1838            1848            1858            1868            1878
TATTACCCAG GAAGATTTTA AAGGACCTCA TTAATAATTT GCTCACTTGG 1888            1898            1908            1918            1928
TAAATGACGT GAGTAGTTGT TGGTCTGTAG CAAGCTGAGT TTGGATGTCT 1938            1948            1958            1968            1978
GTAGCATAAG GTCTGGTAAC TGCAGAAACA TAACCGTGAA GCTCTTCCTA 1988            1998            2008            2018            2028
CCCTCCTCCC CCAAAAACCC ACCAAAATTA GTTTTAGCTG TAGATCAAGC 2038            2048            2058            2068            2078
TATTTGGGGT GTTTGTTAGT AAATAGGGAA AATAATCTCA AAGGAGTTAA 2088            2098            2108            2118            2128
ATGTATTCTT GGCTAAAGGA TCAGCTGGTT CAGTACTGTC TATCAAAGGT
```

FIG. 4 (CON'T)

```
     2138       2148       2158       2168       2178
AGATTTTACA GAGAACAGAA ATCGGGGAAG TGGGGGGAAC GCCTCTGTTC 2188       2198       2208       2218       2228
AGTTCATTCC CAGAAGTCCA CAGGACGCAC AGCCCAGGCC ACAGCCAGGG 2238       2248       2258       2268       2278
CTCCACGGGG CGCCCTTGTC TCAGTCATTG CTGTTGTATG TTCGTGCTGG 2288       2298       2308       2318       2328
AGTTTTGTTG GTGTGAAAAT ACACTTATTT CAGCCAAAAC ATACCATTTC 2338       2348       2358       2368       2378
TACACCTCAA TCCTCCATTT GCTGTACTCT TTGCTAGTAC CAAAAGTAGA 2388       2398       2408       2418       2428
CTGATTACAC TGAGGTGAGG CTACAAGGGG TGTGTAACCG TGTAACACGT 2438       2448       2458       2458       2478
GAAGGCAGTG CTCACCTCTT CTTTACCAGA ACGGTTCTTT GACCAGCACA 2488       2498       2508       2518       2528
TTAACTTCTG GACTGCCGGC TCTAGTACCT TTTCAGTAAA GTGGTTCTCT 2538       2548       2558       2568       2578
GCCTTTTTAC TATACAGCAT ACCACGCCAC AGGGTTAGAA CCAACGAAGA 2588       2598       2608       2618       2628
AAATAAAATG AGGGTGCCCA GCTTATAAGA ATGGTGTTAG GGGGATGAGC 2638       2648       2658       2668       2678
ATGCTGTTTA TGAACGGAAA TCATGATTTC CCTGTAGAAA GTGAGGCTCA 2688       2698       2708       2718       2728
GATTAAATTT TAGAATATTT TCTAAATGTC TTTTTCACAA TCATGTGACT 2738       2748       2758       2768       2778
GGGAAGGCAA TTTCATACTA AACTGATTAA ATAATACATT TATAATCTAC 2788       2798       2808       2818       2828
AACTGTTTGC ACTTACAGCT TTTTTTGTAA ATATAAACTA TAATTTATTG 2838       2848       2858       2868       2878
TCTATTTTAT ATCTGTTTTG CTGTGGCGTT GGGGGGGGGG CCGGGCTTTT 2888       2898       2908       2918
GGGGGGGGGG GTTTGTTTGG GGGGTGTCGT GGTGTGGGCG GGCGG
```

FIG. 4 (CON'T)

```
         10         20         30         40         50
CTGGTATATT TGTGCCTGCT GGAGGTGGAA TTAACAGTAA GAAGGAGAAA 60         70         80         90        100
GGGATTGAAT GGACTTACAG GAAGGATTTC AAGTAAATTC AGGGAAACAC 110        120        130        140        150
ATTTACTTGA ATAGTACAAC CTAGAGTATT ATTTTACACT AAGACGACAC 160        170        180        190        200
AAAAGATGTT AAAGTTATCA CCAAGCTGCC GGACAGATAT ATATTCCAAC 210        220        230        240        250
ACCAAGGTGC AGATCAGCAT AGATCTGTGA TTCAGAAATC AGGATTTGTT 260        270        280        290        300
TTGGAAAGAG CTCAAGGGTT GAGAAGAACT CAAAAGCAAG TGAAGATTAC 310        320        330        340        350
TTTGGGAACT ACAGTTTATC AGAAGATCAA CTTTTGCTAA TTCAAATACC 360        370        380        390        400
AAAGGCCTGA TTATCATAAA TTCATATAGG AATGCATAGG TCATCTGATC 410        420        430        440        450
AAATAATATT AGCCGTCTTC TGCTACATCA ATGCAGCAAA AACTCTTAAC 460        470        480        490        500
AACTGTGGAT AATTGGAAAT CTGAGTTTCA GCTTTCTTAG AAATAACTAC 510        520        530        540        550
TCTTGACATA TTCCAAAATA TTTAAAATAG GACAGGAAAA TCGGTGAGGA 560        570        580        590        600
TGTTGTGCTC AGAAATGTCA CTGTCATGAA AAATAGGTAA ATTTGTTTTT 610        620        630        640        650
TCAGCTACTG GGAAACTGTA CCTCCTAGAA CCTTAGGTTT TTTTTTTTTT 660        670        680        690        700
AAGAGGACAA GAAGGACTAA AAATATCAAC TTTTGCTTTT GGACAAAA
```

FIG. 5

```
701              710              719              728              737
ATG CAT CTG ACT GTA TTT TTA CTT AAG GGT ATT GTG GGT TTC CTC
MET His Leu Thr Val Phe Leu Leu Lys Gly Ile Val Gly Phe Leu
(1)
746              755              764              773              782
TGG AGC TGC TGG GTT CTA GTG GGT TAT GCA AAA GGA GGT TTG GGA
Trp Ser Cys Trp Val Leu Val Gly Tyr Ala Lys Gly Gly Leu Gly 791              800              809              818              827
GAC AAT CAT GTT CAC TCC AGT TTT ATT TAT AGA AGA CTA CGG AAC
Asp Asn His Val His Ser Ser Phe Ile Tyr Arg Arg Leu Arg Asn 836              845              854              863              872
CAC GAA AGA CGG GAA ATA CAA AGG GAA ATT CTC TCT ATC TTG GGT
His Glu Arg Arg Glu Ile Gln arg Glu Ile Leu Ser Ile Leu Gly 881              890              899              908              917
TTG CCT CAC AGA CCC AGA CCA TTT TCA CCT GGA AAA ATG ACC AAT
Leu Pro His Arg Pro Arg Pro Phe Ser Pro Gly Lys Gln Ala Ser 926              935              944              953              962
CAA GCG TCC TCT GCA CCT CTC TTT ATG CTG GAT CTC TAC AAT GCC
Ser Ala Pro Leu Phe MET Leu Asp Leu Tyr Asn Ala MET Thr Asn 971              980              989              998              1007
GAA GAA AAT CCT GAA GAG TCG GAG TAC TCA GTA AGG GCA TCC TTG
Glu Glu Asn Pro Glu Glu Ser Glu Tyr Ser Val Arg Ala Ser Leu 1016             1025             1034             1043             1052
GCA GAA GAG ACC AGA GGG GCA AGA AAG GGA TAC CCA GCC TCT CCC
Ala Glu Glu Thr Arg Gly Ala Arg Lys Gly Tyr Pro Ala Ser Pro 1061             1070             1079             1088             1097
AAT GGG TAT CCT CGT CGC ATA CAG TTA TCT CGG ACG ACT CCT CTG
Asn Gly Tyr Pro Arg Arg Ile Gln Leu Ser Arg Thr Thr Pro Leu 1106             1115             1124             1133             1142
ACC ACC CAG AGT CCT CCT CTA GCC AGC CTC CAT GAT ACC AAC TTT
Thr Thr Gln Ser Pro Pro Leu Ala Ser Leu His Asp Thr Asn Phe 1151             1160             1169             1178             1187
CTG AAT GAT GCT GAC ATG GTC ATG AGC TTT GTC AAC TTA GTT GAA
Leu Asn Asp Ala Asp MET Val MET Ser Phe Val Asn Leu Val Glu 1196             1205             1214             1223             1232
AGA GAC AAG GAT TTT TCT CAC CAG CGA AGG CAT TAC AAA GAA TTT
Arg Asp Lys Asp Phe Ser His Gln Arg Arg His Tyr Lys Glu Phe
```

FIG. 5 (CON'T)

```
1241           1250           1259           1268           1277
CGA TTT GAT CTT ACC CAA ATT CCT CAT GGA GAG GCA GTG ACA GCA
Arg Phe Asp Leu Thr Gln Ile Pro His Gly Glu Ala Val Thr Ala 1286           1295           1304           1313           1322
GCT GAA TTC CGG ATA TAC AAG GAC CGG AGC AAC AAC CGA TTT GAA
Ala Glu Phe Arg Ile Tyr Lys Asp Arg Ser Asn Asn Arg Phe Glu 1331           1340           1349           1358           1367
AAT GAA ACA ATT AAG ATT AGC ATA TAT CAA ATC ATC AAG GAA TAC
Asn Glu Thr Ile Lys Ile Ser Ile Tyr Gln Ile Ile Lys Glu Tyr 1376           1385           1394           1403           1412
ACA AAT AGG GAT GCA GAT CTG TTC TTG TTA GAC ACA AGA AAG GCC
Thr Asn Arg Asp Ala Asp Leu Phe Leu Leu Asp Thr Arg Lus Ala 1421           1430           1439           1448           1457
CAA GCT TTA GAT GTG GGT TGG CTT GTC TTT GAT ATC ACT GTG ACC
Gln Ala Leu Asp Val Gly Trp Leu Val Phe Asp Ile Thr Val Thr 1466           1475           1484           1493           1502
AGC AAT CAT TGG GTG ATT AAT CCC CAG AAT AAT TTG GGC TTA CAG
Ser Asn His Trp Val Ile Asn Pro Gln Asn Asn Leu Gly Leu Gln 1511           1520           1529           1538           1547
CTC TGT GCA GAA ACA GGG GAT GGA CGC AGT ATC AAC GTA AAA TCT
Leu Cys Ala Glu Thr Gly Asp Gly Arg Ser Ile Asn Val Lys Ser 1556           1565           1574           1583           1592
GCT GGT CTT GTG GGA AGA CAG GGA CCT CAG TCA AAA CAA CCA TTC
Ala Gly Leu Val Gly Arg Gln Gly Pro Gln Ser Lys Gln Pro Phe 1601           1610           1619           1628           1637
ATG GTG GCC TTC TTC AAG GCG AGT GAG GTA CTT CTT CGA TCC GTG
MET Val Ala Phe Phe Lys Ala Ser Glu VAl Leu Leu Arg Ser Val 1646           1655           1664           1673           1682
AGA GCA GCC AAC AAA CGA AAA AAT CAA AAC CGC AAT AAA TCC AGC
Arg Ala Ala Asn Lys Arg Lys Asn Gln Asn Arg Asn Lys Ser Ser
                                                      (329)
1691           1700           1709           1718           1727
TCT CAT CAG GAC TCC TCC AGA ATG TCC AGT GTT GGA GAT TAT AAC
Ser His Gln Asp Ser Ser Arg MET Ser Ser Val Gly Asp Tyr Asn
                        (337)
```

FIG. 5 (CON'T)

```
1736        1745        1754        1763        1722
 ACA AGT GAG CAA AAA CAA GCC TGT AAG AAG CAC GAA CTC TAT GTG
 Thr Ser Glu Gln Lys Gln Ala Cys Lys Lys His Glu Leu Tyr Val
                                         (356)

1781        1790        1799        1808        1817
 AGC TTC CGG GAT CTG GGA TGG CAG GAC TGG ATT ATA GCA CCA GAA
 Ser Phe Arg Asp Leu Gly Trp Gln Asp Trp Ile Ile Ala Pro Glu
 (362)
 1826        1835        1844        1853        1862
 GGA TAC GCT GCA TTT TAT TGT GAT GGA GAA TGT TCT TTT CCA CTT
 Gly Tyr Ala Ala Phe Tyr Cys Asp Gly Glu Cys Ser Phe Pro Leu 1871        1880        1889        1898        1907
 AAC GCC CAT ATG AAT GCC ACC AAC CAC GCT ATA GTT CAG ACT CTG
 Asn Ala His MET Asn Ala Thr Asn His Ala Ile Val Gln Thr Leu 1916        1925        1934        1943        1952
 GTT CAT CTG ATG TTT CCT GAC CAC GTA CCA AAG CCT TGT TGT GCT
 Val His Leu MET Phe Pro Asp His Val Pro Lys Pro Cys Cys Ala 1961        1970        1979        1988        1997
 CCA ACC AAA TTA AAT GCC ATC TCT GTT CTG TAC TTT GAT GAC AGC
 Pro Thr Lys Leu Asn Ala Ile Ser Val Leu Tyr Phe Asp Asp Ser 2006        2015        2024        2033        2042
 TCC AAT GTC ATT TTG AAA AAA TAT AGA AAT ATG GTA GTA CGC TCA
 Ser Asn Val Ile Leu Lys Lys Tyr Arg Asn MET Val Val Arg Ser 2051        2060        2070        2080        2090        2100
 TGT GGC TGC CAC TAATATTAAA TAATATTGAT AATAACAAAA AGATCTGTAT
 Cys Gly Cys His
                (454)
        2110        2120        2130        2140        2150
 TAAGGTTTAT GGCTGCAATA AAAGCATAC TTTCAGACAA ACAGAAAAAA AAA
```

FIG. 5 (CON'T)

```
            (1)
GAATTCC GAG CCC CAT TGG AAG GAG TTC CGC TTT GAC CTG ACC CAG ATC CCG GCT
        Glu Pro His Trp Lys Glu Phe Arg Phe Asp Leu Thr Gln Ile Pro Ala
                                                (10)

GGG GAG GCG GTC ACA GCT GCG GAG TTC CGG ATT TAC AAG GTG CCC AGC ATC CAC
Gly Glu Ala Val Thr Ala Ala Glu Phe Arg Ile Tyr Lys Val Pro Ser Ile His
            (20)                                (30)

CTG CTC AAC AGG ACC CTC CAC GTC AGC ATG TTC CAG GTG GTC CAG GAG CAG TCC
Leu Leu Asn Arg Thr Leu His Val Ser Met Phe Gln Val Val Gln Glu Gln Ser
                (40)                                    (50)

AAC AGG GAG TCT GAC TTG TTC TTT TTG GAT CTT CAG ACG CTC CGA GCT GGA GAC
Asn Arg Glu Ser Asp Leu Phe Phe Leu Asp Leu Gln Thr Leu Arg Ala Gly Asp
                        (60)                                        (70)

GAG GGC TGG CTG GTG CTG GAT GTC ACA GCA GCC AGT GAC TGC TGG TTG CTG AAG
Glu Gly Typ Leu Val Leu Asp Val Thr Ala Ala Ser Asp Cyc Trp Leu Leu Lys
                                (80)

CGT CAC AAG GAC CTG GGA CTC CGC CTC TAT GTG GAG ACT GAG GAT GGG CAC AGC
Arg His Lys Asp Leu Gly Lue Arg Leu Tyr Val Glu Thr Glu Asp Gly His Ser
        (90)                                (100)

GTG GAT CCT GGC CTG GCC GGC CTG CTG GGT CAA CGG GCC CCA CGC TCC CAA CAG
Val Asp Pro Gly Leu Ala Gly Leu Leu Gly Gln Arg Ala Pro Arg Ser Gln Gln
            (110)                               (120)

CCT TTC GTG GTC ACT TTC TTC AGG GCC AGT CCG AGT CCC ATC CGC ACC CCT CGG
Pro Phe Val Val Thr Phe Phe Arg Ala Ser Pro Ser Pro Ile Arg Thr Pro Arg
                    (130)                               (140)

GCA GTG AGG CCA CTG AGG AGG AGG CAG CCG AAG AAA AGC AAC GAG CTG CCG CAG
Ala Val Arg Pro Leu Arg Arg Arg Gln Pro Lys Lys Ser Asn Glu Leu Pro Gln
                            (150)                                   (160)

GCC AAC CGA CTC CCA GGG ATC TTT GAT GAC GTC CAC GGC TCC CAC GGC CGG CAG
Ala Asn Arg Leu Pro Gly Ile Phe Asp Asp Val His Gly Ser His Gly Arg Gln
                            (170)

GTC TGC CGT CGG CAC GAG CTC TAC GTC AGC TTC CAG GAC CTT GGC TGG CTG GAC
Val Cys Arg Arg His Glu Leu Tyr Val Ser Phe Gln Asp Leu Gly Trp Leu Asp
    (180)                                       (190)

TGG GTC ATC GCC CCC CAA GGC TAC TCA GCC TAT TAC TGT GAG GGG GAG TGC TCC
Trp Val Ile Ala Pro Gln Gly Tyr Ser Ala Tyr Tyr Cys Glu Gly Glu Cys Ser
            (200)                               (210)

TTC CCG CTG GAC TCC TGC ATG AAC GCC ACC AAC CAC GCC ATC CTG CAG TCC CTG
Phe Pro Leu Asp Ser Cys Met Asn Ala Thr Asn His Ala Ile Leu Gln Ser Leu
                (220)                               (230)
```

*FIG. 6*

```
GTG CAC CTG ATG AAG CCA AAC GCA GTC CCC AAG GCG TGC TGT GCA CCC ACC AAG
Val His Leu Met Lys Pro Asn Ala Val Pro Lys Ala Cys Cys Ala Pro Thr Lys
                            (240)                                  (250)

CTG AGC GCC ACC TCT GTG CTC TAC TAT GAC AGC AGC AAC AAC GTC ATC CTG CGC
Leu Ser Ala Thr Ser Val Leu Tyr Tyr Asp Ser Ser Asn Asn Val Ile Leu Arg
                                    (260)

AAG CAC CGC AAC ATG GTG GTC AAG GCC TGC GGC TGC CAC TGAGTCAGCCCGCCCAGC
Lys His Arg Asn Met Val Val Lys Ala Cys Gly Cys His
    (270)                                   (280)

CCTACTGCAGCCACCCTTCTCATCTGGATCGGGCCCTGCAGAGGCAGAAAACCCTTAAATGCTGTCACAG

CTCAAGCAGGAGTGTCAGGGGCCCTCACTCTCGGTGCCTACTTCCTGTCAGGCTTCTGGGAATTC
```

FIG. 6 (CON'T)

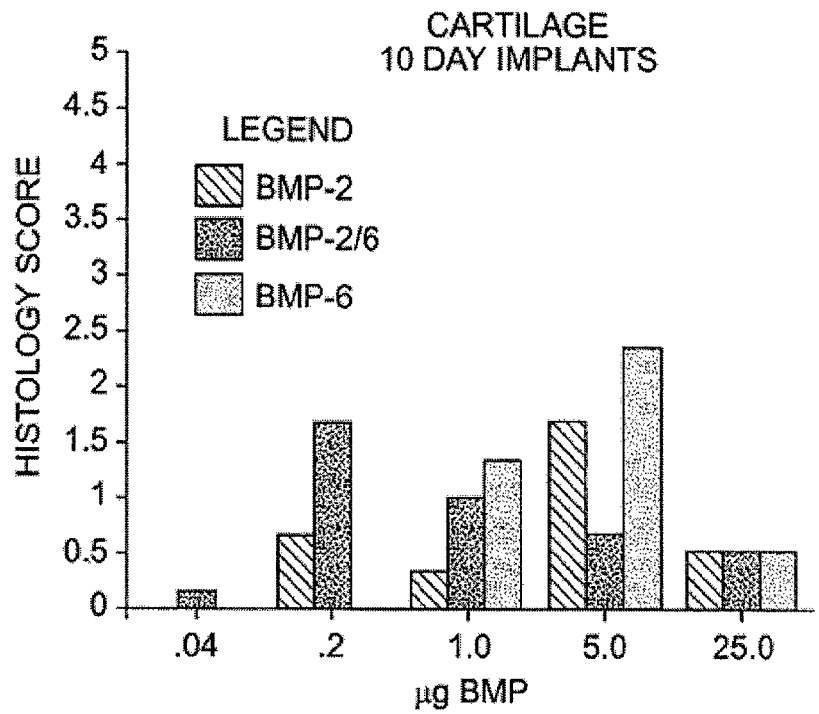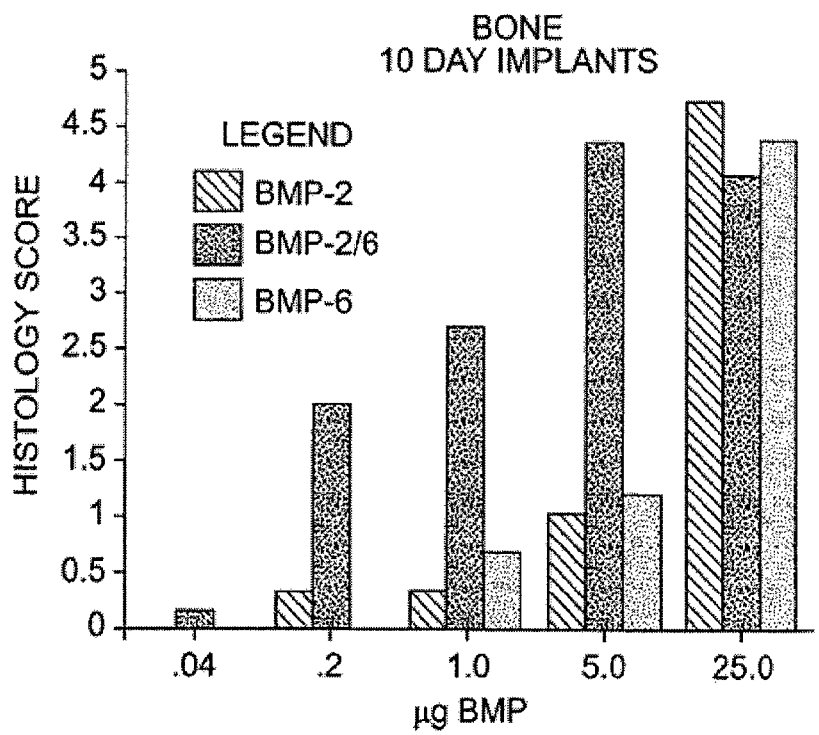
FIG. 12

SEQUENCE LISTING

<160> NUMBER OF SEQ ID NOS: 34

<210> SEQ ID NO 1
<211> LENGTH: 1607
<212> TYPE: DNA
<213> ORGANISM: Homo sapiens
<220> FEATURE:
<221> NAME/KEY: CDS
<222> LOCATION: (356)..(1543)

<400> SEQUENCE: 1

```
gtcgactcta gagtgtgtgt cagcacttgg ctggggactt cttgaacttg cagggagaat      60
aacttgcgca ccccactttg cgccggtgcc tttgccccag cggagcctgc ttcgccatct     120
ccgagcccca ccgcccctcc actcctcggc cttgcccgac actgagacgc tgttcccagc     180
gtgaaaagag agactgcgcg gccggcaccc gggagaagga ggaggcaaag aaaaggaacg     240
gacattcggt ccttgcgcca ggtcctttga ccagagtttt ccatgtgga cgctctttca     300 atggacgtgt ccccgcgtgc ttcttagacg gactgcggtc tcctaaaggt cgacc atg     358
                                                              Met
                                                                1 gtg gcc ggg acc cgc tgt ctt cta gcg ttg ctg ctt ccc cag gtc ctc       406
Val Ala Gly Thr Arg Cys Leu Leu Ala Leu Leu Leu Pro Gln Val Leu
          5                  10                  15 ctg ggc ggc gcg gct ggc ctc gtt ccg gag ctg ggc cgc agg aag ttc       454
Leu Gly Gly Ala Ala Gly Leu Val Pro Glu Leu Gly Arg Arg Lys Phe
     20                  25                  30 gcg gcg gcg tcg tcg ggc cgc ccc tca tcc cag ccc tct gac gag gtc       502
Ala Ala Ala Ser Ser Gly Arg Pro Ser Ser Gln Pro Ser Asp Glu Val
 35                  40                  45 ctg agc gag ttc gag ttg cgg ctg ctc agc atg ttc ggc ctg aaa cag       550
Leu Ser Glu Phe Glu Leu Arg Leu Leu Ser Met Phe Gly Leu Lys Gln
 50                  55                  60                  65 aga ccc acc ccc agc agg gac gcc gtg gtg ccc ccc tac atg cta gac       598
Arg Pro Thr Pro Ser Arg Asp Ala Val Val Pro Pro Tyr Met Leu Asp
             70                  75                  80 ctg tat cgc agg cac tca ggt cag ccg ggc tca ccc gcc cca gac cac       646
Leu Tyr Arg Arg His Ser Gly Gln Pro Gly Ser Pro Ala Pro Asp His
         85                  90                  95 cgg ttg gag agg gca gcc agc cga gcc aac act gtg cgc agc ttc cac       694
Arg Leu Glu Arg Ala Ala Ser Arg Ala Asn Thr Val Arg Ser Phe His
    100                 105                 110 cat gaa gaa tct ttg gaa gaa cta cca gaa acg agt ggg aaa aca acc       742
His Glu Glu Ser Leu Glu Glu Leu Pro Glu Thr Ser Gly Lys Thr Thr
    115                 120                 125 cgg aga ttc ttc ttt aat tta agt tct atc ccc acg gag gag ttt atc       790
Arg Arg Phe Phe Phe Asn Leu Ser Ser Ile Pro Thr Glu Glu Phe Ile
130                 135                 140                 145 acc tca gca gag ctt cag gtt ttc cga gaa cag atg caa gat gct tta       838
Thr Ser Ala Glu Leu Gln Val Phe Arg Glu Gln Met Gln Asp Ala Leu
                150                 155                 160 gga aac aat agc agt ttc cat cac cga att aat att tat gaa atc ata       886
Gly Asn Asn Ser Ser Phe His His Arg Ile Asn Ile Tyr Glu Ile Ile
            165                 170                 175 aaa cct gca aca gcc aac tcg aaa ttc ccc gtg acc aga ctt ttg gac       934
Lys Pro Ala Thr Ala Asn Ser Lys Phe Pro Val Thr Arg Leu Leu Asp
        180                 185                 190 acc agg ttg gtg aat cag aat gca agc agg tgg gaa act ttt gat gtc       982
Thr Arg Leu Val Asn Gln Asn Ala Ser Arg Trp Glu Thr Phe Asp Val
```

```
                195                 200                 205
acc ccc gct gtg atg cgg tgg act gca cag gga cac gcc aac cat gga    1030
Thr Pro Ala Val Met Arg Trp Thr Ala Gln Gly His Ala Asn His Gly
210                 215                 220                 225 ttc gtg gtg gaa gtg gcc cac ttg gag gag aaa caa ggt gtc tcc aag    1078
Phe Val Val Glu Val Ala His Leu Glu Glu Lys Gln Gly Val Ser Lys
                230                 235                 240 aga cat gtt agg ata agc agg tct ttg cac caa gat gaa cac agc tgg    1126
Arg His Val Arg Ile Ser Arg Ser Leu His Gln Asp Glu His Ser Trp
245                 250                 255 tca cag ata agg cca ttg cta gta act ttt ggc cat gat gga aaa ggg    1174
Ser Gln Ile Arg Pro Leu Leu Val Thr Phe Gly His Asp Gly Lys Gly
                260                 265                 270 cat cct ctc cac aaa aga gaa aaa cgt caa gcc aaa cac aaa cag cgg    1222
His Pro Leu His Lys Arg Glu Lys Arg Gln Ala Lys His Lys Gln Arg
275                 280                 285 aaa cgc ctt aag tcc agc tgt aag aga cac cct ttg tac gtg gac ttc    1270
Lys Arg Leu Lys Ser Ser Cys Lys Arg His Pro Leu Tyr Val Asp Phe
290                 295                 300                 305 agt gac gtg ggg tgg aat gac tgg att gtg gct ccc ccg ggg tat cac    1318
Ser Asp Val Gly Trp Asn Asp Trp Ile Val Ala Pro Pro Gly Tyr His
                310                 315                 320 gcc ttt tac tgc cac gga gaa tgc cct ttt cct ctg gct gat cat ctg    1366
Ala Phe Tyr Cys His Gly Glu Cys Pro Phe Pro Leu Ala Asp His Leu
325                 330                 335 aac tcc act aat cat gcc att gtt cag acg ttg gtc aac tct gtt aac    1414
Asn Ser Thr Asn His Ala Ile Val Gln Thr Leu Val Asn Ser Val Asn
                340                 345                 350 tct aag att cct aag gca tgc tgt gtc ccg aca gaa ctc agt gct atc    1462
Ser Lys Ile Pro Lys Ala Cys Cys Val Pro Thr Glu Leu Ser Ala Ile
355                 360                 365 tcg atg ctg tac ctt gac gag aat gaa aag gtt gta tta aag aac tat    1510
Ser Met Leu Tyr Leu Asp Glu Asn Glu Lys Val Val Leu Lys Asn Tyr
370                 375                 380                 385 cag gac atg gtt gtg gag ggt tgt ggg tgt cgc tagtacagca aaattaaata  1563
Gln Asp Met Val Val Glu Gly Cys Gly Cys Arg
                390                 395 cataaatata tatatatata tatattttag aaaaagaaa aaaa                    1607

<210> SEQ ID NO 2
<211> LENGTH: 396
<212> TYPE: PRT
<213> ORGANISM: Homo sapiens

<400> SEQUENCE: 2

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
```

-continued

```
                100                 105                 110
His His Glu Glu Ser Leu Glu Leu Pro Glu Thr Ser Gly Lys Thr
            115                 120                 125

Thr Arg Arg Phe Phe Phe Asn Leu Ser Ser Ile Pro Thr Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Thr Phe Asp
            195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 3
<211> LENGTH: 1954
<212> TYPE: DNA
<213> ORGANISM: Homo sapiens
<220> FEATURE:
<221> NAME/KEY: CDS
<222> LOCATION: (403)..(1626)

<400> SEQUENCE: 3
ctctagaggg cagaggagga gggagggagg gaaggagcgc ggagcccggc ccggaagcta      60
ggtgagtgtg gcatccgagc tgagggacgc gagcctgaga cgccgctgct gctccggctg    120
agtatctagc ttgtctcccc gatgggattc ccgtccaagc tatctcgagc ctgcagcgcc    180
acagtccccg gccctcgccc aggttcactg caaccgttca gaggtcccca ggagctgctg    240
ctggcgagcc cgctactgca gggacctatg gagccattcc gtagtgccat cccgagcaac    300
gcactgctgc agcttccctg agcctttcca gcaagtttgt tcaagattgg ctgtcaagaa    360
```

-continued

| | |
|---|---|
| tcatggactg ttattatatg ccttgttttc tgtcaagaca cc atg att cct ggt<br>                                                                                                                                                                                                                              Met Ile Pro Gly<br>                                                                                                                                                                                                                                1 | 414 |

```
aac cga atg ctg atg gtc gtt tta tta tgc caa gtc ctg cta gga ggc       462
Asn Arg Met Leu Met Val Val Leu Leu Cys Gln Val Leu Leu Gly Gly
 5              10                  15                  20 gcg agc cat gct agt ttg ata cct gag acg ggg aag aaa aaa gtc gcc       510
Ala Ser His Ala Ser Leu Ile Pro Glu Thr Gly Lys Lys Lys Val Ala
             25                  30                  35 gag att cag ggc cac gcg gga gga cgc cgc tca ggg cag agc cat gag       558
Glu Ile Gln Gly His Ala Gly Gly Arg Arg Ser Gly Gln Ser His Glu
 40                  45                  50 ctc ctg cgg gac ttc gag gcg aca ctt ctg cag atg ttt ggg ctg cgc       606
Leu Leu Arg Asp Phe Glu Ala Thr Leu Leu Gln Met Phe Gly Leu Arg
         55                  60                  65 cgc cgc ccg cag cct agc aag agt gcc gtc att ccg gac tac atg cgg       654
Arg Arg Pro Gln Pro Ser Lys Ser Ala Val Ile Pro Asp Tyr Met Arg
 70                  75                  80 gat ctt tac cgg ctt cag tct ggg gag gag gag gaa gag cag atc cac       702
Asp Leu Tyr Arg Leu Gln Ser Gly Glu Glu Glu Glu Glu Gln Ile His
85                  90                  95                 100 agc act ggt ctt gag tat cct gag cgc ccg gcc agc cgg gcc aac acc       750
Ser Thr Gly Leu Glu Tyr Pro Glu Arg Pro Ala Ser Arg Ala Asn Thr
             105                 110                 115 gtg agg agc ttc cac cac gaa gaa cat ctg gag aac atc cca ggg acc       798
Val Arg Ser Phe His His Glu Glu His Leu Glu Asn Ile Pro Gly Thr
 120                 125                 130 agt gaa aac tct gct ttt cgt ttc ctc ttt aac ctc agc agc atc cct       846
Ser Glu Asn Ser Ala Phe Arg Phe Leu Phe Asn Leu Ser Ser Ile Pro
         135                 140                 145 gag aac gag gtg atc tcc tct gca gag ctt cgg ctc ttc cgg gag cag       894
Glu Asn Glu Val Ile Ser Ser Ala Glu Leu Arg Leu Phe Arg Glu Gln
 150                 155                 160 gtg gac cag ggc cct gat tgg gaa agg ggc ttc cac cgt ata aac att       942
Val Asp Gln Gly Pro Asp Trp Glu Arg Gly Phe His Arg Ile Asn Ile
165                 170                 175                 180 tat gag gtt atg aag ccc cca gca gaa gtg gtg cct ggg cac ctc atc       990
Tyr Glu Val Met Lys Pro Pro Ala Glu Val Val Pro Gly His Leu Ile
             185                 190                 195 aca cga cta ctg gac acg aga ctg gtc cac cac aat gtg aca cgg tgg      1038
Thr Arg Leu Leu Asp Thr Arg Leu Val His His Asn Val Thr Arg Trp
 200                 205                 210 gaa act ttt gat gtg agc cct gcg gtc ctt cgc tgg acc cgg gag aag      1086
Glu Thr Phe Asp Val Ser Pro Ala Val Leu Arg Trp Thr Arg Glu Lys
         215                 220                 225 cag cca aac tat ggg cta gcc att gag gtg act cac ctc cat cag act      1134
Gln Pro Asn Tyr Gly Leu Ala Ile Glu Val Thr His Leu His Gln Thr
 230                 235                 240 cgg acc cac cag ggc cag cat gtc agg att agc cga tcg tta cct caa      1182
Arg Thr His Gln Gly Gln His Val Arg Ile Ser Arg Ser Leu Pro Gln
245                 250                 255                 260 ggg agt ggg aat tgg gcc cag ctc cgg ccc ctc ctg gtc acc ttt ggc      1230
Gly Ser Gly Asn Trp Ala Gln Leu Arg Pro Leu Leu Val Thr Phe Gly
             265                 270                 275 cat gat ggc cgg ggc cat gcc ttg acc cga cgc cgg agg gcc aag cgt      1278
His Asp Gly Arg Gly His Ala Leu Thr Arg Arg Arg Arg Ala Lys Arg
 280                 285                 290 agc cct aag cat cac tca cag cgg gcc agg aag aag aat aag aac tgc      1326
Ser Pro Lys His His Ser Gln Arg Ala Arg Lys Lys Asn Lys Asn Cys
         295                 300                 305
```

-continued

```
cgg cgc cac tcg ctc tat gtg gac ttc agc gat gtg ggc tgg aat gac    1374
Arg Arg His Ser Leu Tyr Val Asp Phe Ser Asp Val Gly Trp Asn Asp
    310                 315                 320 tgg att gtg gcc cca cca ggc tac cag gcc ttc tac tgc cat ggg gac    1422
Trp Ile Val Ala Pro Pro Gly Tyr Gln Ala Phe Tyr Cys His Gly Asp
325                 330                 335                 340 tgc ccc ttt cca ctg gct gac cac ctc aac tca acc aac cat gcc att    1470
Cys Pro Phe Pro Leu Ala Asp His Leu Asn Ser Thr Asn His Ala Ile
                345                 350                 355 gtg cag acc ctg gtc aat tct gtc aat tcc agt atc ccc aaa gcc tgt    1518
Val Gln Thr Leu Val Asn Ser Val Asn Ser Ser Ile Pro Lys Ala Cys
            360                 365                 370 tgt gtg ccc act gaa ctg agt gcc atc tcc atg ctg tac ctg gat gag    1566
Cys Val Pro Thr Glu Leu Ser Ala Ile Ser Met Leu Tyr Leu Asp Glu
        375                 380                 385 tat gat aag gtg gta ctg aaa aat tat cag gag atg gta gta gag gga    1614
Tyr Asp Lys Val Val Leu Lys Asn Tyr Gln Glu Met Val Val Glu Gly
    390                 395                 400 tgt ggg tgc cgc tgagatcagg cagtccttga ggatagacag atatacacac        1666
Cys Gly Cys Arg
405 cacacacaca caccacatac accacacaca cacgttccca tccactcacc cacacactac    1726 acagactgct tccttatagc tggactttta tttaaaaaaa aaaaaaaaaa aatggaaaaa    1786 atccctaaac attcccttg accttattta tgactttacg tgcaaatgtt ttgaccatat    1846 tgatcatata ttttgacaaa atatatttat aactacgtat taaaagaaaa aaataaaatg    1906 agtcattatt ttaaaaaaaa aaaaaaaact ctagagtcga cggaattc                1954
```

<210> SEQ ID NO 4
<211> LENGTH: 408
<212> TYPE: PRT
<213> ORGANISM: Homo sapiens

<400> SEQUENCE: 4

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175
```

-continued

```
Arg Ile Asn Ile Tyr Glu Val Met Lys Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

<210> SEQ ID NO 5
<211> LENGTH: 1448
<212> TYPE: DNA
<213> ORGANISM: Homo sapiens
<220> FEATURE:
<221> NAME/KEY: CDS
<222> LOCATION: (97)..(1389)

<400> SEQUENCE: 5

```
gtgaccgagc ggcgcggacg gccgcctgcc ccctctgcca cctggggcgg tgcgggcccg      60
gagcccggag cccgggtagc gcgtagagcc ggcgcg atg cac gtg cgc tca ctg      114
                                        Met His Val Arg Ser Leu
                                          1               5 cga gct gcg gcg ccg cac agc ttc gtg gcg ctc tgg gca ccc ctg ttc      162
Arg Ala Ala Ala Pro His Ser Phe Val Ala Leu Trp Ala Pro Leu Phe
            10                  15                  20 ctg ctg cgc tcc gcc ctg gcc gac ttc agc ctg gac aac gag gtg cac      210
Leu Leu Arg Ser Ala Leu Ala Asp Phe Ser Leu Asp Asn Glu Val His
        25                  30                  35 tcg agc ttc atc cac cgg cgc ctc cgc agc cag gag cgg cgg gag atg      258
Ser Ser Phe Ile His Arg Arg Leu Arg Ser Gln Glu Arg Arg Glu Met
    40                  45                  50 cag cgc gag atc ctc tcc att ttg ggc ttg ccc cac cgc ccg cgc ccg      306
Gln Arg Glu Ile Leu Ser Ile Leu Gly Leu Pro His Arg Pro Arg Pro
55                  60                  65                  70
```

|  |  |
|---|---|
| cac ctc cag ggc aag cac aac tcg gca ccc atg ttc atg ctg gac ctg<br>His Leu Gln Gly Lys His Asn Ser Ala Pro Met Phe Met Leu Asp Leu<br>                75               80                  85 | 354 |
| tac aac gcc atg gcg gtg gag gag ggc ggc ggg ccc ggc ggc cag ggc<br>Tyr Asn Ala Met Ala Val Glu Glu Gly Gly Gly Pro Gly Gly Gln Gly<br>    90                  95                  100 | 402 |
| ttc tcc tac ccc tac aag gcc gtc ttc agt acc cag ggc ccc cct ctg<br>Phe Ser Tyr Pro Tyr Lys Ala Val Phe Ser Thr Gln Gly Pro Pro Leu<br>        105                110              115 | 450 |
| gcc agc ctg caa gat agc cat ttc ctc acc gac gcc gac atg gtc atg<br>Ala Ser Leu Gln Asp Ser His Phe Leu Thr Asp Ala Asp Met Val Met<br>120                  125                130 | 498 |
| agc ttc gtc aac ctc gtg gaa cat gac aag gaa ttc ttc cac cca cgc<br>Ser Phe Val Asn Leu Val Glu His Asp Lys Glu Phe Phe His Pro Arg<br>135                  140              145              150 | 546 |
| tac cac cat cga gag ttc cgg ttt gat ctt tcc aag atc cca gaa ggg<br>Tyr His His Arg Glu Phe Arg Phe Asp Leu Ser Lys Ile Pro Glu Gly<br>                155              160              165 | 594 |
| gaa gct gtc acg gca gcc gaa ttc cgg atc tac aag gac tac atc cgg<br>Glu Ala Val Thr Ala Ala Glu Phe Arg Ile Tyr Lys Asp Tyr Ile Arg<br>            170              175              180 | 642 |
| gaa cgc ttc gac aat gag acg ttc cgg atc agc gtt tat cag gtg ctc<br>Glu Arg Phe Asp Asn Glu Thr Phe Arg Ile Ser Val Tyr Gln Val Leu<br>        185                190              195 | 690 |
| cag gag cac ttg ggc agg gaa tcg gat ctc ttc ctg ctc gac agc cgt<br>Gln Glu His Leu Gly Arg Glu Ser Asp Leu Phe Leu Leu Asp Ser Arg<br>    200                  205              210 | 738 |
| acc ctc tgg gcc tcg gag gag ggc tgg ctg gtg ttt gac atc aca gcc<br>Thr Leu Trp Ala Ser Glu Glu Gly Trp Leu Val Phe Asp Ile Thr Ala<br>215                  220              225              230 | 786 |
| acc agc aac cac tgg gtg gtc aat ccg cgg cac aac ctg ggc ctg cag<br>Thr Ser Asn His Trp Val Val Asn Pro Arg His Asn Leu Gly Leu Gln<br>                235              240              245 | 834 |
| ctc tcg gtg gag acg ctg gat ggg cag agc atc aac ccc aag ttg gcg<br>Leu Ser Val Glu Thr Leu Asp Gly Gln Ser Ile Asn Pro Lys Leu Ala<br>            250              255              260 | 882 |
| ggc ctg att ggg cgg cac ggg ccc cag aac aag cag ccc ttc atg gtg<br>Gly Leu Ile Gly Arg His Gly Pro Gln Asn Lys Gln Pro Phe Met Val<br>        265                270              275 | 930 |
| gct ttc ttc aag gcc acg gag gtc cac ttc cgc agc atc cgg tcc acg<br>Ala Phe Phe Lys Ala Thr Glu Val His Phe Arg Ser Ile Arg Ser Thr<br>280                  285              290 | 978 |
| ggg agc aaa cag cgc agc cag aac cgc tcc aag acg ccc aag aac cag<br>Gly Ser Lys Gln Arg Ser Gln Asn Arg Ser Lys Thr Pro Lys Asn Gln<br>295                  300              305              310 | 1026 |
| gaa gcc ctg cgg atg gcc aac gtg gca gag aac agc agc agc gac cag<br>Glu Ala Leu Arg Met Ala Asn Val Ala Glu Asn Ser Ser Ser Asp Gln<br>            315              320              325 | 1074 |
| agg cag gcc tgt aag aag cac gag ctg tat gtc agc ttc cga gac ctg<br>Arg Gln Ala Cys Lys Lys His Glu Leu Tyr Val Ser Phe Arg Asp Leu<br>        330                335              340 | 1122 |
| ggc tgg cag gac tgg atc atc gcg cct gaa ggc tac gcc gcc tac tac<br>Gly Trp Gln Asp Trp Ile Ile Ala Pro Glu Gly Tyr Ala Ala Tyr Tyr<br>    345                350              355 | 1170 |
| tgt gag ggg gag tgt gcc ttc cct ctg aac tcc tac atg aac gcc acc<br>Cys Glu Gly Glu Cys Ala Phe Pro Leu Asn Ser Tyr Met Asn Ala Thr<br>360                  365              370 | 1218 |
| aac cac gcc atc gtg cag acg ctg gtc cac ttc atc aac ccg gaa acg<br>Asn His Ala Ile Val Gln Thr Leu Val His Phe Ile Asn Pro Glu Thr<br>375                  380              385              390 | 1266 |

```
gtg ccc aag ccc tgc tgt gcg ccc acg cag ctc aat gcc atc tcc gtc   1314
Val Pro Lys Pro Cys Cys Ala Pro Thr Gln Leu Asn Ala Ile Ser Val
            395                 400                 405 ctc tac ttc gat gac agc tcc aac gtc atc ctg aag aaa tac aga aac   1362
Leu Tyr Phe Asp Asp Ser Ser Asn Val Ile Leu Lys Lys Tyr Arg Asn
            410                 415                 420 atg gtg gtc cgg gcc tgt ggc tgc cac tagctcctcc gagaattcag         1409
Met Val Val Arg Ala Cys Gly Cys His
            425                 430 acccttggg gccaagtttt tctggatcct ccattgctc                         1448

<210> SEQ ID NO 6
<211> LENGTH: 431
<212> TYPE: PRT
<213> ORGANISM: Homo sapiens

<400> SEQUENCE: 6

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300
```

```
Lys Thr Pro Lys Asn Gln Glu Ala Leu Arg Met Ala Asn Val Ala Glu
305                 310                 315                 320

Asn Ser Ser Asp Gln Arg Gln Ala Cys Lys Lys His Glu Leu Tyr
            325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 7
<211> LENGTH: 2923
<212> TYPE: DNA
<213> ORGANISM: Homo sapiens
<220> FEATURE:
<221> NAME/KEY: CDS
<222> LOCATION: (160)..(1701)

<400> SEQUENCE: 7
cgaccatgag agataaggac tgagggccag aaggggaag cgagcccgcc gagaggtggc      60
ggggactgct cacgccaagg ccacagcgg ccgcgctccg gcctcgctcc gccgctccac     120
gcctcgcggg atccgcgggg gcagcccggc cgggcgggg atg ccg ggg ctg ggg      174
                                           Met Pro Gly Leu Gly
                                             1               5 cgg agg gcg cag tgg ctg tgc tgg tgg tgg ggg ctg ctg tgc agc tgc      222
Arg Arg Ala Gln Trp Leu Cys Trp Trp Trp Gly Leu Leu Cys Ser Cys
            10                  15                  20 tgc ggg ccc ccg ccg ctg cgg ccg ccc ttg ccc gct gcc gcg gcc gcc      270
Cys Gly Pro Pro Pro Leu Arg Pro Pro Leu Pro Ala Ala Ala Ala Ala
            25                  30                  35 gcc gcc ggg ggg cag ctg ctg ggg gac ggc ggg agc ccc ggc cgc acg      318
Ala Ala Gly Gly Gln Leu Leu Gly Asp Gly Gly Ser Pro Gly Arg Thr
            40                  45                  50 gag cag ccg ccg ccg tcg ccg cag tcc tcc tcg ggc ttc ctg tac cgg      366
Glu Gln Pro Pro Pro Ser Pro Gln Ser Ser Ser Gly Phe Leu Tyr Arg
    55                  60                  65 cgg ctc aag acg cag gag aag cgg gag atg cag aag gag atc ttg tcg      414
Arg Leu Lys Thr Gln Glu Lys Arg Glu Met Gln Lys Glu Ile Leu Ser
70                  75                  80                  85 gtg ctg ggg ctc ccg cac cgg ccc cgg ccc ctg cac ggc ctc caa cag      462
Val Leu Gly Leu Pro His Arg Pro Arg Pro Leu His Gly Leu Gln Gln
                90                  95                 100 ccg cag ccc ccg gcg ctc cgg cag cag gag gag cag cag cag cag cag      510
Pro Gln Pro Pro Ala Leu Arg Gln Gln Glu Glu Gln Gln Gln Gln Gln
            105                 110                 115 cag ctg cct cgc gga gag ccc cct ccc ggg cga ctg aag tcc gcg ccc      558
Gln Leu Pro Arg Gly Glu Pro Pro Pro Gly Arg Leu Lys Ser Ala Pro
        120                 125                 130 ctc ttc atg ctg gat ctg tac aac gcc ctg tcc gcc gac aac gac gag      606
Leu Phe Met Leu Asp Leu Tyr Asn Ala Leu Ser Ala Asp Asn Asp Glu
    135                 140                 145
```

```
                                                        -continued gac ggg gcg tcg gag ggg gag agg cag cag tcc tgg ccc cac gaa gca        654
Asp Gly Ala Ser Glu Gly Glu Arg Gln Gln Ser Trp Pro His Glu Ala
150                 155                 160                 165 gcc agc tcg tcc cag cgt cgg cag ccg ccc ccg ggc gcg cac ccg            702
Ala Ser Ser Ser Gln Arg Arg Gln Pro Pro Pro Gly Ala Ala His Pro
                170                 175                 180 ctc aac cgc aag agc ctt ctg gcc ccc gga tct ggc agc ggc ggc gcg        750
Leu Asn Arg Lys Ser Leu Leu Ala Pro Gly Ser Gly Ser Gly Gly Ala
            185                 190                 195 tcc cca ctg acc agc gcg cag gac agc gcc ttc ctc aac gac gcg gac        798
Ser Pro Leu Thr Ser Ala Gln Asp Ser Ala Phe Leu Asn Asp Ala Asp
        200                 205                 210 atg gtc atg agc ttt gtg aac ctg gtg gag tac gac aag gag ttc tcc        846
Met Val Met Ser Phe Val Asn Leu Val Glu Tyr Asp Lys Glu Phe Ser
    215                 220                 225 cct cgt cag cga cac cac aaa gag ttc aag ttc aac tta tcc cag att        894
Pro Arg Gln Arg His His Lys Glu Phe Lys Phe Asn Leu Ser Gln Ile
230                 235                 240                 245 cct gag ggt gag gtg gtg acg gct gca gaa ttc cgc atc tac aag gac        942
Pro Glu Gly Glu Val Val Thr Ala Ala Glu Phe Arg Ile Tyr Lys Asp
                250                 255                 260 tgt gtt atg ggg agt ttt aaa aac caa act ttt ctt atc agc att tat        990
Cys Val Met Gly Ser Phe Lys Asn Gln Thr Phe Leu Ile Ser Ile Tyr
            265                 270                 275 caa gtc tta cag gag cat cag cac aga gac tct gac ctg ttt ttg ttg       1038
Gln Val Leu Gln Glu His Gln His Arg Asp Ser Asp Leu Phe Leu Leu
        280                 285                 290 gac acc cgt gta gta tgg gcc tca gaa gaa ggc tgg ctg gaa ttt gac       1086
Asp Thr Arg Val Val Trp Ala Ser Glu Glu Gly Trp Leu Glu Phe Asp
    295                 300                 305 atc acg gcc act agc aat ctg tgg gtt gtg act cca cag cat aac atg       1134
Ile Thr Ala Thr Ser Asn Leu Trp Val Val Thr Pro Gln His Asn Met
310                 315                 320                 325 ggg ctt cag ctg agc gtg gtg aca agg gat gga gtc cac gtc cac ccc       1182
Gly Leu Gln Leu Ser Val Val Thr Arg Asp Gly Val His Val His Pro
                330                 335                 340 cga gcc gca ggc ctg gtg ggc aga gac ggc cct tac gat aag cag ccc       1230
Arg Ala Ala Gly Leu Val Gly Arg Asp Gly Pro Tyr Asp Lys Gln Pro
            345                 350                 355 ttc atg gtg gct ttc ttc aaa gtg agt gag gtc cac gtg cgc acc acc       1278
Phe Met Val Ala Phe Phe Lys Val Ser Glu Val His Val Arg Thr Thr
        360                 365                 370 agg tca gcc tcc agc cgg cgc cga caa cag agt cgt aat cgc tct acc       1326
Arg Ser Ala Ser Ser Arg Arg Arg Gln Gln Ser Arg Asn Arg Ser Thr
    375                 380                 385 cag tcc cag gac gtg gcg cgg gtc tcc agt gct tca gat tac aac agc       1374
Gln Ser Gln Asp Val Ala Arg Val Ser Ser Ala Ser Asp Tyr Asn Ser
390                 395                 400                 405 agt gaa ttg aaa aca gcc tgc agg aag cat gag ctg tat gtg agt ttc       1422
Ser Glu Leu Lys Thr Ala Cys Arg Lys His Glu Leu Tyr Val Ser Phe
                410                 415                 420 caa gac ctg gga tgg cag gac tgg atc att gca ccc aag ggc tat gct       1470
Gln Asp Leu Gly Trp Gln Asp Trp Ile Ile Ala Pro Lys Gly Tyr Ala
            425                 430                 435 gcc aat tac tgt gat gga gaa tgc tcc ttc cca ctc aac gca cac atg       1518
Ala Asn Tyr Cys Asp Gly Glu Cys Ser Phe Pro Leu Asn Ala His Met
        440                 445                 450 aat gca acc aac cac gcg att gtg cag acc ttg gtt cac ctt atg aac       1566
Asn Ala Thr Asn His Ala Ile Val Gln Thr Leu Val His Leu Met Asn
```

```
                455                     460                     465
ccc gag tat gtc ccc aaa ccg tgc tgt gcg cca act aag cta aat gcc   1614
Pro Glu Tyr Val Pro Lys Pro Cys Cys Ala Pro Thr Lys Leu Asn Ala
470                     475                     480                485 atc tcg gtt ctt tac ttt gat gac aac tcc aat gtc att ctg aaa aaa   1662
Ile Ser Val Leu Tyr Phe Asp Asp Asn Ser Asn Val Ile Leu Lys Lys
                    490                     495                 500 tac agg aat atg gtt gta aga gct tgt gga tgc cac taa ctcgaaacca    1711
Tyr Arg Asn Met Val Val Arg Ala Cys Gly Cys His
            505                     510 gatgctgggg acacacattc tgccttggat tcctagatta catctgcctt aaaaaaacac   1771
ggaagcacag ttggaggtgg gacgatgaga ctttgaaact atctcatgcc agtgccttat   1831
tacccaggaa gattttaaag gacctcatta ataatttgct cacttggtaa atgacgtgag   1891
tagttgttgg tctgtagcaa gctgagtttg gatgtctgta gcataaggtc tggtaactgc   1951
agaaacataa ccgtgaagct cttcctaccc tcctccccca aaaacccacc aaaattagtt   2011
ttagctgtag atcaagctat ttggggtgtt tgttagtaaa tagggaaaat aatctcaaag   2071
gagttaaatg tattcttggc taaaggatca gctggttcag tactgtctat caaaggtaga   2131
ttttacagag aacagaaatc ggggaagtgg ggggaacgcc tctgttcagt tcattcccag   2191
aagtccacag gacgcacagc ccaggccaca gccagggctc cacggggcgc ccttgtctca   2251
gtcattgctg ttgtatgttc gtgctggagt tttgttggtg tgaaaataca cttatttcag   2311
ccaaaacata ccatttctac acctcaatcc tccatttgct gtactctttg ctagtaccaa   2371
aagtagactg attacactga ggtgaggcta caaggggtgt gtaaccgtgt aacacgtgaa   2431
ggcagtgctc acctcttctt taccagaacg gttctttgac cagcacatta acttctggac   2491
tgccggctct agtaccttt cagtaaagtg gttctctgcc tttttactat acagcatacc   2551
acgccacagg gttagaacca acgaagaaaa taaaatgagg gtgcccagct tataagaatg   2611
gtgttagggg gatgagcatg ctgtttatga acggaaatca tgatttccct gtagaaagtg   2671
aggctcagat taaattttag aatattttct aaatgtcttt ttcacaatca tgtgactggg   2731
aaggcaattt catactaaac tgattaaata atacattat aatctacaac tgtttgcact   2791
tacagctttt tttgtaaata taaactataa tttattgtct atttatatc tgttttgctg   2851
tggcgttggg ggggggccg ggcttttggg ggggggggtt tgtttggggg gtgtcgtggt    2911
gtgggcgggc gg                                                      2923

<210> SEQ ID NO 8
<211> LENGTH: 513
<212> TYPE: PRT
<213> ORGANISM: Homo sapiens

<400> SEQUENCE: 8

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Ala Gly Gly Gln Leu Leu Gly Asp Gly Gly
        35                  40                  45

Ser Pro Gly Arg Thr Glu Gln Pro Pro Ser Pro Gln Ser Ser
    50                  55                  60

Gly Phe Leu Tyr Arg Arg Leu Lys Thr Gln Glu Lys Arg Glu Met Gln
65                  70                  75                  80
```

```
Lys Glu Ile Leu Ser Val Leu Gly Leu Pro His Arg Pro Arg Pro Leu
                85                  90                  95
His Gly Leu Gln Gln Pro Gln Pro Pro Ala Leu Arg Gln Gln Glu Glu
            100                 105                 110
Gln Gln Gln Gln Gln Leu Pro Arg Gly Glu Pro Pro Gly Arg
        115                 120                 125
Leu Lys Ser Ala Pro Leu Phe Met Leu Asp Leu Tyr Asn Ala Leu Ser
    130                 135                 140
Ala Asp Asn Asp Glu Asp Gly Ala Ser Glu Gly Glu Arg Gln Gln Ser
145                 150                 155                 160
Trp Pro His Glu Ala Ser Ser Ser Gln Arg Arg Gln Pro Pro Pro
                165                 170                 175
Gly Ala Ala His Pro Leu Asn Arg Lys Ser Leu Leu Ala Pro Gly Ser
            180                 185                 190
Gly Ser Gly Gly Ala Ser Pro Leu Thr Ser Ala Gln Asp Ser Ala Phe
        195                 200                 205
Leu Asn Asp Ala Asp Met Val Met Ser Phe Val Asn Leu Val Glu Tyr
    210                 215                 220
Asp Lys Glu Phe Ser Pro Arg Gln Arg His His Lys Glu Phe Lys Phe
225                 230                 235                 240
Asn Leu Ser Gln Ile Pro Glu Gly Glu Val Val Thr Ala Ala Glu Phe
                245                 250                 255
Arg Ile Tyr Lys Asp Cys Val Met Gly Ser Phe Lys Asn Gln Thr Phe
            260                 265                 270
Leu Ile Ser Ile Tyr Gln Val Leu Gln Glu His Gln His Arg Asp Ser
        275                 280                 285
Asp Leu Phe Leu Leu Asp Thr Arg Val Val Trp Ala Ser Glu Glu Gly
    290                 295                 300
Trp Leu Glu Phe Asp Ile Thr Ala Thr Ser Asn Leu Trp Val Val Thr
305                 310                 315                 320
Pro Gln His Asn Met Gly Leu Gln Leu Ser Val Val Thr Arg Asp Gly
                325                 330                 335
Val His Val His Pro Arg Ala Ala Gly Leu Val Gly Arg Asp Gly Pro
            340                 345                 350
Tyr Asp Lys Gln Pro Phe Met Val Ala Phe Phe Lys Val Ser Glu Val
        355                 360                 365
His Val Arg Thr Thr Arg Ser Ala Ser Ser Arg Arg Arg Gln Gln Ser
    370                 375                 380
Arg Asn Arg Ser Thr Gln Ser Gln Asp Val Ala Arg Val Ser Ser Ala
385                 390                 395                 400
Ser Asp Tyr Asn Ser Ser Glu Leu Lys Thr Ala Cys Arg Lys His Glu
                405                 410                 415
Leu Tyr Val Ser Phe Gln Asp Leu Gly Trp Gln Asp Trp Ile Ile Ala
            420                 425                 430
Pro Lys Gly Tyr Ala Ala Asn Tyr Cys Asp Gly Glu Cys Ser Phe Pro
        435                 440                 445
Leu Asn Ala His Met Asn Ala Thr Asn His Ala Ile Val Gln Thr Leu
    450                 455                 460
Val His Leu Met Asn Pro Glu Tyr Val Pro Lys Pro Cys Cys Ala Pro
465                 470                 475                 480
Thr Lys Leu Asn Ala Ile Ser Val Leu Tyr Phe Asp Asp Asn Ser Asn
                485                 490                 495
Val Ile Leu Lys Lys Tyr Arg Asn Met Val Val Arg Ala Cys Gly Cys
```

His

<210> SEQ ID NO 9
<211> LENGTH: 2153
<212> TYPE: DNA
<213> ORGANISM: Homo sapiens
<220> FEATURE:
<221> NAME/KEY: CDS
<222> LOCATION: (699)..(2063)

<400> SEQUENCE: 9

```
ctggtatatt tgtgcctgct ggaggtggaa ttaacagtaa aaggagaaa gggattgaat      60 ggacttacag gaaggatttc aagtaaattc agggaaacac atttacttga atagtacaac    120
ctagagtatt attttacact aagacgacac aaaagatgtt aaagttatca ccaagctgcc    180
ggacagatat atattccaac accaaggtgc agatcagcat agatctgtga ttcagaaatc    240
aggatttgtt ttggaaagag ctcaagggtt gagaagaact caaaagcaag tgaagattac    300
tttgggaact acagtttatc agaagatcaa cttttgctaa ttcaaatacc aaaggcctga    360
ttatcataaa ttcatatagg aatgcatagg tcatctgatc aaataatatt agccgtcttc    420
tgctacatca atgcagcaaa aactcttaac aactgtggat aattggaaat ctgagtttca    480
gctttcttag aaataactac tcttgacata ttccaaaata tttaaaatag gacaggaaaa    540
tcggtgagga tgttgtgctc agaaatgtca ctgtcatgaa aaataggtaa atttgttttt    600
tcagctactg ggaaactgta cctcctagaa ccttaggttt ttttttttttt aagaggacaa    660 gaaggactaa aaatatcaac ttttgctttt ggacaaaaa atg cat ctg act gta ttt    716
                                             Met His Leu Thr Val Phe
                                              1               5 tta ctt aag ggt att gtg ggt ttc ctc tgg agc tgc tgg gtt cta gtg        764
Leu Leu Lys Gly Ile Val Gly Phe Leu Trp Ser Cys Trp Val Leu Val
             10                  15                  20 ggt tat gca aaa gga ggt ttg gga gac aat cat gtt cac tcc agt ttt        812
Gly Tyr Ala Lys Gly Gly Leu Gly Asp Asn His Val His Ser Ser Phe
         25                  30                  35 att tat aga aga cta cgg aac cac gaa aga cgg gaa ata caa agg gaa        860
Ile Tyr Arg Arg Leu Arg Asn His Glu Arg Arg Glu Ile Gln Arg Glu
     40                  45                  50 att ctc tct atc ttg ggt ttg cct cac aga ccc aga cca ttt tca cct        908
Ile Leu Ser Ile Leu Gly Leu Pro His Arg Pro Arg Pro Phe Ser Pro
 55                  60                  65                  70 gga aaa atg acc aat caa gcg tcc tct gca cct ctc ttt atg ctg gat        956
Gly Lys Met Thr Asn Gln Ala Ser Ser Ala Pro Leu Phe Met Leu Asp
                 75                  80                  85 ctc tac aat gcc gaa gaa aat cct gaa gag tcg gag tac tca gta agg       1004
Leu Tyr Asn Ala Glu Glu Asn Pro Glu Glu Ser Glu Tyr Ser Val Arg
             90                  95                 100 gca tcc ttg gca gaa gag acc aga ggg gca aga aag gga tac cca gcc       1052
Ala Ser Leu Ala Glu Glu Thr Arg Gly Ala Arg Lys Gly Tyr Pro Ala
        105                 110                 115 tct ccc aat ggg tat cct cgt cgc ata cag tta tct cgg acg act cct       1100
Ser Pro Asn Gly Tyr Pro Arg Arg Ile Gln Leu Ser Arg Thr Thr Pro
    120                 125                 130 ctg acc acc cag agt cct cct cta gcc agc ctc cat gat acc aac ttt       1148
Leu Thr Thr Gln Ser Pro Pro Leu Ala Ser Leu His Asp Thr Asn Phe
135                 140                 145                 150 ctg aat gat gct gac atg gtc atg agc ttt gtg aac tta gtt gaa aga       1196
Leu Asn Asp Ala Asp Met Val Met Ser Phe Val Asn Leu Val Glu Arg
```

```
                  155                 160                 165
gac aag gat ttt tct cac cag cga agg cat tac aaa gaa ttt cga ttt      1244
Asp Lys Asp Phe Ser His Gln Arg Arg His Tyr Lys Glu Phe Arg Phe
            170                 175                 180 gat ctt acc caa att cct cat gga gag gca gtg aca gca gct gaa ttc      1292
Asp Leu Thr Gln Ile Pro His Gly Glu Ala Val Thr Ala Ala Glu Phe
        185                 190                 195 cgg ata tac aag gac cgg agc aac aac cga ttt gaa aat gaa aca att      1340
Arg Ile Tyr Lys Asp Arg Ser Asn Asn Arg Phe Glu Asn Glu Thr Ile
    200                 205                 210 aag att agc ata tat caa atc atc aag gaa tac aca aat agg gat gca      1388
Lys Ile Ser Ile Tyr Gln Ile Ile Lys Glu Tyr Thr Asn Arg Asp Ala
215                 220                 225                 230 gat ctg ttc ttg tta gac aca aga aag gcc caa gct tta gat gtg ggt      1436
Asp Leu Phe Leu Leu Asp Thr Arg Lys Ala Gln Ala Leu Asp Val Gly
            235                 240                 245 tgg ctt gtc ttt gat atc act gtg acc agc aat cat tgg gtg att aat      1484
Trp Leu Val Phe Asp Ile Thr Val Thr Ser Asn His Trp Val Ile Asn
        250                 255                 260 ccc cag aat aat ttg ggc tta cag ctc tgt gca gaa aca ggg gat gga      1532
Pro Gln Asn Asn Leu Gly Leu Gln Leu Cys Ala Glu Thr Gly Asp Gly
    265                 270                 275 cgc agt atc aac gta aaa tct gct ggt ctt gtg gga aga cag gga cct      1580
Arg Ser Ile Asn Val Lys Ser Ala Gly Leu Val Gly Arg Gln Gly Pro
280                 285                 290 cag tca aaa caa cca ttc atg gtg gcc ttc ttc aag gcg agt gag gta      1628
Gln Ser Lys Gln Pro Phe Met Val Ala Phe Phe Lys Ala Ser Glu Val
295                 300                 305                 310 ctt ctt cga tcc gtg aga gca gcc aac aaa cga aaa aat caa aac cgc      1676
Leu Leu Arg Ser Val Arg Ala Ala Asn Lys Arg Lys Asn Gln Asn Arg
            315                 320                 325 aat aaa tcc agc tct cat cag gac tcc tcc aga atg tcc agt gtt gga      1724
Asn Lys Ser Ser Ser His Gln Asp Ser Ser Arg Met Ser Ser Val Gly
        330                 335                 340 gat tat aac aca agt gag caa aaa caa gcc tgt aag aag cac gaa ctc      1772
Asp Tyr Asn Thr Ser Glu Gln Lys Gln Ala Cys Lys Lys His Glu Leu
    345                 350                 355 tat gtg agc ttc cgg gat ctg gga tgg cag gac tgg att ata gca cca      1820
Tyr Val Ser Phe Arg Asp Leu Gly Trp Gln Asp Trp Ile Ile Ala Pro
360                 365                 370 gaa gga tac gct gca ttt tat tgt gat gga gaa tgt tct ttt cca ctt      1868
Glu Gly Tyr Ala Ala Phe Tyr Cys Asp Gly Glu Cys Ser Phe Pro Leu
375                 380                 385                 390 aac gcc cat atg aat gcc acc aac cac gct ata gtt cag act ctg gtt      1916
Asn Ala His Met Asn Ala Thr Asn His Ala Ile Val Gln Thr Leu Val
            395                 400                 405 cat ctg atg ttt cct gac cac gta cca aag cct tgt tgt gct cca acc      1964
His Leu Met Phe Pro Asp His Val Pro Lys Pro Cys Cys Ala Pro Thr
        410                 415                 420 aaa tta aat gcc atc tct gtt ctg tac ttt gat gac agc tcc aat gtc      2012
Lys Leu Asn Ala Ile Ser Val Leu Tyr Phe Asp Asp Ser Ser Asn Val
    425                 430                 435 att ttg aaa aaa tat aga aat atg gta gta cgc tca tgt ggc tgc cac      2060
Ile Leu Lys Lys Tyr Arg Asn Met Val Val Arg Ser Cys Gly Cys His
440                 445                 450 taa tattaaataa tattgataat aacaaaaaga tctgtattaa ggtttatggc           2113
tgcaataaaa agcatacttt cagacaaaca gaaaaaaaaa                          2153
```

```
<210> SEQ ID NO 10
<211> LENGTH: 454
<212> TYPE: PRT
<213> ORGANISM: Homo sapiens

<400> SEQUENCE: 10

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
                20                  25                  30

His Val His Ser Ser Phe Ile Tyr Arg Arg Leu Arg Asn His Glu Arg
            35                  40                  45

Arg Glu Ile Gln Arg Glu Ile Leu Ser Ile Leu Gly Leu Pro His Arg
        50                  55                  60

Pro Arg Pro Phe Ser Pro Gly Lys Met Thr Asn Gln Ala Ser Ser Ala
65                  70                  75                  80

Pro Leu Phe Met Leu Asp Leu Tyr Asn Ala Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Asp Trp Ile Ile Ala Pro Glu Gly Tyr Ala Ala Phe Tyr Cys Asp Gly
    370                 375                 380
```

```
Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
            405                 410                 415

Pro Cys Cys Ala Pro Thr Lys Leu Asn Ala Ile Ser Val Leu Tyr Phe
                420                 425                 430

Asp Asp Ser Ser Asn Val Ile Leu Lys Lys Tyr Arg Asn Met Val Val
                435                 440                 445

Arg Ser Cys Gly Cys His
        450

<210> SEQ ID NO 11
<211> LENGTH: 1003
<212> TYPE: DNA
<213> ORGANISM: Homo sapiens
<220> FEATURE:
<221> NAME/KEY: CDS
<222> LOCATION: (8)..(850)

<400> SEQUENCE: 11 gaattcc gag ccc cat tgg aag gag ttc cgc ttt gac ctg acc cag atc     49
        Glu Pro His Trp Lys Glu Phe Arg Phe Asp Leu Thr Gln Ile
        1               5                   10 ccg gct ggg gag gcg gtc aca gct gcg gag ttc cgg att tac aag gtg     97
Pro Ala Gly Glu Ala Val Thr Ala Ala Glu Phe Arg Ile Tyr Lys Val
15                  20                  25                  30 ccc agc atc cac ctg ctc aac agg acc ctc cac gtc agc atg ttc cag    145
Pro Ser Ile His Leu Leu Asn Arg Thr Leu His Val Ser Met Phe Gln
                35                  40                  45 gtg gtc cag gag cag tcc aac agg gag tct gac ttg ttc ttt ttg gat    193
Val Val Gln Glu Gln Ser Asn Arg Glu Ser Asp Leu Phe Phe Leu Asp
            50                  55                  60 ctt cag acg ctc cga gct gga gac gag ggc tgg ctg gtg ctg gat gtc    241
Leu Gln Thr Leu Arg Ala Gly Asp Glu Gly Trp Leu Val Leu Asp Val
        65                  70                  75 aca gca gcc agt gac tgc tgg ttg ctg aag cgt cac aag gac ctg gga    289
Thr Ala Ala Ser Asp Cys Trp Leu Leu Lys Arg His Lys Asp Leu Gly
80                  85                  90 ctc cgc ctc tat gtg gag act gag gat ggg cac agc gtg gat cct ggc    337
Leu Arg Leu Tyr Val Glu Thr Glu Asp Gly His Ser Val Asp Pro Gly
95                  100                 105                 110 ctg gcc ggc ctg ctg ggt caa cgg gcc cca cgc tcc caa cag cct ttc    385
Leu Ala Gly Leu Leu Gly Gln Arg Ala Pro Arg Ser Gln Gln Pro Phe
                115                 120                 125 gtg gtc act ttc ttc agg gcc agt ccg agt ccc atc cgc acc cct cgg    433
Val Val Thr Phe Phe Arg Ala Ser Pro Ser Pro Ile Arg Thr Pro Arg
            130                 135                 140 gca gtg agg cca ctg agg agg agg cag ccg aag aaa agc aac gag ctg    481
Ala Val Arg Pro Leu Arg Arg Arg Gln Pro Lys Lys Ser Asn Glu Leu
        145                 150                 155 ccg cag gcc aac cga ctc cca ggg atc ttt gat gac gtc cac ggc tcc    529
Pro Gln Ala Asn Arg Leu Pro Gly Ile Phe Asp Asp Val His Gly Ser
160                 165                 170 cac ggc cgg cag gtc tgc cgt cgg cac gag ctc tac gtc agc ttc cag    577
His Gly Arg Gln Val Cys Arg Arg His Glu Leu Tyr Val Ser Phe Gln
175                 180                 185                 190 gac ctt ggc tgg ctg gac tgg gtc atc gcc ccc caa ggc tac tca gcc    625
Asp Leu Gly Trp Leu Asp Trp Val Ile Ala Pro Gln Gly Tyr Ser Ala
                195                 200                 205 tat tac tgt gag ggg gag tgc tcc ttc ccg ctg gac tcc tgc atg aac    673
```

```
                Tyr Tyr Cys Glu Gly Glu Cys Ser Phe Pro Leu Asp Ser Cys Met Asn
                            210                 215                 220 gcc acc aac cac gcc atc ctg cag tcc ctg gtg cac ctg atg aag cca         721
Ala Thr Asn His Ala Ile Leu Gln Ser Leu Val His Leu Met Lys Pro
            225                 230                 235 aac gca gtc ccc aag gcg tgc tgt gca ccc acc aag ctg agc gcc acc         769
Asn Ala Val Pro Lys Ala Cys Cys Ala Pro Thr Lys Leu Ser Ala Thr
240                 245                 250 tct gtg ctc tac tat gac agc agc aac aac gtc atc ctg cgc aag cac         817
Ser Val Leu Tyr Tyr Asp Ser Ser Asn Asn Val Ile Leu Arg Lys His
255                 260                 265                 270 cgc aac atg gtg gtc aag gcc tgc ggc tgc cac tgagtcagcc cgcccagccc       870
Arg Asn Met Val Val Lys Ala Cys Gly Cys His
                275                 280 tactgcagcc acccttctca tctggatcgg gccctgcaga ggcagaaaac ccttaaatgc       930
tgtcacagct caagcaggag tgtcaggggc cctcactctc ggtgcctact tcctgtcagg       990
cttctgggaa ttc                                                          1003

<210> SEQ ID NO 12
<211> LENGTH: 281
<212> TYPE: PRT
<213> ORGANISM: Homo sapiens

<400> SEQUENCE: 12

Glu Pro His Trp Lys Glu Phe Arg Phe Asp Leu Thr Gln Ile Pro Ala
1               5                   10                  15

Gly Glu Ala Val Thr Ala Ala Glu Phe Arg Ile Tyr Lys Val Pro Ser
                20                  25                  30

Ile His Leu Leu Asn Arg Thr Leu His Val Ser Met Phe Gln Val Val
            35                  40                  45

Gln Glu Gln Ser Asn Arg Glu Ser Asp Leu Phe Phe Leu Asp Leu Gln
        50                  55                  60

Thr Leu Arg Ala Gly Asp Glu Gly Trp Leu Val Leu Asp Val Thr Ala
65                  70                  75                  80

Ala Ser Asp Cys Trp Leu Leu Lys Arg His Lys Asp Leu Gly Leu Arg
                85                  90                  95

Leu Tyr Val Glu Thr Glu Asp Gly His Ser Val Asp Pro Gly Leu Ala
            100                 105                 110

Gly Leu Leu Gly Gln Arg Ala Pro Arg Ser Gln Gln Pro Phe Val Val
        115                 120                 125

Thr Phe Phe Arg Ala Ser Pro Ser Pro Ile Arg Thr Pro Arg Ala Val
130                 135                 140

Arg Pro Leu Arg Arg Arg Gln Pro Lys Lys Ser Asn Glu Leu Pro Gln
145                 150                 155                 160

Ala Asn Arg Leu Pro Gly Ile Phe Asp Asp Val His Gly Ser His Gly
                165                 170                 175

Arg Gln Val Cys Arg Arg His Glu Leu Tyr Val Ser Phe Gln Asp Leu
            180                 185                 190

Gly Trp Leu Asp Trp Val Ile Ala Pro Gln Gly Tyr Ser Ala Tyr Tyr
        195                 200                 205

Cys Glu Gly Glu Cys Ser Phe Pro Leu Asp Ser Cys Met Asn Ala Thr
    210                 215                 220

Asn His Ala Ile Leu Gln Ser Leu Val His Leu Met Lys Pro Asn Ala
225                 230                 235                 240

Val Pro Lys Ala Cys Cys Ala Pro Thr Lys Leu Ser Ala Thr Ser Val
```

-continued

```
            245                 250                 255
Leu Tyr Tyr Asp Ser Ser Asn Asn Val Ile Leu Arg Lys His Arg Asn
        260                 265                 270

Met Val Val Lys Ala Cys Gly Cys His
            275                 280
```

<210> SEQ ID NO 13
<211> LENGTH: 3623
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2724)..(3071)

<400> SEQUENCE: 13

```
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga ccacacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc attttaatt taaaaggatc taggtgaaga  1140
tcctttttga taatctcatg accaaaatcc cttaacgtga gttttcgttc cactgagcgt  1200
cagaccccgt agaaaagatc aaaggatctt cttgagatcc ttttttttctg cgcgtaatct  1260
gctgcttgca acaaaaaaa ccaccgctac cagcggtggt ttgtttgccg gatcaagagc  1320
taccaactct ttttccgaag gtaactggct tcagcagagc gcagatacca atactgtcc  1380
ttctagtgta gccgtagtta ggccaccact tcaagaactc tgtagcaccg cctacatacc  1440
tcgctctgct aatcctgtta ccagtggctg ctgccagtgg cgataagtcg tgtcttaccg  1500
ggttggactc aagacgatag ttaccggata aggcgcagcg tcgggctga cggggggtt  1560
cgtgcacaca gcccagcttg gagcgaacga cctacaccga actgagatac ctacagcgtg  1620
agcattgaga aagcgccacg cttcccgaag gagaaaggc ggacaggtat ccggtaagcg  1680
gcagggtcgg aacaggagag cgcacgaggg agcttccagg gggaaacgcc tggtatcttt  1740
```

```
atagtcctgt cgggtttcgc cacctctgac ttgagcgtcg attttgtga tgctcgtcag      1800 gggggcggag cctatggaaa acgccagca acgcggcctt tttacggttc ctggccttt       1860 gctggccttt tgctcacatg ttctttcctg cgttatcccc tgattctgtg ataaccgta      1920 ttaccgcctt tgagtgagct gataccgctc gccgcagccg aacgaccgag cgcagcgagt     1980
cagtgagcga ggaagcggaa gagcgcccaa tacgcaaacc gcctctcccc gcgcgttggc     2040
cgattcatta atgcagaatt gatctctcac ctaccaaaca atgccccct gcaaaaaata      2100 aattcatata aaaacatac agataaccat ctgcggtgat aaattatctc tggcggtgtt      2160
gacataaata ccactggcgg tgatactgag cacatcagca ggacgcactg accaccatga     2220
aggtgacgct cttaaaaatt aagccctgaa gaagggcagc attcaaagca gaaggctttg     2280
gggtgtgtga tacgaaacga agcattggcc gtaagtgcga ttccggatta gctgccaatg     2340
tgccaatcgc gggggttttt cgttcaggac tacaactgcc acacaccacc aaagctaact     2400
gacaggagaa tccagatgga tgcacaaaca cgccgccgcg aacgtcgcgc agagaaacag     2460
gctcaatgga aagcagcaaa tcccctgttg gttggggtaa gcgcaaaacc agttccgaaa     2520
gattttttta actataaacg ctgatggaag cgtttatgcg gaagaggtaa agcccttccc     2580
gagtaacaaa aaaacaacag cataaataac cccgctctta cacattccag ccctgaaaaa     2640
gggcatcaaa ttaaaccaca cctatggtgt atgcatttat ttgcatacat tcaatcaatt     2700
gttatctaag gaaatactta cat atg caa gct aaa cat aaa caa cgt aaa cgt   2753
                          Met Gln Ala Lys His Lys Gln Arg Lys Arg
                            1               5                  10 ctg aaa tct agc tgt aag aga cac cct ttg tac gtg gac ttc agt gac      2801
Leu Lys Ser Ser Cys Lys Arg His Pro Leu Tyr Val Asp Phe Ser Asp
             15                  20                  25 gtg ggg tgg aat gac tgg att gtg gct ccc ccg ggg tat cac gcc ttt      2849
Val Gly Trp Asn Asp Trp Ile Val Ala Pro Pro Gly Tyr His Ala Phe
         30                  35                  40 tac tgc cac gga gaa tgc cct ttt cct ctg gct gat cat ctg aac tcc      2897
Tyr Cys His Gly Glu Cys Pro Phe Pro Leu Ala Asp His Leu Asn Ser
         45                  50                  55 act aat cat gcc att gtt cag acg ttg gtc aac tct gtt aac tct aag      2945
Thr Asn His Ala Ile Val Gln Thr Leu Val Asn Ser Val Asn Ser Lys
 60                  65                  70 att cct aag gca tgc tgt gtc ccg aca gaa ctc agt gct atc tcg atg      2993
Ile Pro Lys Ala Cys Cys Val Pro Thr Glu Leu Ser Ala Ile Ser Met
 75                  80                  85                  90 ctg tac ctt gac gag aat gaa aag gtt gta tta aag aac tat cag gac      3041
Leu Tyr Leu Asp Glu Asn Glu Lys Val Val Leu Lys Asn Tyr Gln Asp
             95                 100                 105 atg gtt gtg gag ggt tgt ggg tgt cgc tag tacagcaaaa ttaaatacat        3091
Met Val Val Glu Gly Cys Gly Cys Arg
            110                 115 aaatatatat atatatatat attttagaaa aaagaaaaaa atctagagtc gacctgcagt    3151
aatcgtacag ggtagtacaa ataaaaaagg cacgtcagat gacgtgcctt ttttcttgtg    3211
agcagtaagc ttggcactgg ccgtcgtttt acaacgtcgt gactgggaaa accctggcgt    3271
tacccaactt aatcgccttg cagcacatcc ccctttcgcc agctggcgta atagcgaaga    3331
ggcccgcacc gatcgccctt cccaacagtt gcgcagcctg aatggcgaat ggcgcctgat    3391
gcggtatttt ctccttacgc atctgtgcgg tatttcacac cgcatatatg gtgcactctc    3451
agtacaatct gctctgatgc cgcatagtta agccagcccc gacacccgcc aacacccgct    3511
```

```
gacgcgccct gacgggcttg tctgctcccg gcatccgctt acagacaagc tgtgaccgtc    3571
tccgggagct gcatgtgtca gaggttttca ccgtcatcac cgaaacgcgc ga            3623
```

```
<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Met Gln Ala Lys His Lys Gln Arg Lys Arg Leu Lys Ser Ser Cys Lys
 1               5                  10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
    50                  55                  60

Gln Thr Leu Val Asn Ser Val Asn Ser Lys Ile Pro Lys Ala Cys Cys
65                  70                  75                  80

Val Pro Thr Glu Leu Ser Ala Ile Ser Met Leu Tyr Leu Asp Glu Asn
                85                  90                  95

Glu Lys Val Val Leu Lys Asn Tyr Gln Asp Met Val Val Glu Gly Cys
            100                 105                 110

Gly Cys Arg
        115
```

```
<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
catgggcagc tcgag                                                     15

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gagggttgtg ggtgtcgcta gtgagtcgac tacagcaaaa tt                       42

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggatgtgggt gccgctgact ctagagtcga cggaattc                            38
```

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
aattcaccat gattcctggt aaccgaatgc t                              31

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
cattcggtta ccaggaatca tggtg                                    25

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
cgacctgcag ccaccatgca tctgactgta                                30

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
tgcctgcagt ttaatattag tggcagc                                  27

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
cgacctgcag ccacc                                               15

<210> SEQ ID NO 23
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tcgacccacc atgccggggc tggggcggag ggcgcagtgg ctgtgctggt ggtgggggct      60
gtgctgcagc tgctgcgggc c                                               81

-continued

<210> SEQ ID NO 24
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgcagcagct gcacagcagc ccccaccacc agcacagcca ctgcgccctc cgccccagcc    60
ccggcatggt ggg                                                       73

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcgactggtt t                                                         11

<210> SEQ ID NO 26
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 cgaaaccag                                                             9

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tcgacaggct cgcctgca                                                  18

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggcgagcctg                                                           10

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
caggtcgacc caccatgcac gtgcgctca                                      29

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tctgtcgacc tcggaggagc tagtggc                                        27

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
caggtcgacc cacc                                                      14

<210> SEQ ID NO 32
<211> LENGTH: 449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgtctcata atcgttctaa aactccaaaa aatcaagaag ctctgcgtat ggccaacgtg     60
gcagagaaca gcagcagcga ccagaggcag gcctgtaaga agcacgagct gtatgtcagc    120
ttccgagacc tgggctggca ggactggatc atcgcgcctg aaggctacgc cgcctactac    180
tgtgaggggg agtgtgcctt ccctctgaac tcctacatga acgccaccaa ccacgccatc    240
gtgcagacgc tggtccactt catcaacccg gaaacggtgc ccaagccctg ctgtgcgccc    300
acgcagctca atgccatctc cgtcctctac ttcgatgaca gctccaacgt catcctgaag    360
aaatacagaa acatggtggt ccgggcctgt ggctgccact agctcctccg agaattcaga    420 cccctttgggg ccaagttttt ctggatcct                                     449

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caagaaggag atatacat                                                  18

<210> SEQ ID NO 34
<211> LENGTH: 377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atgcgtaaac aatggattga accacgtaac tgtgctcgtc gttatctgaa agtagacttt    60

```
gcagatattg gctggagtga atggattatc tcccccaagt cctttgatgc ctattattgc      120
tctggagcat gccagttccc catgccaaag tctttgaagc catcaaatca tgctaccatc      180
cagagtatag tgagagctgt gggggtcgtt cctgggattc ctgagccttg ctgtgtacca      240
gaaaagatgt cctcactcag tattttattc tttgatgaaa ataagaatgt agtgcttaaa      300 gtataccca acatgacagt agagtcttgc gcttgcagat aacctggcaa agaactcatt       360
tgaatgctta attcaat                                                    377
```

RECOMBINANT BONE MORPHOGENETIC PROTEIN HETERODIMERS, COMPOSITIONS AND METHODS OF USE

CROSS REFERENCE TO RELATED APPLICATIONS

This application is a divisional of U.S. Ser. No. 09/780,601 filed Feb. 9, 2001 (now U.S. Pat. No. 6,593,109), which is a divisional of U.S. Ser. No. 08/469,411, filed Jun. 6, 1995, now U.S. Pat. No. 6,190,880, which is a continuation of U.S. Ser. No. 07/989,847, filed Nov. 27, 1992, now U.S. Pat. No. 5,866,364, which is a continuation-in-part of U.S. Ser. No. 07/864,692, filed Apr. 7, 1992, now abandoned, which is a continuation-in-part of U.S. Ser. No. 07/787,496, filed Nov. 4, 1991, now abandoned.

FIELD OF THE INVENTION

The present invention relates to a series of novel recombinant heterodimeric proteins useful in the field of treating bone defects, healing bone injury and in wound healing in general. The invention also relates to methods for obtaining these heterodimers, methods for producing them by recombinant genetic engineering techniques, and compositions containing them.

BACKGROUND OF THE INVENTION

In recent years, protein factors which are characterized by bone or cartilage growth inducing properties have been isolated and identified. See, e.g., U.S. Pat. No. 5,013,649, PCT published application WO90/11366; PCT published application WO91/05802 and the variety of references cited therein. See, also, PCT/US90/05903 which discloses a protein sequence termed OP-1, which is substantially similar to human BMP-7, and has been reported to have osteogenic activity.

A family of individual bone morphogenetic proteins (BMPs), termed BMP-2 through BMP-9 have been isolated and identified. Incorporated by reference for the purposes of providing disclosure of these proteins and methods of producing them are co-owned, co-pending U.S. patent application Ser. No. 721,847 (now U.S. Pat. No. 6,150,328) and the related applications recited in its preamble. Of particular interest, are the proteins termed BMP-2 and BMP-4, disclosed in the above-referenced application; BMP-7, disclosed in Ser. No. 438,919 (now U.S. Pat. No. 5,141,905); BMP-5, disclosed in Ser. No. 370,547 (now U.S. Pat. No. 5,106,748) and Ser. No. 356,033, now abandoned; and BMP-6, disclosed in Ser. No. 370,544, now abandoned, and Ser. No. 347,559, now abandoned; and BMP-8, disclosed in Ser. No. 525,357, now abandoned. Additional members of the BMP family include BMP-1, disclosed in Ser. No. 655,578 (now U.S. Pat. No. 6,432,919); BMP-9, disclosed in Ser. No. 720,590, now abandoned; and BMP-3, disclosed in Ser. No. 179,197, now abandoned, and PCT publication 89/01464. These applications are incorporated herein by reference for disclosure of these BMPs.

There remains a need in the art for other proteins and compositions useful in the fields of bone and wound healing.

SUMMARY OF THE INVENTION

In one aspect, the invention provides a method for producing a recombinant heterodimeric protein having bone stimulating activity comprising culturing a selected host cell containing a polynucleotide sequence encoding a first selected BMP or fragment thereof and a polynucleotide sequence encoding a second selected BMP or fragment thereof. The resulting co-expressed, biologically active heterodimer is isolated from the culture medium.

According to one embodiment of this invention, the host cell may be co-transfected with one or more vectors containing coding sequences for one or more BMPs. Each BMP polynucleotide sequence may be present on the same vector or on individual vectors transfected into the cell. Alternatively, the BMPs or their fragments may be incorporated into a chromosome of the host cell. Additionally, a single transcription unit may encode single copy of two genes encoding a different BMP.

According to another embodiment of this invention, the selected host cell containing the two polypeptide encoding sequences is a hybrid cell line obtained by fusing two selected, stable host cells, each host cell transfected with, and capable of stably expressing, a polynucleotide sequence encoding a selected first or second BMP or fragment thereof.

In another aspect of the present invention, therefore, there are provided recombinant heterodimeric proteins comprising a protein or fragment of a first BMP in association with a protein or fragment of a second BMP. The heterodimer may be characterized by bone stimulating activity. The heterodimers may comprise a protein or fragment of BMP-2 associated with a protein or fragment of either BMP-5, BMP-6, BMP-7 or BMP-8; or a protein or fragment of BMP-4 associated with a protein or fragment of either BMP-5, BMP-6, BMP-7 or BMP-8. In further embodiments the heterodimers may comprise a protein or fragment of BMP-2 associated with a protein or fragment of either BMP-1, BMP-3 or BMP-4. BMP-4 may also form a heterodimer in association with BMP-1, BMP-2 or a fragment thereof. Still further embodiments may comprise heterodimers involving combinations of BMP-5, BMP-6, BMP-7 and BMP-8. For example, the heterodimers may comprise BMP-5 associated with BMP-6, BMP-7 or BMP-8; BMP-6 associated with BMP-7 or BMP-8; or BMP-7 associated with BMP-8. These heterodimers may be produced by co-expressing each protein in a selected host cell and isolating the heterodimer from the culture medium.

As a further aspect of this invention a cell line is provided which comprises a first polynucleotide sequence encoding a first BMP or fragment thereof and a second polynucleotide sequence encoding a second BMP or fragment thereof, the sequences being under control of one or more suitable expression regulatory systems capable of co-expressing the BMPs as a heterodimer. The cell line may be transfected with one or more than one polynucleotide molecule. Alternatively, the cell line may be a hybrid cell line created by cell fusion as described above.

Another aspect of the invention is a polynucleotide molecule or plasmid vector comprising a polynucleotide sequence encoding a first selected BMP or fragment thereof and a polynucleotide sequence encoding a second selected BMP or fragment thereof. The sequences are under the control of at least one suitable regulatory sequence capable of directing co-expression of each protein or fragment. The molecule may contain a single transcription unit containing a copy of both genes, or more than one transcription unit, each containing a copy of a single gene.

As still another aspect of this invention there is provided a method for producing a recombinant dimeric or heterodimeric protein having bone stimulating activity in a prokaryotic cell comprising culturing a selected host cell containing a polynucleotide sequence encoding a first selected BMP or fragment thereof; culturing a second selected host cell containing a polynucleotide sequence encoding a second selected BMP or fragment thereof; isolating monomeric forms of each BMP protein from the culture medium and co-assembling a monomer of the first protein with a monomer of the second protein. The first protein and the second protein may be the same or different BMPs. The resulting biologically active dimer or heterodimer is thereafter isolated from the mixture. Preferred cells are E. coli.

Thus, as further aspects of this invention recombinant BMP dimers or heterodimers produced in eukaryotic cells are provided, as well as suitable vectors or plasmids, and selected transformed cells useful in such a production method.

Other aspects and advantages of the present invention are described further in the following detailed description of preferred embodiments of the present invention.

BRIEF DESCRIPTION OF THE FIGURES

FIG. 1 provides the DNA and amino acid sequences of human BMP-2 (SEQ ID NOs: 1 and 2).

FIG. 2 provides the DNA and amino acid sequences of human BMP-4 (SEQ ID NOs: 3 and 4).

FIG. 3 provides the DNA and amino acid sequences of human BMP-7 (SEQ ID NOs: 5 and 6).

FIG. 4 provides the DNA and amino acid sequences of human BMP-6 (SEQ ID NOs: 7 and 8).

FIG. 5 provides the DNA and amino acid sequences of human BMP-5 (SEQ ID NOs: 9 and 10).

FIG. 6 provides the DNA and amino acid sequences of human BMP-8 (SEQ ID NOs: 11 and 12).

FIG. 12 provides a comparison of BMP-2, BMP-6 and BMP-2/6 in vivo activity.

DETAILED DESCRIPTION OF THE INVENTION

Figure 7:
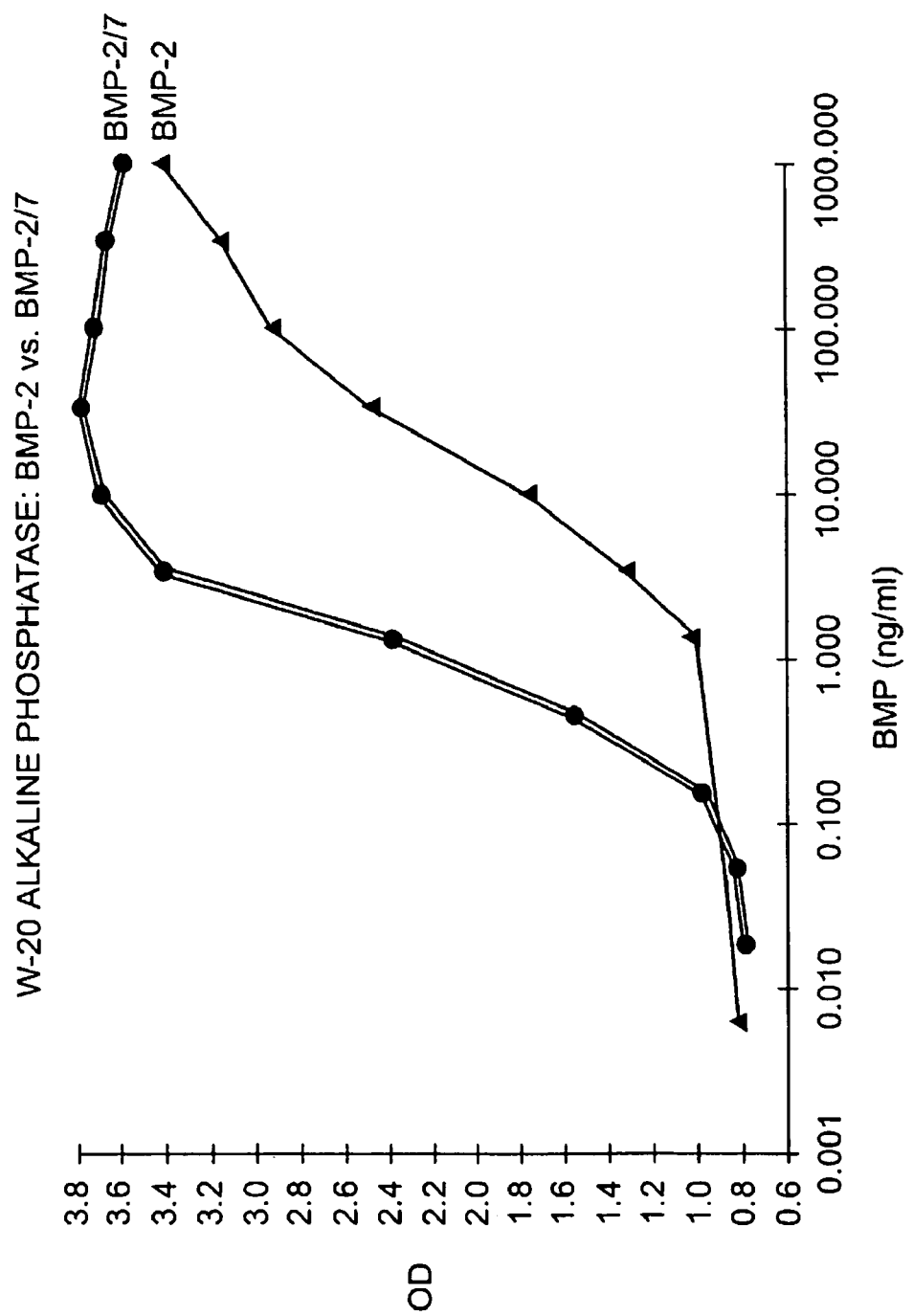
FIG. 7 provides the DNA sequence of vector pALB2-781 containing the mature portion of the BMP-2 gene (SEQ ID NO: 13).

The present invention provides a method for producing recombinant heterodimeric proteins having bone stimulating activity, as well as the recombinant heterodimers themselves, and compositions containing them for bone-stimulating or repairing therapeutic use.

As used throughout this document, the term 'heterodimer' is defined as a biologically-active protein construct comprising the association of two different BMP protein monomers or active fragments thereof joined through at least one covalent, disulfide linkage. A heterodimer of this invention may be characterized by the presence of between one to seven disulfide linkages between the two BMP component strands.

According to the present invention, therefore, a method for producing a recombinant BMP heterodimer according to this invention comprises culturing a selected host cell containing a polynucleotide sequence encoding a first selected BMP or a biologically active fragment thereof and a polynucleotide sequence encoding a second selected BMP or a fragment thereof. The resulting co-expressed, biologically active heterodimer is formed within the host cell, secreted therefrom and isolated from the culture medium. Preferred embodiments of methods for producing the heterodimeric proteins of this invention, are described in detail below and in the following examples. Preferred methods of the invention involve known recombinant genetic engineering techniques [See, e.g., Sambrook et al, "Molecular cloning. A Laboratory Manual.", 2d edition, Cold Spring Harbor Laboratory, Cold Spring Harbor, N.Y. (1989)]. However, other methods, such as conventional chemical synthesis may also be useful in preparing a heterodimer of this invention.

BMP heterodimers generated by this method are produced in a mixture of homodimers and heterodimers. This mixture of heterodimers and homodimers may be separated from contaminants in the culture medium by resort to essentially conventional methods, such as classical protein biochemistry or affinity antibody columns specific for one of the BMPs making up the heterodimer. Additionally, if desired, the heterodimers may be separated from homodimers in the mixture. Such separation techniques allow unambiguous determination of the activity of the heterodimeric species. Example 4 provides one presently employed purification scheme for this purpose.

Preferably the recombinant heterodimers of this invention produced by these methods involve the BMPs designated human BMP-2, human BMP-4, human BMP-5, human BMP-6, human BMP-7 and BMP-8. However, BMP-3 has also been determined to form an active heterodimer with BMP-2. Other species of these BMPs as well as BMPs than those specifically identified above may also be employed in heterodimers useful for veterinary, diagnostic or research use. However, the human proteins, specifically those proteins identified below, are preferred for human pharmaceutical uses.

Human BMP-2 is characterized by containing substantially the entire sequence, or fragments, of the amino acid sequence and DNA sequence disclosed in FIG. 1. Human BMP-2 proteins are further characterized as disulfide-linked dimers and homodimers of mature BMP-2 subunits. Recombinantly-expressed BMP-2 subunits include protein species having heterogeneous amino termini. One BMP-2 subunit is characterized by comprising amino acid #249 (Ser)-#396 (Arg) of FIG. 1 (SEQ ID NOs: 1 and 2). Another BMP-2 subunit is characterized by comprising amino acid #266 (Thr)-#396 (Arg) of FIG. 1. Another BMP-2 subunit is characterized by comprising amino acid #296 (Cys)-#396 (Arg) of FIG. 1. A mature BMP-2 subunit is characterized by comprising amino acid #283 (Gln)-#396 (Arg) of FIG. 1. This latter subunit is the presently most abundant protein species which results from recombinant expression of BMP-2 (FIG. 1). However, the proportions of certain species of BMP-2 produced may be altered by manipulating the culture conditions. BMP-2 may also include modifications of the sequences of FIG. 1, e.g., deletion of amino acids #241-280 and changing amino acid #245 Arg to Ile, among other changes.

As described in detail in U.S. patent application Ser. No. 721,847 (now U.S. Pat. No. 6,150,328), incorporated by reference herein, human BMP-2 may be produced by culturing a cell transformed with a DNA sequence comprising the nucleotide coding sequence from nucleotide #356 to #1543 in FIG. 1 and recovering and purifying from the culture medium one or more of the above-identified protein species, substantially free from other proteinaceous materials with which it is co-produced. Human BMP-2 proteins are characterized by the ability to induce bone formation. Human BMP-2 also has in vitro activity in the W20 bioassay. Human BMP-2 is further characterized by the ability to induce cartilage formation.

Human BMP-2 may be further characterized by the ability to demonstrate cartilage and/or bone formation activity in the rat bone formation assay described in the above-referenced application.

Human BMP-4 is characterized by containing substantially the entire sequence, or fragments, of the amino acid sequence and DNA sequence disclosed in FIG. 2 (SEQ ID NOs: 3 and 4). Human BMP-4 proteins are further characterized as disulfide-linked dimers and homodimers of mature BMP-4 subunits. Recombinantly-expressed BMP-4 subunits may include protein species having heterogeneous amino termini. A mature subunit of human BMP-4 is characterized by an amino acid sequence comprising amino acids #293 (Ser)-#408 (Arg) of FIG. 2. Other amino termini of BMP-4 may be selected from the sequence of FIG. 2. Modified versions of BMP-4, including proteins further truncated at the amino or carboxy termini, may also be constructed by resort to conventional mutagenic techniques.

As disclosed in above-incorporated patent application Ser. No. 721,847 (now U.S. Pat. No. 6,150,328), BMP-4 may be produced by culturing a cell transformed with a DNA sequence comprising the nucleotide coding sequence from nucleotide #403 to nucleotide #1626 in FIG. 2 and recovering and purifying from the culture medium a protein containing the amino acid sequence from amino acid #293 to #408 as shown in FIG. 2, substantially free from other proteinaceous materials with which it is co-produced. BMP-4 proteins are capable of inducing the formation of bone. BMP-4 proteins are capable of inducing formation of cartilage. BMP-4 proteins are further characterized by the ability to demonstrate cartilage and/or bone formation activity in the rat bone formation assay.

Human BMP-7 is characterized by containing substantially the entire sequence, or fragments, of the amino acid sequence and DNA sequence disclosed in FIG. 3. Human BMP-7 proteins are further characterized as disulfide-linked dimers and homodimers of mature BMP-7 subunits. Recombinantly-expressed BMP-7 subunits include protein species having heterogeneous amino termini. One BMP-7 subunit is characterized by comprising amino acid #293 (Ser)-1431 (His) of FIG. 3 (SEQ ID NOs: 5 and 6). This subunit is the most abundantly formed protein produced by recombinant expression of the BMP-7 sequence. Another BMP-7 subunit is characterized by comprising amino acids #300 (Ser)-#431 (His) of FIG. 3. Still another BMP-7 subunit is characterized by comprising amino acids #316 (Ala)-#431 (His) of FIG. 3. Other amino termini of BMP-7 may be selected from the sequence of FIG. 3. Similarly, modified versions, including proteins further truncated at the amino or carboxy termini, of BMP-7 may also be constructed by resort to conventional mutagenic techniques.

As disclosed in above-incorporated patent application Ser. No. 438,919 (now U.S. Pat. No. 5,141,905), BMP-7 may be produced by culturing a cell transformed with a DNA sequence comprising the nucleotide coding sequence from nucleotide #97 to nucleotide #1389 in FIG. 3 and recovering and purifying from the culture medium a protein containing the amino acid sequence from amino acid #293 to #431 as shown in FIG. 3, substantially free from other proteinaceous or contaminating materials with which it is co-produced. These proteins are capable of stimulating, promoting, or otherwise inducing cartilage and/or bone formation.

Human BMP-6 is characterized by containing substantially the entire sequence, or fragments, of the amino acid sequence and DNA sequence disclosed in FIG. 4. Human BMP-6 proteins are further characterized as disulfide-linked dimers of mature BMP-6 subunits. Recombinantly-expressed BMP-6 subunits may include protein species having heterogeneous amino termini. One BMP-6 subunit is characterized by comprising amino acid #375 (Ser)-#513 (His) of FIG. 4 (SEQ ID NOs: 7 and 8). Other amino termini of BMP-6 may be selected from the sequence of FIG. 4. Modified versions, including proteins further truncated at the amino or carboxy termini, of BMP-6 may also be constructed by resort to conventional mutagenic techniques.

As described in detail in U.S. patent application Ser. No. 490,033 (now U.S. Pat. No. 5,187,076), incorporated by reference herein, human BMP-6 may be produced by culturing a cell transformed with a DNA sequence comprising the nucleotide coding sequence from nucleotide #160 to #1698 in FIG. 4 and recovering and purifying from the culture medium a protein comprising amino acid #375 to #513 of FIG. 4, substantially free from other proteinaceous materials or other contaminating materials with which it is co-produced. Human BMP-6 may be further characterized by the ability to demonstrate cartilage and/or bone formation activity in the rat bone formation assay.

Human BMP-5 is characterized by containing substantially the entire sequence, or fragments, of the amino acid sequence and DNA sequence disclosed in FIG. 5 (SEQ ID NOs: 9 and 10). Human BMP-5 proteins are further characterized as disulfide-linked dimers of mature BMP-5 subunits. Recombinantly-expressed BMP-5 subunits may include protein species having heterogeneous amino termini. One BMP-5 subunit is characterized by comprising amino acid #329 (Ser)-#454 (His) of FIG. 5. Other amino termini of BMP-5 may be selected from the sequence of FIG. 5. Modified versions, including proteins further truncated at the amino or carboxy termini, of BMP-5 may also be constructed by resort to conventional mutagenic techniques.

As described in detail in U.S. patent application Ser. No. 588,227, now abandoned, incorporated by reference herein, human BMP-5 may be produced by culturing a cell transformed with a DNA sequence comprising the nucleotide coding sequence from nucleotide #701 to #2060 in FIG. 5 and recovering and purifying from the culture medium a protein comprising amino acid #329 to #454 of FIG. 5, substantially free from other proteinaceous materials or other contaminating materials with which it is co-produced. Human BMP-5 may be further characterized by the ability to demonstrate cartilage and/or bone formation activity in the rat bone formation assay described in the above-referenced application.

Human BMP-8 is characterized by containing substantially the entire sequence, or fragments, of the amino acid sequence and DNA sequence disclosed in FIG. 6. Human BMP-8 proteins may be further characterized as disulfide-linked dimers of mature BMP-8 subunits. Recombinantly-expressed BMP-8 subunits may include protein species having heterogeneous amino termini. A BMP-8 sequence or subunit sequence comprises amino acid #143 (Ala)-#281 (His) of FIG. 6 (SEQ ID NOs: 11 and 12). Other amino termini of BMP-8 may be selected from the sequence of FIG. 6. Modified versions, including proteins further truncated at the amino or carboxy termini, of BMP-8 may also be constructed by resort to conventional mutagenic techniques.

As described generally in U.S. patent application Ser. No. 525,357, now abandoned, incorporated by reference herein, and as further described herein, human BMP-8 may be produced by culturing a cell transformed with a DNA sequence comprising the nucleotide coding sequence from nucleotide #1 to #850 in FIG. 6 and recovering and purifying from the culture medium a protein comprising amino acid #143 to #281 of FIG. 6, or similar amino acid sequences with heterogenous N-termini, substantially free from other proteinaceous materials or other contaminating materials with which it is co-produced. This BMP-8 may also be produced in *E. coli* by inserting into a vector the sequence encoding amino acid #143 to 281 of FIG. 6 with a Met inserted before amino acid #143. Human BMP-8 may be further characterized by the ability to demonstrate cartilage and/or bone formation activity in the rat bone formation assay.

This BMP-8 may also be produced in *E. coli* by inserting into a vector the sequence encoding amino acid 1143 to 281 of FIG. 6 with a Met inserted before amino acid #143. Human BMP-8 may be further characterized by the ability to demonstrate cartilage and/or bone formation activity in the rat bone formation assay.

Each above described BMP protein in its native, non-reduced dimeric form may be further characterized by an apparent molecular weight on a 12% Laemmli gel ranging between approximately 28 kD to approximately 40 kD. Analogs or modified versions of the DNA and amino acid sequences described herein which provide proteins or active fragments displaying bone stimulating or repairing activity in the rat bone formation assay described below in Example 9, are also classified as suitable BMPs for use in this invention, further provided that the proteins or fragments contain one or more Cys residues for participation in disulfide linkages. Useful modifications of these sequences may be made by one of skill in the art with resort to known recombinant genetic engineering techniques. Production of these BMP sequences in mammalian cells produces homodimers, generally mixtures of homodimers having heterologous N termini. Production of these BMP sequences in *E. coli* produces monomeric protein species.

Thus, according to this invention one recombinant heterodimer of the present invention comprises the association of a human BMP-2, including, e.g., a monomeric strand from a mature BMP-2 subunit as described above or an active fragment thereof, bound through one or up to seven covalent, disulfide linkages to a human BMP-5 including, e.g., a monomeric strand from a mature BMP-5 subunit as described above or an active fragment thereof. Another recombinant heterodimer of the present invention comprises the association of a human BMP-2, as described above, bound through one or up to seven covalent, disulfide linkages to a human BMP-6, including, e.g., a monomeric strand from a BMP-6 subunit as described above or an active fragment thereof. Another recombinant heterodimer of the present invention comprises the association of a human BMP-2, as described above, bound through one or up to seven covalent, disulfide linkages to a human BMP-7, including, e.g., a monomeric strand of a BMP-7 subunit as described above or an active fragment thereof. Another recombinant heterodimer of the present invention comprises the association of a human BMP-2, as described above, bound through one or up to seven covalent, disulfide linkages to a human BMP-8, including, e.g., a monomeric strand of a BMP-8 subunit as described above or an active fragment thereof.

Still another recombinant heterodimer of the present invention comprises the association of a human BMP-4, including, e.g., a monomeric strand of a BMP-4 subunit as described above or an active fragment thereof, bound through one or up to seven covalent, disulfide linkages to a human BMP-5, as described above. Another recombinant heterodimer of the present invention comprises the association of a human BMP-4, as described above, bound through one or more covalent, disulfide linkages to a human BMP-6, as described above. Another recombinant heterodimer of the present invention comprises the association of a human BMP-4, as described above bound through one or more covalent, disulfide linkages to a human BMP-7, as described above. Another recombinant heterodimer of the present invention comprises the association of a human BMP-4, as described above, bound through one or more covalent, disulfide linkages to a human BMP-8, as described above.

A further recombinant heterodimer of the present invention comprises the association of a human BMP-2, including, e.g., a monomeric strand from a mature BMP-2 subunit as described above or an active fragment thereof, bound through at least one disulfide linkage to a human BMP-3 including, e.g., a monomeric strand from a mature BMP-3 subunit as described above or an active fragment thereof. Another recombinant heterodimer of the present invention comprises the association of a human BMP-2, as described above, bound through at least one disulfide linkage to a human BMP-4, including, e.g., a monomeric strand from a BMP-4 subunit as described above or an active fragment thereof. Another recombinant heterodimer of the present invention comprises the association of a human BMP-5, as described above, bound through at least one disulfide linkage to a human BMP-6, including, e.g., a monomeric strand of a BMP-6 subunit as described above or an active fragment thereof. Another recombinant heterodimer of the present invention comprises the association of a human BMP-5, as described above, bound through at least one disulfide linkage to a human BMP-7, including, e.g., a monomeric strand of a BMP-7 subunit as described above or an active fragment thereof. In addition, human BMP-5 may be associated with human BMP-8 bound through at least one disulfide linkage to a human BMP-8 subunit or active fragment thereof.

Still another recombinant heterodimer of the present invention comprises the association of a human. BMP-6, including, e.g., a monomeric strand of a BMP-6 subunit as described above or an active fragment thereof, bound through at least one disulfide linkage to a human BMP-7, as described above. Another recombinant heterodimer of the present invention comprises the association of a human BMP-6, as described above, bound through one or more covalent, disulfide linkages to a human BMP-8, as described above. Another recombinant heterodimer of the present invention comprises the association of a human BMP-7, as described above bound through one or more covalent, disulfide linkages to a human BMP-8, as described above.

The disulfide linkages formed between the monomeric strands of the BMPs may occur between one Cys on each strand. Disulfide linkages may form between two Cys on each BMP. Disulfide linkages may form between three Cys on each BMP. Disulfide linkages may form between four Cys on each BMP. Disulfide linkages may form between five Cys on each BMP. Disulfide linkages may form between six Cys on each BMP. Disulfide linkages may form between seven Cys on each BMP. These disulfide linkages may form between adjacent Cys on each BMP or between only selected Cys interspersed within the respective protein sequence. Various heterodimers having the same BMP component strands may form with different numbers of disulfide linkages. Various heterodimers having the same BMP component strands may form with disulfide bonds at different Cys locations. Different heterodimers encompassed by this invention having the same BMP components may differ based upon their recombinant production in mammalian cells, bacterial cells, insect or yeast cells.

These recombinant heterodimers may be characterized by increased alkaline phosphatase activity in the W20 mouse stromal cell line bioassay (Example 8) compared to the individual BMP homodimers, one strand of which forms each heterodimer. Further, these heterodimers are characterized by greater activity in the W20 bioassay than is provided by simple mixtures of the individual BMP dimers. Preliminary characterization of heterodimers measured on the W20 bioassay have demonstrated that heterodimers of BMP-2 with BMP-5, BMP-6 or BMP-7 are very active. Similarly, heterodimers of BMP-4 with BMP-5, BMP-6 or BMP-7 are strongly active in the W20 bioassay.

Heterodimers of this invention may also be characterized by activity in bone growth and stimulation assays. For example, a heterodimer of this invention is also active in the rat bone formation assay described below in Example 9. The heterodimers are also active in the osteocalcin bioassay described in Example 8. Other characteristics of a heterodimer of this invention include co-precipitation with anti-BMP antibodies to the two different constituent BMPs, as well as characteristic results on Western blots, high pressure liquid chromatography (HPLC) and on two-dimensional gels, with and without reducing conditions.

One embodiment of the method of the present invention for producing recombinant BMP heterodimers involves culturing a suitable cell line, which has been co-transfected with a DNA sequence coding for expression of a first BMP or fragment thereof and a DNA sequence coding for expression of a second BMP or fragment thereof, under the control of known regulatory sequences. The transformed host cells are cultured and the heterodimeric protein recovered and purified from the culture medium.

In another embodiment of this method which is the presently preferred method of expression of the heterodimers of this invention, a single host cell, e.g., a CHO DUKX cell, is co-transfected with a first DNA molecule containing a DNA sequence encoding one BMP and a second DNA molecule containing a DNA sequence encoding a second selected BMP. One or both plasmids contain a selectable marker that can be used to establish stable cell lines expressing the BMPs. These separate plasmids containing distinct BMP genes on seperate transcription units are mixed and transfected into the CHO cells using conventional protocols. A ratio of plasmids that gives maximal expression of activity in the W20 assay, generally, 1:1, is determined.

For example, as described in detail in Example 3, equal ratios of a plasmid containing the first BMP and a dihydrofolate reductase (DHFR) marker gene and another plasmid containing a second BMP and a DHFR marker gene can be co-introduced into DHFR-deficient CHO cells, DUKX-BII, by calcium phosphate coprecipitation and transfection, electroporation, microinjection, protoplast fusion or lipofection. Individual DHFR expressing transformants are selected for growth in alpha media with dialyzed fetal calf serum by conventional means. DHFR+ cells containing increased gene copies can be selected for propagation in increasing concentrations of methotrexate (MTX) (e.g. sequential steps in 0.02, 0.1, 0.5 and 2.0 uM MTX) according to the procedures of Kaufman and Sharp, *J. Mol. Biol.*, 159:601-629 (1982); and Kaufman et al, *Mol. Cell Biol.*, 5:1750 (1983). Expression of the heterodimer or at least one BMP linked to DHFR should increase with increasing levels of MTX resistance. Cells that stably express either or both BMP/DHFR genes will survive. However at a high frequency, cell lines stably incorporate and express both plasmids that were present during the initial transfection. The conditioned medium is thereafter harvested and the heterodimer isolated by conventional methods and assayed for activity. This approach can be employed with DHFR-deficient cells.

As an alternative embodiment of this method, a DNA molecule containing one selected BMP gene may be transfected into a stable cell line which already expresses another selected BMP gene. For example as described in detail in Example 3 below, a stable CHO cell line expressing BMP-7 with the DHFR marker (designated 7 MB9) [Genetics Institute, Inc] is transfected with a plasmid containing BMP-2 and a second selectable marker gene, e.g., neomycin resistance (Neo). After transfection, the cell is cultured and suitable cells selected by treatment with MTX and the antibiotic, G-418. Surviving cells are then screened for the expression of the heterodimer. This expression system has the advantage of permitting a single step selection.

Alternative dual selection strategies using different cell lines or different markers can also be used. For example, the use of an adenosine deaminase (ADA) marker to amplify the second BMP gene in a stable CHO cell line expressing a different BMP with the DHFR marker may be preferable, since the level of expression can be increased using deoxycoformycin (DCF)-mediated gene amplification. (See the ADA containing plasmid described in Example 1). Alternatively, any BMP cell line made by first using this marker can then be the recipient of a second BMP expression vector containing a distinct marker and selected for dual resistance and BMP coexpression.

Still another embodiment of a method of expressing the heterodimers of this invention includes transfecting the host cell with a single DNA molecule encoding multiple genes for expression either on a single transcription unit or on separate transcription units. Multicistronic expression involves multiple polypeptides encoded within a single transcript, which can be efficiently translated from vectors utilizing a leader sequence, e.g., from the EMC virus, from poliovirus, or from other conventional sources of leader sequences. Two BMP genes and a selectable marker can be expressed within a single transcription unit. For example, vectors containing the configuration BMPx-EMC-BMPy-DHFR or BMPx-EMC-BMPy-EMC-DHFR can be transfected into CHO cells and selected and amplified using the DHFR marker. A plasmid may be constructed which contains DNA sequences encoding two different BMPs, one or more marker genes and a suitable leader or regulatory sequence on a single transcription unit.

Similarly, host cells may be transfected with a single plasmid which contains separate transcription units for each BMP. A selectable marker, e.g., DHFR, can be contained on a another transcription unit, or alternatively as the second cistron on one or both of the BMP genes. These plasmids may be transfected into a selected host cell for expression of the heterodimer, and the heterodimer isolated from the cells or culture medium as described above.

Another embodiment of this expression method involves cell fusion. Two stable cell lines which express selected BMPs, such as a cell line expressing BMP-2 (e.g., 2EG5) and a cell line expressing BMP-7 (e.g., 7 MB9), developed using the DHFR/MTX gene amplification system and expressing BMP at high levels, as described in Example 1 and in the above incorporated U.S. applications, can be transfected with one of several dominant marker genes (e.g., neo$^r$, hygromycin$^r$, GPT). After sufficient time in coculture (approximately one day) one resultant cell line expressing one BMP and a dominant marker can be fused with a cell line expressing a different BMP and preferably a different marker using a fusigenic reagent, such as polyethylene glycol, Sendai virus or other known agent.

The resulting cell hybrids expressing both dominant markers and DHFR can be selected using the appropriate culture conditions, and screened for coexpression of the BMPs or their fragments. The selected hybrid cell contains sequences encoding both selected BMPs, and the heterodimer is formed in the cell and then secreted. The heterodimer is obtained from the conditioned medium and isolated and purified therefrom by conventional methods (see e.g., Example 4). The resulting heterodimer may be characterized by methods described herein.

Cell lines generated from the approaches described above can be used to produce co-expressed, heterodimeric BMP polypeptides. The heterodimeric proteins are isolated from the cell medium in a form substantially free from other proteins with which they are co-produced as well as from other contaminants found in the host cells by conventional purification techniques. The presently preferred method of production is co-transfection of different vectors into CHO cells and methotrexate-mediated gene amplification. Stable cell lines may be used to generate conditioned media containing recombinant BMP that can be purified and assayed for in vitro and in vivo activities. For example, the resulting heterodimer-producing cell lines obtained by any of the methods described herein may be screened for activity by the assays described in Examples 8 and 9, RNA expression, and protein expression by sodium dodecyl sulfate polyacrylamide gel electrophoresis (SDS-PAGE).

The above-described methods of co-expression of the heterodimers of this invention utilize suitable host cells or cell lines suitable cell preferably include mammalian cells, such as Chinese hamster ovary cells (CHO). The selection of suitable mammalian host cells and methods for transformation, culture, amplification, screening and product production and purification are known in the art. See, e.g., Gething and Sambrook, *Nature,* 293:620-625 (1981), or alternatively, Kaufman et al, *Mol. Cell. Biol.,* 5(7):1750-1759 (1985) or Howley et al, U.S. Pat. No. 4,419,446. Other suitable mammalian cell lines are the CV-1 cell line, BHK cell lines and the 293 cell line. The monkey COS-1 cell line is presently believed to be inefficient in BMP heterodimer production.

Many strains of yeast cells known to those skilled in the art may also be available as host cells for expression of the polypeptides of the present invention, e.g., *Saccharomyces cerevisiae.* Additionally, where desired, insect cells may be utilized as host cells in the method of the present invention. See, e.g., Miller et al, *Genetic Engineering,* 8:277-298 (Plenum Press 1986) and references cited therein.

Another method for producing a biologically active heterodimeric protein of this invention may be employed where the host cells are microbial, preferably bacterial cells, in particular *E. coli.* For example, the various strains of *E. coli* (e.g., HB101, MC1061) are well-known as host cells in the field of biotechnology. Various strains of *B. subtilis,* Pseudomonas, other bacilli and the like may also be employed in this method.

This method, which may be employed to produce monomers and dimers (both homodimers and heterodimers) is described in European Patent Application No. 433,225, incorporated herein by reference. Briefly, this process involves culturing a microbial host comprising a nucleotide sequence encoding the desired BMP protein linked in the proper reading frame to an expression control sequence which permits expression of the protein and recovering the monomeric, soluble protein. Where the protein is insoluble in the host cells, the water-insoluble protein fraction is isolated from the host cells and the protein is solubilized. After chromatographic purification, the solubilized protein is subjected to selected conditions to obtain the biologically active dimeric configuration of the protein. This process, which may be employed to produce the heterodimers of this invention, is described specifically in Example 7, for the production of a BMP-2 homodimer.

Another aspect of the present invention provides DNA molecules or plasmid vectors for use in expression of these recombinant heterodimers. These plasmid vectors may be constructed by resort to known methods and available components known to those of skill in the art. In general, to generate a vector useful in the methods of this invention, the DNA encoding the desired BMP protein is transferred into one or more appropriate expression vectors suitable for the selected host cell.

It is presently contemplated that any expression vector suitable for efficient expression in mammalian cells may be employed to produce the recombinant heterodimers of this invention in mammalian host cells. Preferably the vectors contain the selected BMP DNA sequences described above and in the Figures, which encode selected BMP components of the heterodimer. Alternatively, vectors incorporating modified sequences as described in the above-referenced patent applications are also embodiments of the present invention and useful in the production of the vectors.

In addition to the specific vectors described in Example 1, one skilled in the art can construct mammalian expression vectors by employing the sequence of FIGS. 1-6 or other DNA sequences containing the coding sequences of FIGS. 1-6 (SEQ ID NOs: 1, 3, 5, 7, 9 and 11), or other modified sequences and known vectors, such as pCD [Okayama et al, *Mol. Cell Biol.,* 2:161-170 (1982)] and pJL3, pJL4 [Gough et al, *EMBO J.,* 4:645-653 (1985)]. The BMP DNA sequences can be modified by removing the non-coding nucleotides on the 5' and 3' ends of the coding region. The deleted non-coding nucleotides may or may not be replaced by other sequences known to be beneficial for expression. The transformation of these vectors into appropriate host cells as described above can produce desired heterodimers.

One skilled in the art could manipulate the sequences of FIGS. 1-6 by eliminating or replacing the mammalian regulatory sequences flanking the coding sequence with e.g., yeast or insect regulatory sequences, to create vectors for intracellular or extracellular expression by yeast or insect cells. [See, e.g., procedures described in published European Patent Application 155,476] for expression in insect cells; and procedures described in published PCT application WO86/00639 and European Patent Application EPA 123,289 for expression in yeast cells].

Similarly, bacterial sequences and preference codons may replace sequences in the described and exemplified mammalian vectors to create suitable expression systems for use in the production of BMP monomers in the method described above. For example, the coding sequences could be further manipulated (e.g., ligated to other known linkers or modified by deleting non-coding sequences therefrom or altering nucleotides therein by other known techniques). The modified BMP coding sequences could then be inserted into a known bacterial vector using procedures such as described in T. Taniguchi et al, *Proc. Natl. Acad. Sci. USA,* 77:5230-5233 (1980). The exemplary bacterial vector could then be transformed into bacterial host cells and BMP heterodimers expressed thereby. An exemplary vector for microbial, e.g., bacterial, expression is described below in Example 7.

Other vectors useful in the methods of this invention may contain multiple genes in a single transcription unit. For example, a proposed plasmid p7E2D contains the BMP-7 gene followed by the EMC leader sequence, followed by the BMP-2 gene, followed by the DHFR marker gene. Another example is plasmid p7E2ED which contains the BMP-7 gene, the EMC leader, the BMP-2 gene, another EMC leader sequence and the DHFR marker gene. Alternatively, the vector may contain more than one transcription unit. As one example, the plasmid p2ED7ED contains a transcription unit for BMP-2 and a separate transcription unit for BMP-7, i.e., BMP-2-EMC-DHFR and BMP-7-EMC-DHFR. Alternatively, each transcription unit on the plasmid may contain a different marker gene. For example, plasmid p2EN7ED contains BMP-2-EMC-Neo and BMP-7-EMC-DHFR.

Additionally the vectors also contain appropriate expression control sequences which are capable of directing the replication and expression of the BMP in the selected host cells. Useful regulatory sequences for such vectors are known to one of skill in the art and may be selected depending upon the selected host cells. Such selection is routine and does not form part of the present invention. Similarly, the vectors may contain one or more selection markers, such as the antibiotic resistance gene, Neo or selectable markers such as DHFR and ADA. The presently preferred marker-gene is DHFR. These marker genes may also be selected by one of skill in the art.

Once they are expressed by one of the methods described above, the heterodimers of this invention may be identified and characterized by application of a variety of assays and procedures. A co-precipitation (immunoprecipitation) assay may be performed with antibodies to each of the BMPs forming the heterodimer. Generally antibodies for this use may be developed by conventional means, e.g., using the selected BMP, fragments thereof, or synthetic BMP peptides as antigen. Antibodies employed in assays are generally polyclonal antibodies made from individual BMP peptides or proteins injected into rabbits according to classical techniques. This assay is performed conventionally, and permits the identification of the heterodimer, which is precipitated by antibodies to both BMP components of the heterodimer. In contrast, only one of the two antibodies causes precipitation of any homodimeric form which may be produced in the process of producing the heterodimer.

Another characterizing assay is a Western assay, employing a precipitating antibody, a probing antibody and a detecting antibody. This assay may also be performed conventionally, by using an antibody to one of the BMPs to precipitate the dimers, which are run on reducing SDS-PAGE for Western analysis. An antibody to the second BMP is used to probe the precipitates on the Western gel for the heterodimer. A detecting antibody, such as a goat-antirabbit antibody labelled with horseradish peroxidase (HRP), is then applied, which will reveal the presence of one of the component subunits of the heterodimer.

Finally, the specific activity of the heterodimer may be quantitated as described in detail in Example 6. Briefly, the amount of each BMP is quantitated using Western blot analysis or pulse labelling and SDS-PAGE analysis in samples of each BMP homodimer and the heterodimer. The W20 activity is also determined as described specifically in Example 8. The relative specific activities may be calculated by the formula: W20 alkaline phosphatase activity/amount of BMP on Western blot or by fluorography. As one example, this formula has been determined for the BMP-2/7 heterodimer, demonstrating that the heterodimer has an estimated 5 to 50 fold higher specific activity than the BMP-2 homodimer.

The heterodimers of the present invention may have a variety of therapeutic and pharmaceutical uses, e.g., in compositions for wound healing, tissue repair, and in similar compositions which have been indicated for use of the individual BMPs. Increased potency of the heterodimers over the individual BMPs may permit lower dosages of the compositions in which they are contained to be administered to a patient in comparison to dosages of compositions containing only a single BMP. A heterodimeric protein of the present invention, which induces cartilage and/or bone growth in circumstances where bone is not normally formed, has application in the healing of bone fractures and cartilage defects in humans and other animals. Such a preparation employing a heterodimeric protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A heterodimeric protein of this invention may be used in the treatment of periodontal disease, and in other tooth repair processes. Such agents may provide an environment to attract bone-forming cells, stimulate growth of bone-forming cells or induce differentiation of progenitors of bone-forming cells. Heterodimeric polypeptides of the invention may also be useful in the treatment of osteoporosis. A variety of osteogenic, cartilage-inducing and bone inducing factors have been described. See, e.g., European Patent Applications 148, 155 and 169,016 for discussions thereof.

The proteins of the invention may also be used in wound healing and related tissue repair. The types of wounds include, but are not limited to burns, incisions and ulcers. (See, e.g., PCT Publication WO84/01106 incorporated by reference herein for discussion of wound healing and related tissue repair).

Additionally, the proteins of the invention may increase neuronal survival and therefore be useful in transplantation and treatment of conditions exhibiting a decrease in neuronal survival.

In view of the usefulness of the heterodimers, therefore, a further aspect of the invention is a therapeutic method and composition for repairing fractures and other conditions related to cartilage and/or bone defects or periodontal diseases. In addition, the invention comprises therapeutic methods and compositions for wound healing and tissue repair. Such compositions comprise a therapeutically effective amount of a heterodimeric protein of the invention in admixture with a pharmaceutically acceptable vehicle, carrier or matrix. The preparation and formulation of such physiologically acceptable protein compositions, having due regard to pH, isotonicity, stability and the like, is within the skill of the art.

It is expected that the proteins of the invention may act in concert with other related proteins and growth factors. Therapeutic methods and compositions of the invention therefore comprise a therapeutic amount of a heterodimeric protein of the invention with a therapeutic amount of at least one of the other BMP proteins disclosed in co-owned and concurrently filed U.S. applications described above. Such combinations may comprise separate molecules of the BMP proteins or other heteromolecules of the present invention.

In further compositions, heterodimeric proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications due to the lack of species specificity in BMP proteins. Particularly domestic animals and thoroughbred horses, in addition to humans, are desired patients for such treatment with heterodimeric proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the heterodimeric proteins of the invention which may also optionally be included in the composition as described above, may alternatively or additionally, be administered simultaneously or sequentially with the heterodimeric BMP composition in the methods of the invention. Preferably for bone and/or cartilage formation, the composition would include a matrix capable of delivering the heterodimeric protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the heterodimeric BMP compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applicatons, it will be useful to utilize a sequestering agent, such as carboxymethyl cellulose or autologous blood clot, to prevent the BMP compositions from dissassociating from the matrix.

The dosage regimen of a heterodimeric protein-containing pharmaceutical composition will be determined by the attending physician considering various factors which modify the action of the heterodimeric proteins, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the BMP proteins in the heterodimer and any additional BMP or other proteins in the pharmaceutical composition. For example, the addition of other known growth factors, such as IGF I (insulin like growth factor I), to the final composition, may also effect the dosage. Progress can be monitored by periodic assessment of bone growth and/or repair, for example, X-rays, histomorphometric determinations and tetracycline labeling.

The following examples are illustrative of the present invention and do not limit its scope.

Example 1

BMP Vector Constructs and Cell Lines

A. BMP-2 Vectors

The mammalian expression vector pMT2 CXM is a derivative of p91023 (b) [Wong et al, science, 228:810-815 (1985)] differing from the latter in that it contains the ampicillin resistance gene (Amp) in place of the tetracycline resistance gene (Tet) and further contains a XhoI site for insertion of cDNA clones. The functional elements of pMT2 CXM have been described [R. J. Kaufman, Proc. Natl. Acad. Sci. USA, 82:689-693 (1985)] and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

EcoRI digestion of pMT2-VWF, which has been deposited with the American Type Culture Collection (ATCC), Rockville, Md. (USA) under accession number ATCC 67122, excises the cDNA insert present in pMT2-VWF, yielding pMT2 in linear form. Plasmid pMT2 can be ligated and used to transform E. coli HB 101 or DH-5 to ampicillin resistance. Plasmid pMT2 DNA can be prepared by conventional methods.

Plasmid pMT2 CXM is then constructed using loopout/in mutagenesis [Morinaga et al, Biotechnology, 84:636 (1984)]. This removes bases 1075 to 1145 relative to the HindIII site near the SV40 origin of replication and enhancer sequences of pMT2. In addition it inserts the following sequence:

5' $PO_4$-CATGGGCAGCTCGAG-3' (SEQ ID NO: 15) at nucleotide 1145. This sequence contains the recognition site for the restriction endonuclease XhoI.

A derivative of pMT2 CXM, termed plasmid pMT23, contains recognition sites for the restriction endonucleases PstI, EcoRI, SalI and XhoI.

Full length BMP-2 cDNA (FIG. 1) (SEQ ID NO: 1) is released from the λGT10 vector by digestion with EcoRI and subcloned into pSP65 [Promega Biotec, Madison, Wis.; see, e.g., Melton et al, Nucl. Acids Res., 12:7035-7056 (1984)] in both orientations yielding pBMP-2 #39-3 or pBMP-2 #39-4.

The majority of the untranslated regions of the BMP-2 cDNA are removed in the following manner. The 5' sequences are removed between the SalI site in the adapter (present from the original cDNA cloning) and the SalI site 7 base pairs upstream of the initiator ATG by digestion of the pSP65 plasmid containing the BMP-2 cDNA with SalI and religation. The 3' untranslated region is removed using heteroduplex mutagenesis using the oligonucleotide (SEQ ID NO: 16)
5' GAGGGTTGTGGGTGTCGC<u>TAGTGAGTCGAC</u>TACAGCAAATT 3'.
                                            End    SalI The sequence contains the terminal 3' coding region of the BMP-2 cDNA, followed immediately by a recognition site for SalI. The sequence introduces a SalI site following the termination (TAG) codon.

The SalI fragment of this clone was subcloned into the expression vector pMT23, yielding the vector pMT23-

BMP2ΔUT. Restriction enzyme sites flank the BMP-2 coding region in the sequence PstI-EcoRI-SalI-BMP-2 cDNA-SalI-EcoRI-XhoI.

The expression plasmid pED4 [Kaufman et al, *Nucl. Acids Res.*, 19:4485-4490 (1991)] was linearized by digestion with EcoRI and treated with calf intestinal phosphatase. The BMP-2 cDNA gene was excised from pMT23-BMP2ΔUT by digestion with EcoRI and recovery of the 1.2 kb fragment by electrophoresis through a 1.0% low melt agarose gel. The linearized pED4 vector and the EcoRI BMP-2 fragment were ligated together, yielding the BMP-2 expression plasmid pBMP2Δ-EMC.

Another vector pBMP-2Δ-EN contains the same sequences contained within the vector pBMP2Δ-EMC, except the DHFR gene has been replaced by conventional means with the neomycin resistance gene from the Tn5 transposable element.

B. BMP4 Vectors

A BMP-4 cDNA sequence set forth in FIG. 2 (SEQ ID NO: 3), in which the 3' untranslated region is removed, is made via heteroduplex mutagenesis with the mutagenic oligonucleotide:

```
                                            (SEQ ID NO: 17)
5' GGATGTGGGTGCCGCTGACTCTAGAGTCGACGGAATTC 3'
                  End                EcoRI
```

This deletes all of the sequences 3' to the translation terminator codon of the BMP-4 cDNA, juxtaposing this terminator codon and the vector polylinker sequences. This step is performed in an SP65 vector [Promega Biotech] and may also be conveniently performed in pMT2-derivatives containing the BMP-4 cDNA similar to the BMP2 vectors described above. The 5' untranslated region is removed using the restriction endonuclease BsmI, which cleaves within the eighth codon of BMP-4 cDNA.

Reconstruction of the first eight codons is accomplished by ligation to oligonucleotides:

```
                                            (SEQ ID NO: 18)
        EcoRI    Initiator            BsmI
    5'  AATTCACCATGATTCCTGGTAACCGAATGCT     3'
and (SEQ ID NO: 19)
    3'        GTGGTACTAAGGACCATTGGCTTAC     5'
```

These oligonucleotides form a duplex which has a BsmI complementary cohesive end capable of ligation to the BsmI restricted BMP-4 cDNA, and it has an EcoRI complementary cohesive end capable of ligation to the EcoRI restricted vector pMT2. Thus the cDNA for BMP-4 with the 5' and 3' untranslated regions deleted, and retaining the entire encoding sequence is contained within an EcoRI restriction fragment of approximately 1.2 kb.

The pMT2 CXM plasmid containing this BMP-4 sequence is designated pXMBMP-4ΔUT. It is digested with EcoRI in order to release the BMP-4 cDNA containing insert from the vector. This insert is subcloned into the EcoRI site of the mammalian expression vector pED4, resulting pBMP4Δ-EMC.

C. BMP-5 Vectors

A BMP-5 cDNA sequence comprising the nucleotide sequence from nucleotide #699 to #2070 of FIG. 5 (SEQ ID NO: 9) is specifically amplified as follows. The oligonucleotides CGACCTGCAGCCACCATGCATCTGACTGTA (SEQ ID NO: 20) and TGCCTGCAGTTTAATATTAGTG-GCAGC (SEQ ID NO: 21) are utilized as primers to allow the amplification of nucleotide sequence #699 to #2070 of FIG. 5 from the BMP-5 insert of λ-ZAP clone U2-16 [ATCC #68109]. This procedure introduces the nucleotide sequence CGACCTGCAGCCACC (SEQ ID NO: 22) immediately preceeding nucleotide #699 and the nucleotide sequence CTGCAGGCA immediately following nucleotide #2070. The addition of these sequences results in the creation of PstI restriction endonuclease recognition sites at both ends of the amplified DNA fragment. The resulting amplified DNA product of this procedure is digested with the restriction endonuclease PstI and subcloned into the PstI, site of the pMT2 derivative pMT21 [Kaufman, *Nucl. Acids Res.*, 19:4485-4490 (1991)]. The resulting clone is designated H5/5/pMT.

The insert of H5/5/pMT is excised by PstI digestion and subcloned into the plasmid vector pSP65 [Promega Biotech] at the PstI site, resulting in plasmid BMP5/SP6. BMP5/SP6 and U2-16 are digested with the restriction endonucleases NsiI and NdeI to excise the portion of their inserts corresponding to nucleotides #704 to #1876 of FIG. 5. The resulting 1173 nucleotide NsiI-NdeI fragment of clone U2-16 is ligated into the NsiI-NdeI site of BMP5/SP6 from which the corresponding 1173 nucleotide NsiI-NdeI fragment had been removed. The resulting clone is designated BMP5mix/SP65.

Direct DNA sequence analysis of BMP5mix/SP65 is performed to confirm identity of the nucleotide sequences produced by the amplification to those set forth in FIG. 5. The clone BMP5mix/SP65 is digested with the restriction endonuclease PstI resulting in the excision of an insert comprising the nucleotides #699 to #2070 of FIG. 5 and the additional sequences containing the PstI recognition sites as described above. The resulting 1382 nucleotide PstI fragment is subcloned into the PstI site of the pMT2 derivative pMT21. This clone is designated BMP5mix/pMT21#2.

The same fragment is also subcloned into the PstI site of pED4 to yield the vector designated BMP5mix-EMC-11.

D. BMP-6 Vectors

A BMP-6 cDNA sequence comprising the nucleotide sequence from nucleotide #160 to #1706 of FIG. 4 (SEQ ID NO: 7) is produced by a series of techniques known to those skilled in the art. The clone BMP6C35 [ATCC 68245] is digested with the restriction endonucleases ApaI and TaqI, resulting in the excision of a 1476 nucleotide portion of the insert comprising nucleotide #231 to #1703 of FIG. 4. Synthetic oligonucleotides with SalI restriction endonuclease site converters are designed to replace those nucleotides corresponding to #160 to #230 and #1704 to #1706 which are not contained in the 1476 ApaI-TaqI fragment of the BMP-6 cDNA sequence.

Oligonucleotide/SalI converters conceived to replace the missing 5' (TCGACCCACCATGCCGGGGCTGGGGCG-GAGGGCGCAGTGGCTGTGCTGGTG-GTGGGGGCTGTGCTGCAGCTGCTGCGGGCC (SEQ ID NO: 23) and CGCAGCAGCTGCACAGCAGC-CCCCACCACCAGCACAGCCACTGCGC-CCTCCGCCCCAGCCCCGGCATGGTGGG) (SEQ ID NO: 24) and 3' (TCGACTGGTTT (SEQ ID NO: 25) and CGAAACCAG (SEQ ID NO: 26)) sequences are annealed to each other independently. The annealed 5' and 3' converters are then ligated to the 1476 nucleotide ApaI-TaqI described above, creating a 1563 nucleotide fragment comprising the nucleotide sequence from #160 to #1706 of FIG. 4 and the additional sequences contrived to create SalI restriction endonuclease sites at both ends. The resulting 1563 nucleotide fragment is subcloned into the SalI site of pSP64 [Promega Biotech, Madison, Wis.]. This clone is designated BMP6/SP64#15.

DNA sequence analysis of BMP6/SP64#15 is performed to confirm identity of the 5' and 3' sequences replaced by the converters to the sequence set forth in FIG. 4. The insert of BMP6/SP64#15 is excised by digestion with the restriction endonuclease SalI. The resulting 1563 nucleotide SalI fragment is subcloned into the XhoI restriction endonuclease site of pMT21 and designated herein as BMP6/pMT21.

The PstI site of pED4 is converted to a SalI site by digestion of the plasmid with PstI and ligation to the converter oligonucleotides:

```
5'-TCGACAGGCTCGCCTGCA-3'      (SEQ ID NO: 27) and

3'-GTCCGAGCGG-5'              (SEQ ID NO: 28).
```

The above 1563 nucleotide SalI fragment is also subcloned into the SalI site of this pED4 vector, yielding the expression vector BMP6/EMC.

E. BMP-7 Vectors

A BMP-7 sequence comprising the nucleotide sequence from nucleotide #97 to #1402 of FIG. 3 (SEQ ID NO: 5) is specifically amplified as follows. The oligonucleotides GAGGTCGACCCACCATGCAGGTGCGCTCA (SEQ ID NO: 29) and TCTGTCGACCTGGGAGGAGGTAGTGGC (SEQ ID NO: 30) are utilized as primers to allow the amplification of nucleotide sequence #97 to #1402 of FIG. 3 from the insert of clone PEH7-9 [ATCC #68182]. This procedure generates the insertion of the nucleotide sequence GAGGTCGACCCACC (SEQ ID NO: 31) immediately preceeding nucleotide #97 and the insertion of the nucleotide sequence GTCGACAGA immediately following nucleotide #1402. The addition of these sequences results in the creation of a SalI restriction endonuclease recognition site at each end of the amplified DNA fragment. The resulting amplified DNA product of this procedure is digested with the restriction endonuclease SalI and subcloned into the SalI site of the plasmid vector pSP64 [Promega Biotech, Madison, Wis.] resulting in BMP7/SP6#2.

The clones BMP7/SP6#2 and PEH7-9 are digested with the restriction endonucleases NcoI and StuI to excise the portion of their inserts corresponding to nucleotides #363 to #1081 of FIG. 3. The resulting 719 nucleotide NcoI-StuI fragment of clone PEH7-9 is ligated into the NcoI-StuI site of BMP7/SP6#2 from which the corresponding 719 nucleotide fragment is removed. The resulting clone is designated BMP7mix/SP6.

Direct DNA sequence analysis of BMP7mix/SP6 confirmed identity of the 3' region to the nucleotide sequence from #1082 to #1402 of FIG. 3, however the 5' region contained one nucleotide misincorporation.

Amplification of the nucleotide sequence (#97 to #1402 of FIG. 3) utilizing PEH7-9 as a template is repeated as described above. The resulting amplified DNA product of this procedure is digested with the restriction endonucleases SalI and PstI. This digestion results in the excision of a 747 nucleotide fragment comprising nucleotide #97 to #833 of FIG. 3 plus the additional sequences of the 5' priming oligonucleotide used to create the SalI restriction endonuclease recognition site described earlier. This 747 SalI-PstI fragment is subcloned into a SalI-PstI digested pSP65 [Promega Biotech, Madison, Wis.] vector resulting in 5'BMP7/SP65. DNA sequence analysis demonstrates that the insert of the 5'BMP7/SP65#1 comprises a sequence identical to nucleotide #97 to #362 of FIG. 3.

The clones BMP7mix/SP6 and 5'BMP7/SP65 are digested with the restriction endonucleases SalI and NcoI. The resulting 3' NcoI-SalI fragment of BMP7mix/SP6 comprising nucleotides #363 to #1402 of FIG. 3 and 5' SalI-NcoI fragment of 5'BMP7/SP65 comprising nucleotides #97 to #362 of FIG. 3 are ligated together at the NcoI restriction sites to produce a 1317 nucleotide fragment comprising nucleotides #97 to #1402 of FIG. 3 plus the additional sequences derived from the 5' and 3' oligonucleotide primers which allows the creation of SalI restriction sites at both ends of this fragment.

This 1317 nucleotide SalI fragment is ligated nto the SalI site of the pMT2 derivative pMT2Cla-2. pMT2Cla-2 is constructed by digesting pMT21 with EcoRV and XhoI, treating the digested DNA with Klenow fragment of DNA polymerase I and ligating ClaI linkers (NEBio Labs, CATCGATG). This removes bases 2171 to 2420 starting from the HindIII site near the SV40 origin of replication and enhancer sequences of pMT2 and introduces a unique ClaI site, but leaves the adenovirus VAI gene intact, resulting in pMT2Cla-2. This clone is designated BMP-7-pMT2.

The insert of BMP-7-pMT2 is excised by digestion with the restriction endonuclease SalI. The resulting 1317 nucleotide SalI fragment is subcloned into the XhoI restriction endonuclease site of pMT21 to yield the clone BMP-7/pMT21. This SalI fragment is also subcloned into the SalI site of the pED4 vector in which the PstI site was converted into a SalI site as described above, resulting in the vector pBMP7/EMC#4.

F. BMP-8 Vectors

At present no mammalian BMP-8 vectors have been constructed. However, using the sequence of FIG. 6 (SEQ ID NO: 11), it is contemplated that vectors similar to those described above for the other BMPs may be readily constructed. A bacterial expression vector similar to the BMP-2 vector described in detail in Example 7 may also be constructed for BMP-8, by introducing a Met before the amino acid #284 Ala of FIG. 6. This sequence of BMP-8 is inserted into the vector pALBP2-781 in place of the BMP-2 sequence. See Example 7.

G. BMP Vectors Containing the Adenosine Deaminase (Ada) Marker

BMP genes were inserted into the vector pMT3SV2Ada [R. J. Kaufman, Meth. Enz., 185:537-566 (1990)] to yield expression plasmids containing separate transcription units for the BMP cDNA gene and the selectable marker Ada. pMT3SV2Ada contains a polylinker with recognition sites for the enzymes PstI, EcoRI, SalI and XbaI that can be used for insertion of and expression of genes (i.e. BMP) in mammalian cells. In addition, the vector contains a second transcription unit encoding Ada which serves as a dominant and amplifiable marker in mammalian cells.

To construct expression vectors for BMP-5, BMP-6 and BMP-7, individually, the same general method was employed. The gene for BMP 5 (FIG. 5), 6 (FIG. 4) or 7 (FIG. 3) was inserted into the polylinker essentially as described above for the pED4 vector. These vectors can be used for transfection into CHO DUKX cells and subsequent selection and amplification using the Ada marker as previously described [Kaufman et al, Proc. Natl. Acad. Sci. USA, 83:3136-3140 (1986)]. Since each such vector does not contain a DHFR gene, the resultant transformed cells remain DHFR negative and can be subsequently transfected with a second vector containing a different BMP in conjunction with DHFR and amplified with methotrexate.

Alternatively, the pMT3SV2Ada/BMP vectors can be used to transfect stable CHO cell lines previously transfected with a different BMP gene and amplified using the DHFR/methotrexate system. The resultant transfectants can be subsequently amplified using the Ada system, yielding cell lines that coexpress two different BMP genes, and are amplified using both the DHFR and Ada markers.

H. BMP-Expressing Mammalian Cell Lines

At present, the most desirable mammalian cell lines for use in producing the recombinant homodimers and heterodimers of this invention are the following. These cell lines were prepared by conventional transformation of CHO cells using vectors described above.

The BMP-2 expressing cell line 2EG5 is a CHO cell stably transformed with the vector pBMP2delta-EMC.

The BMP-4 expressing cell line 4E9 is a CHO cell stably transformed with the vector pBMP4delta-EMC.

The BMP-5 expressing cell line 5E10 is a CHO cell stably transformed with the vector BMP5mix-EMC-11 (at a amplification level of 2 micromolar MTX).

The BMP-6 expressing cell line 6HG8 is a CHO cell stably transformed with the vector BMP6/EMC.

The BMP-7 expressing cell line 7 MB9 is a CHO cell stably transformed with the vector BMP7/pMT21.

Example 2

Transient Expression of BMP Heterodimers

The heterodimers of the present invention may be prepared by co-expression in a transient expression system for screening in the assays of Example 8 by two different techniques as follows.

In the first procedure, the pMT2-derived and EMC-derived expression plasmids described in Example 1 and other similarly derived vectors were constructed which encoded, individually, BMP-2 through BMP-7, and transforming growth factor-beta (TGFβ1). All combinations of pairs of plasmids were mixed in equal proportion and used to co-transfect CHO cells using the DEAE-dextran procedure [Sompayrac and Danna, *Proc. Natl. Acad. Sci. USA*, 78:7575-7578 (1981); Luthman and Magnusson, *Nucl. Acids Res.*, 11:1295-1308 (1983)]. The cells are grown in alpha Minimal Essential Medium (α-MEM) supplemented with 10% fetal bovine serum, adenosine, deoxyadenosine, thymidine (100 µg/ml each), pen/strep, and glutamine (1 mM).

The addition of compounds such as heparin, suramin and dextran sulfate are desirable in growth medium to increase the amounts of BMP-2 present in the conditioned medium of CHO cells. Similarly responsive to such compounds is BMP-5. Therefore, it is expected that these compounds will be added to growth medium for any heterodimer containing these BMP components. Other BMPs may also be responsive to the effects of these compounds, which are believed to inhibit the interaction of the mature BMP molecules with the cell surface.

The following day, fresh growth medium, with or without 100 µg/ml heparin, was added. Twenty-four hours later, conditioned medium was harvested.

In some experiments, the conditioned medium was collected minus heparin for the 24-48 hour period post-transfection, and the same plates were then used to generate conditioned medium in the presence of heparin 48-72 hour post-transfection. Controls included transfecting cells with expression plasmids lacking any BMP sequences, transfecting cells with plasmids containing sequences for only a single BMP, or mixing conditioned medium from cells transfected with a single BMP with conditioned medium from cells transfected with a different BMP.

Characterizations of the coexpressed heterodimer BMPs in crude conditioned media, which is otherwise not purified, provided the following results. Transiently coexpressed BMP was assayed for induction of alkaline phosphatase activity on W20 stromal cells, as described in Example 8.

Co-expression of BMP-2 with BMP-5, BMP-6 and BMP-7, and BMP-4 with BMP-5, BMP-6 and BMP-7 yielded more alkaline phosphatase inducing activity in the W20 assay than either of the individual BMP homodimers alone or mixtures of homodimers, as shown below. Maximal activity (in vitro), was obtained when BMP-2 was coexpressed with BMP-7. Increased activity was also found the heterodimers BMP-2/5; BMP-2/6; BMP-4/5; BMP-4/6; and BMP-4/7.

|       | TGF-β | BMP-7 | BMP-6 | BMP-5 | BMP-4 | BMP-3 | BMP-2 |
|-------|-------|-------|-------|-------|-------|-------|-------|
|       |       |       | Condition Medium |   |    |   |   |
| BMP-2 | 33    | 240   | 99    | 89    | 53    | 9     | 29    |
| BMP-3 | —     | —     | —     | —     | 14    | —     |       |
| BMP-4 | 12    | 115   | 25    | 22    | 24    |       |       |
| BMP-5 | —     | —     | —     | —     |       |       |       |
| BMP-6 | —     | —     |       |       |       |       |       |
| BMP-7 | —     | —     |       |       |       |       |       |
| TGF-β | —     |       |       |       |       |       |       |
|       |       |       | Condition Medium + heparin |   |   |   |   |
| BMP-2 | 88    | 454   | 132   | 127   | 70    | 77    | 169   |
| BMP-3 | —     | —     | —     | —     | 7     | —     |       |
| BMP-4 | 7     | 119   | 30    | 41    | 37    |       |       |
| BMP-5 | —     | —     | —     | —     |       |       |       |
| BMP-6 | —     | —     |       |       |       |       |       |
| BMP-7 | —     | —     |       |       |       |       |       |
| TGF-β |       |       |       |       |       |       |       |

Units: 1 unit of activity is equivalent to that of 1 ng/ml of rhBMP-2.
—: indicates activity below the detection limit of the assay.

These BMP combinations were subsequently expressed using various ratios of expression plasmids (9:1, 3:1, 1:1, 1:3, 1:9) during the CHO cell transient transfection. The performance of this method using plasmids containing BMP-2 and plasmids containing BMP-7 at plasmid number ratios ranging from 9:1 to 1:9, respectively, demonstrated that the highest activity in the W20 assay was obtained when approximately the same number of plasmids of each BMP were transfected into the host cell. Ratios of BMP-2 to BMP-7 plasmids of 3:1 to 1:3, respectively, also resulted in increased activity in W20 assay in comparison to host cells transfected with plasmids containing only a single BMP. However, these latter ratios produced less activity than the 1:1 ratio.

Similar ratios may be determined by one of skill in the art for heterodimers consisting of other than BMP-2 and BMP-7. For example, preliminary work on the heterodimer formed between BMP-2 and BMP-6 has indicated that a preferred ratio of plasmids for co-transfection is 3:1, respectively. The determination of preferred ratios for this method is within the skill of the art.

As an alternative means to transiently generate coexpressed BMPs, the stable CHO cell lines identified in Example 1 expressing each BMP-2, BMP-4, BMP-5, BMP-6 and BMP-7, are cocultured for one day, and are then fused with 46.7% polyethylene glycol (PEG). One day post-fusion, fresh medium is added and the heterodimers are harvested 24 hours later for the W20 assay, described in Example 8. The assay results were substantially similar to those described immediately above.

Therefore, all combinations of BMP-2 or 4 coexpressed with either BMP-5, 6 or 7 yielded greater activity than any of the BMP homodimers alone. In control experiments where each BMP homodimer was expressed alone and conditioned media mixed post harvest, the activity was always intermediate between the individual BMPs, demonstrating that the BMP co-expressed heterodimers yield higher activity than combinations of the individually expressed BMP homodimers.

Example 3

Stable Expression of BMP Heterodimers

A. BMP-2/7

Based on the results of the transient assays in Example 2, stable cell lines were made that co-express BMP-2 and BMP-7.

A preferred stable cell line, 2E7E-10, was obtained as follows: Plasmid DNA (a 1:1 mixture of pBMP-7-EMC and pBMP-2-EMC, described in Example 1) is transfected into CHO cells by electroporation [Neuman et al, *EMBO J.*, 1:841-845 (1982)].

Two days later, cells are switched to selective medium containing 10% dialyzed fetal bovine serum and lacking nucleosides. Colonies expressing DHFR are counted 10-14 days later. Individual colonies or pools of colonies are expanded and analyzed for expression of each heterodimer BMP component RNA and protein using standard procedures and are subsequently selected for amplification by growth in increasing concentrations of MTX. Stepwise selection of the preferred clone, termed 2E7E, is carried out up to a concentration of 0.5 µM MTX. The cell line is then subcloned and assayed for heterodimer 2/7 expression.

Procedures for such assay include Western blot analysis to detect the presence of the component DNA, protein analysis and SDS-PAGE analysis of metabolically labelled protein, W20 assay, and analysis for cartilage and/or bone formation activity using the ectopic rat bone formation assay of Example 9. The presently preferred clonally-derived cell line is identified as 2E7E-10. This cell line secretes BMP-2/7 heterodimer proteins into the media containing 0.5 µM MTX.

The CHO cell line 2E7E-10 is grown in Dulbecco's modified Eagle's medium (DMEM)/Ham's nutrient mixture F-12, 1:1 (vol/vol), supplemented with 10% fetal bovine serum. When the cells are 80 to 100% confluent, the medium is replaced with serum-free DMEM/F-12. Medium is harvested every 24 hours for 4 days. For protein production and purification the cells are cultured serum-free.

While the co-expressing cell line 2E7E-10 preliminarily appears to make lower amounts of BMP protein than the BMP2-expressing cell line 2EG5 described in Example 2, preliminary evidence suggests that the specific activity of the presumptive heterodimer is at least 5-fold greater than BMP-2 homodimer (see Example 6).

To construct another heterodimer producing cell line, the stable CHO cell line 7 MB9, previously transfected with pBMP-7-pMT2, and which expresses BMP-7, is employed. 7 MB9 may be amplified and selected to 2 µM methotrexate resistance using the DHFR/MTX system. To generate a stable co-expressing cell line, cell line 7 MB9 is transfected with the expression vector pBMP-2Δ-EN (EMC-Neo) containing BMP-2 and the neomycin resistance gene from the Tn5 transposable element. The resulting transfected stable cell line was selected for both G-418 and MTX resistance. Individual clones were picked and analyzed for BMP expression, as described above.

It is anticipated that stable cell lines co-expressing other combinations of BMPs which show enhanced activity by transient coexpression will likewise yield greater activity upon stable expression.

B. BMP-2/6

Based on the results of the transient assays in Example 2, stable cell lines were made that co-express BMP-2 and BMP-6.

A preferred stable cell line, 12C07, was obtained as follows: Plasmid DNA (a 1:3 mixture of pBMP-6-EMC and pBMP-2-EMC, described in Example 1) is transfected into CHO cells by electroporation [Neuman et al, *EMBO J.*, 1:841-845 (1982)].

Two days later, cells are switched to selective medium containing 10% dialyzed fetal bovine serum and lacking nucleosides. Colonies expressing DHFR are counted 10-14 days later. Individual colonies or pools of colonies are expanded and analyzed for expression of each heterodimer BMP component RNA and protein using standard procedures and are subsequently selected for amplification by growth in increasing concentrations of MTX. Stepwise selection of the preferred clone, termed 12-C, is carried out up to a concentration of 2.0 µM MTX. The cell line is then subcloned and assayed for heterodimer 2/6 expression.

Procedures for such assay include Western blot analysis to detect the presence of the component DNA, protein analysis and SDS-PAGE analysis of metabolically labelled protein, W20 assay, and analysis for cartilage and/or bone formation activity using the ectopic rat bone formation assay of Example 9. The presently preferred clonally-derived cell line is identified as 12C07. This cell line secretes BMP-2/6 heterodimer proteins into the media containing 2.0 µM MTX.

The CHO cell line 12C07 is grown in Dulbecco's modified Eagle's medium (DMEM)/Ham's nutrient mixture F-12, 1:1 (vol/vol), supplemented with 10% fetal bovine serum. When the cells are 80 to 100% confluent, the medium is replaced with serum-free DMEM/F-12. Medium is harvested every 24 hours for 4 days. For protein production and purification the cells are cultured serum-free.

While the co-expressing cell line 12C07 preliminarily appears to make lower amounts of BMP protein than the BMP2-expressing cell line 2EG5 described in Example 2, preliminary evidence suggests that the specific activity of the presumptive heterodimer is at least 3-5-fold greater than BMP-2 homodimer (see Example 6).

To construct another heterodimer producing cell line, the stable CHO cell line 2EG5, previously transfected with pBMP-2-EMC, and which expresses BMP-2, is employed. 2EG5 may be amplified and selected to 2 µM methotrexate resistance using the DHFR/MTX system. To generate a stable co-expressing cell line, cell line 2EG5 is transfected with the expression vector pBMP-6-ada (ada deaminase) containing BMP-6 and the ADA resistance gene. The resulting transfected stable cell line was selected for both DCF and MTX resistance. Individual clones are picked and analyzed for EMP expression, as described above.

It is anticipated that stable cell lines co-expressing other combinations of BMPs which show enhanced activity by transient coexpression will likewise yield greater activity upon stable expression.

Example 4

Purification of BMP2/7 and BMP-2/6 Heterodimer

The same purification procedure is used for BMP-2/6 heterodimer and BMP-2/7 heterodimer. Conditioned media from cultures of cell line 2E7E-10 or 12C07 containing recombinantly produced BMP heterodimer 2/7V or 2/6, respectively, can be generated from either adherent or suspension cultures. For small to medium scale generation of coexpressed EMP, adherent cultures are seeded into roller bottles and allowed to grow to confluence in alpha-Minimal Eagles Medium [α-MEM, Gibco, Grand Island, N.Y.] containing 10% dialyzed heat-inactivated fetal calf serum [Hazleton, Denver, Pa.]. The media is then switched to a serum-free, albumin free, low protein medium based on a 50:50 mixture of Delbecco's Modified Eagle's medium and Hams F-12 medium, optionally supplemented with 100 micrograms/ml dextran sulfate. Four or five daily harvests are pooled, and used to purify the recombinant protein.

Conditioned medium from roller bottle cultures obtained as described above was thawed slowly at room temperature and pooled. The pH of the pooled medium was adjusted to pH 8.0 using 1 M Tris, pH 8.0. A column was poured containing Matrex Cellufine Sulfate [Amicon] and equilibrated in 50 mM Tris, pH 8.0.

Upon completion of loading of the medium, the column was washed with buffer containing 50 mM Tris, 0.4 M NaCl, pH 8.0 until the absorbance at 280 nm reached baseline. The column was then washed with 50 mM Tris, pH 8.0 to remove NaCl from the buffer. The resin was then washed with 50 mM Tris, 0.2 M NaCl, 4 M Urea, pH 8.0 until a peak had eluted. The column was then washed into 50 mM Tris, pH 8.0 to remove the urea.

The bound BMP-2/7 or BMP-2/6 was then eluted using 50 mM Tris, 0.5 M NaCl, 0.5 M Arginine, pH 8.0. The eluate was collected as a single pool and may be optionally stored frozen prior to further purification. This Cellufine Sulfate eluate was diluted with 14 volumes of 6M urea and the pH of the sample was then adjusted to 6.0. A hydroxyapatite-Ultrogel [IBF] column was poured and equilibrated with 80 mM potassium phosphate, 6M urea, pH 6.0.

After the completion of sample loading, the column was washed with 10 bed volumes of the equilibration buffer. Bound BMP-2/7 or BMP-2/6 heterodimers were eluted with 5 bed volumes of 100 mM potassium phosphate, 6M urea, pH 7.4. This eluate was loaded directly onto a Vydac $C_4$ reverse-phase HPLC column equilibrated in water –0.1% TFA. BMP-2/7 or BMP-2/6 heterodimers were eluted with a gradient of 30-50% acetonitrile in water—0.1% trifluoroacetic acid.

Fractions containing BMPs are identified by SDS-PAGE in the presence or absence of reductant. The identity of the BMPs with respect to the heterodimers vs. homodimers is determined by 2D-PAGE (+/−reductant). Fractions with heterodimers gave bands which reduce to two spots. Bands from homodimer fractions reduce to a single spot for each BMP species.

The BMP-2/6 heterodimer subunits are analyzed on a protein sequenator. BMP-2/6 heterodimers of the following species are present: BMP-6 subunit beginning with amino acid #375 Ser-Ala-Ser-Ser in association with BMP-2 subunit beginning with amino acid #283 Gin-Ala-Lys or #249 Ser-Lev-His, though other less abundant species may be present.

It is contemplated that the same or substantially similar purification techniques may be employed for any recombinant BMP heterodimer of this invention. The hydroxyapatite-Ultrogel column may be unnecessary and that the purification scheme may be modified by loading the Cellufine Sulfate eluate directly onto the C4 reverse-phase HPLC column without use of the former column for BMP2/7 or BMP-2/6 or the other heterodimers of this invention.

Example 5

Protein Characterization

Total protein secreted from the co-expressing cell lines is analyzed after labelling with $^{35}$S-methionine or by Western blot analysis using antibodies raised against both BMPs of the heterodimer, e.g., BMP-2 and BMP-7. Together with the alkaline phosphatase assays, the data indicates the presence of the heterodimer and the specific activity. The following specific details are directed towards data collected for the BMP-2/7 and BMP-2/6 heterodimers; however, by application of similar methods to the other heterodimers described herein, similar results are expected.

A. $^{35}$S-Met Labelling

Cell lines derived by cotransfection of BMP2$_A$-EMC and BMP7$_A$-EMC expression vectors were pulsed with $^{35}$S-methionine for 15 minutes, and chased for 6 hours in serum free media in the presence or absence of heparin. Total secreted protein was analyzed under reducing conditions by PAGE and fluorography. The results demonstrate that several cell lines secrete both BMP-2 and BMP-7 protein. There is a good correlation between the amount of alkaline phosphatase activity and the amount of coexpressed protein.

Several cell lines secrete less total BMP-2 and 7 than the BMP-2-only expressing cell line 2EG5, which produces 10 µg/ml BMP-2. Cell line 2E7E-10 (amplified at a level of 0.5 mM MTX) secretes equal proportions of BMP-2 and BMP-7 at about the same overall level of expression as the cell line 2EG5. Cell line 2E7E-10 produces the equivalent of 600 micrograms/ml of BMP-2 homodimer activity in one assay.

Total labelled protein was also analyzed on a two dimensional non-reducing/reducing gel system to ascertain whether a heterodimer is made. Preliminary results demonstrate the presence of a unique spot in this gel system that is not found in either the BMP-2-only or BMP-7-only cell lines, suggesting the presence of 2/7 heterodimer. The same gel with purified material produced the same results (e.g., two unique spots on the gel) indicative of the presence of the 2/7 heterodimer. The homodimer of BMP2 produced distinct species on this gel system.

In contrast to the recombinant BMP-2/7 purification, BMP-2 homodimers are not detected during the BMP-2/6 preparation; however, significant amounts of BMP-6 homodimers are found. In addition, a significant amount of a –20 amino acid N-terminal truncated form of BMP-6 is found; this could be eliminated by the inclusion of protease inhibitors during cell culture. BMP-2/6 was found to elute two to three fractions later from C4 RP-HPLC than did BMP-2/7.

B. Immunoprecipitation Coupled to Western Blot Analysis

Conditioned media from a BMP-2-only (2EG5), a BMP-7-only (7MB9), or the 2E7E-10 co-expressing cell line were subjected to immunoprecipitation with either a BMP-2 or BMP-7 antibody (both conventional polyclonal antibodies raised in rabbits), then analyzed on Western blots probed with either an anti-BMP-2 or anti-BMP-7 antibody. The 2/7 heterodimer precipitates and is reactive on Western blots with both the BMP-2 and BMP-7 antibodies, while either BMP by itself reacts with its specific antibody, but not with the reciprocal antibody.

It has been demonstrated using this strategy that a protein in the co-expressing cell line that is precipitated by the anti-BMP-7 antibody W33 [Genetics Institute, Inc, Cambridge, Mass.] and reacts on a Western blot with the anti-BMP-2 antibody W12 or W10 [Genetics Institute, Inc.] is not present in the BMP-2 or 7-only expressing cell lines. This experiment indicates that this protein species is the heterodimeric protein. Conversely, precipitation with W12 and probing with W33 yielded similar results.

Example 6

Specific Activity of Heterodimers

A. In Vitro Assays

The specific activity of the BMP-2/7 or BMP-2/6 heterodimer and the BMP-2 homodimer secreted into growth medium of the stable cell lines 2E7E-10 and 2EG55, and 12C07 and 2EG5, respectively, were estimated as follows.

The amount of BMP protein in conditioned medium was measured by either Western blot analysis or by analyzing protein secreted from $^{35}$S-methionine labelled cells by PAGE and fluorography. The amount of activity produced by the same cell lines on W20 cells using either the alkaline phosphatase assay or osteocalcin-induction assay was then estimated. The specific activity of the BMP was calculated from the ratio of activity to protein secreted into the growth medium.

In one experiment 2E7E-10 and 2EG5 secreted similar amounts of total BMP proteins as determined by PAGE and fluorography. 2E7E-10 produced about 50-fold more alkaline phosphatase inducing activity the 2EG5, suggesting that the specific activity of the heterodimer is about 50-fold higher than the homodimer.

In another experiment the amount of BMP-2 secreted by 2EG5 was about 50% higher than BMP-2/7 secreted by 2E7E-10, however, 2E7E-10 produced about 10-fold more osteocalcin-inducing activity that 2EG5. From several different experiments of this type the specific activity of the BMP-2/7 heterodimer is estimated to be between 5 to 50 fold higher than the BMP-2 homodimer.

Figure 8:
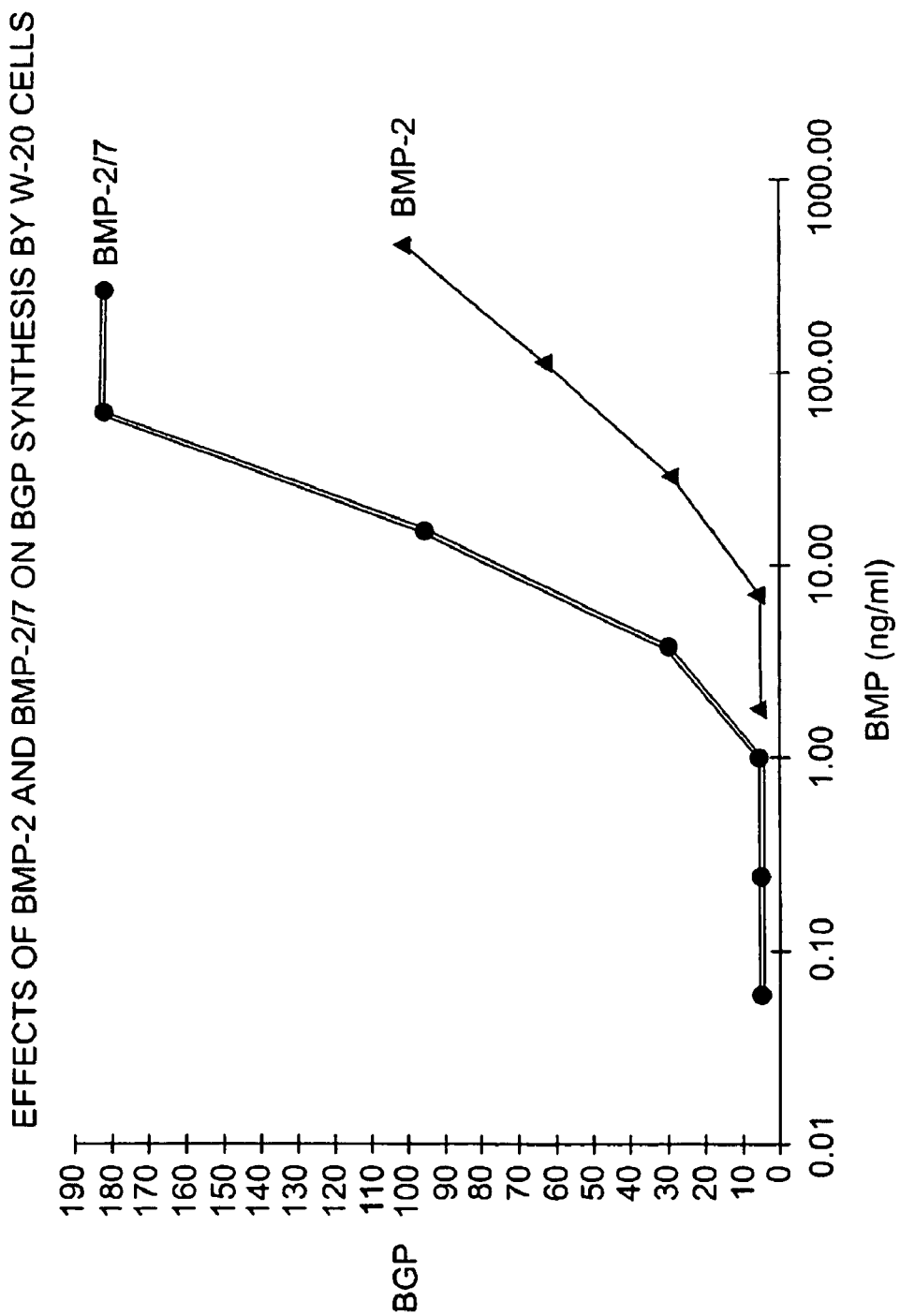
FIG. 8 compares the activity of CHO BMP-2 and CHO BMP-2/7 in the BGP (osteocalcin) assay.

FIGS. 7 and 8 compare the activity of BMP-2 and BMP-2/7 in the W20 alkaline phosphatase and BGP (Bone Gla Protein, osteocalcin) assays. BMP-2/7 has greatly increased specific activity relative to BMP-2 (FIG. 7). From FIG. 7, approximately 1.3 ng/ml of BMP-2/7 was sufficient to induce 50% of the maximal alkaline phosphatase response in W-20 cells. A comparable value for BMP-2 is difficult to calculate, since the alkaline phosphatase response did not maximize, but greater than 30 ng/ml is needed for a half-maximal response. BMP-2/7 thus has a 20 to 30-fold higher specific activity than BMP-2 in the W-20 assay.

As seen in FIG. 8, BMP-2/7 was also a more effective stimulator of BGP (bone gla protein, osteocalcin) production than BMP-2 in this experiment. Treating W-20-17 cells with BMP-2/7 for four days resulted in a maximal BGP response with 62 ng/ml, and 11 ng/ml elicits 50% of the maximal BGP response. In contrast, maximal stimulation of BGP synthesis by BMP-2 was not seen with doses up to 468 ng/ml of protein. The minimal dose of BMP-2/7 needed to elicit a BGP response by W-20-17 cells was 3.9 ng/ml, about seven-fold less than the 29 ng/ml required of BMP-2. These results were consistent with the data obtained in the W-20-17 alkaline phosphatase assays for BMP-2 and BMP-2/7.

Figure 11:
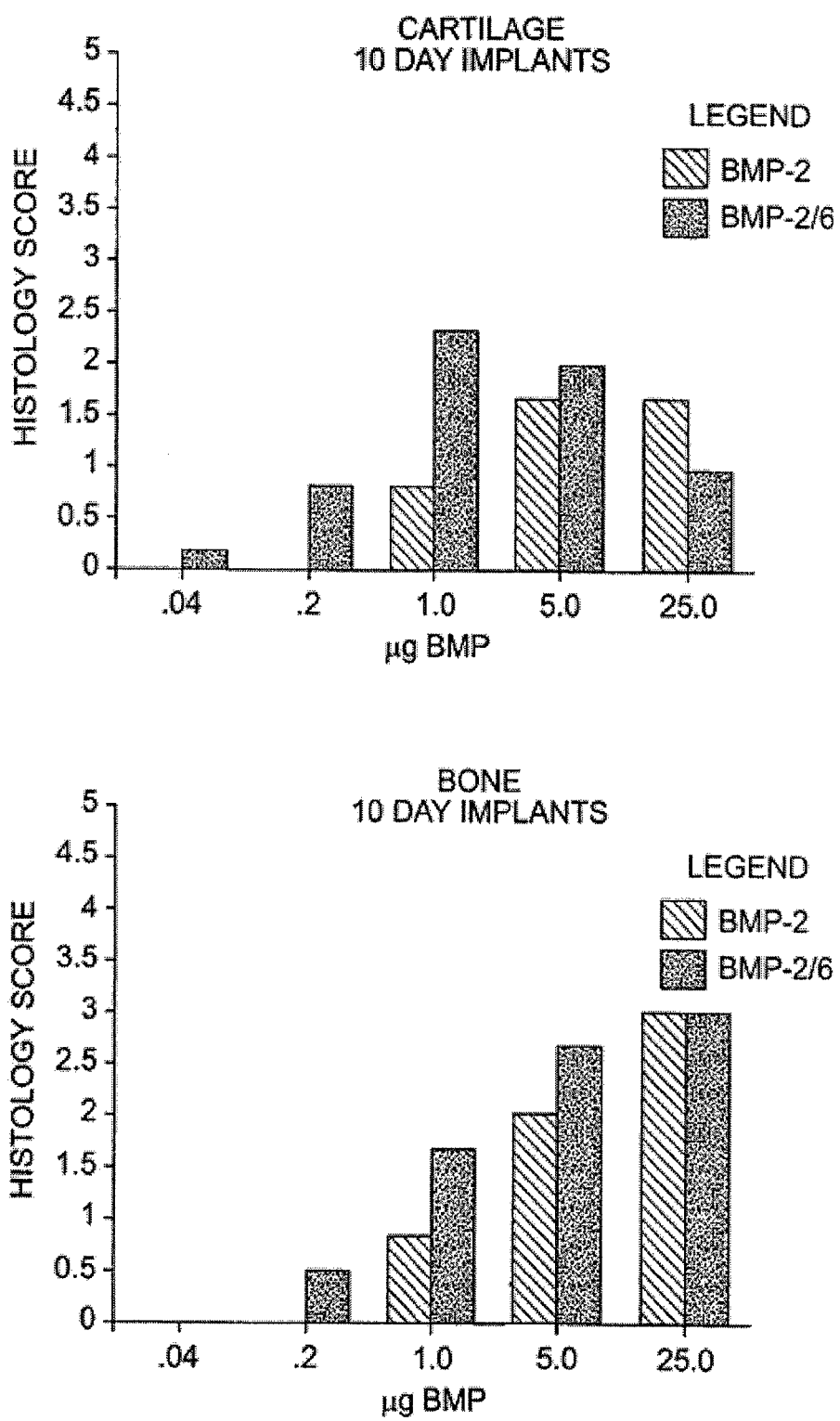
FIG. 11 provides a comparison of the in vivo activity of BMP-2/6 and BMP 2.

Preliminary analysis indicates that BMP-2/6 has a specific activity in vitro similar to that of BMP-2/7. The potencies of BMP-2 and BMP-2/6 on induction of alkaline phosphatase production in W-20 is compared, as shown in FIG. 11, BMP-2/6 has a higher specific activity than BMP-2 in this assay system. This data is in good agreement with data obtained from the in vivo assay of BMP-2 and BMP-2/6).

B. In Vivo Assay (i) BMP-2/7

The purified BMP-2/7 and BMP-2 were tested in the rat ectopic bone formation assay. A series of different amounts of BMP-2/7 or BMP-2 were implanted in triplicate in rats. After 5 and 10 days, the implants were removed and examined histologically for the presence of bone and cartilage. The histological scores for the amounts of new cartilage and bone formed are summarized in Table A.

TABLE A

| | | 5 Day Implants | | 10 Day Implants | |
|---|---|---|---|---|---|
| | | BMP-2/7 | BMP-2 | BMP-2/7 | BMP-2 |
| 0.04 | C | ± – ± | – – – | ± – ± | – – – |
| | B | – – – | – – – | ± – ± | – – – |
| 0.02 | C | ± 1 ± | – – – | 2 1 2 | – ± ± |
| | B | – – – | – – – | 1 ± 1 | – ± – |
| 1.0 | C | 1 ± ± | ± ± ± | 2 2 2 | 1 1 ± |
| | B | – – – | – – – | 2 3 3 | 1 1 ± |
| 5.0 | C | 2 2 1 | 1 ± 1 | 1 1 2 | 1 2 1 |
| | B | ± – 1 | – – – | 4 4 3 | 2 3 2 |
| 25.0 | C | | | ± ± 2 | 2 2 2 |
| | B | | | 4 4 3 | 3 3 3 |

The amount of BMP-2/7 required to induce cartilage and bone in the rat ectopic assay is lower than that of BMP-2. Histologically, the appearance of cartilage and bone induced by BMP-2/7 and BMP-2 are identical.

(ii) BMP-2/6

The in vivo activity of BMP-2/6 was compared with that of BMP-2 by implantation of various amounts of each BMP for ten days in the rat ectopic bone formation assay. The results of this study (Table B, FIG. 12) indicate that BMP-2/6, similar to BMP-2/7, has increased in vivo activity relative to BMP-2. The specific activities of BMP-2, BMP-6, and BMP-2/6 are compared in the ectopic bone formation assay ten days after the proteins are implanted. The results of these experiments are shown in Table C and FIG. 13. BMP-2/6 is a more potent inducer of bone formation than either BMP-2 or BMP-6. The amount of bone formation observed with BMP-2/6 was comparable to that observed with equivalent doses of BMP-2/7. The appearance of BMP-2/6 implants is quite similar to implants containing BMP-2 or BMP-2/7.

TABLE B

Histological scores of Implants of BMP 2/6 and BMP-2 In rat ectopic assay (10 day implants).

| BMP (µg) | C/B | BMP-2/6 | BMP-2 |
|---|---|---|---|
| 0.04 | C | – ± – | – – – |
| | B | – – – | – – – |
| 0.20 | C | 1 1 ± | – – – |
| | B | ± ± ± | – – – |
| 1.0 | C | 1 3 3 | 1 1 ± |
| | B | 1 2 2 | 1 1 ± |
| 5.0 | C | 2 2 2 | 1 2 2 |
| | B | 2 3 3 | 2 2 2 |

TABLE B-continued

Histological scores of Implants of BMP 2/6 and BMP-2 In rat ectopic assay (10 day implants).

| BMP (μg) | C/B | BMP-2/6 | BMP-2 |
|---|---|---|---|
| 25. | C | 1 1 1 | 2 2 1 |
|  | B | 3 3 3 | 3 3 3 |

TABLE C

Histological scores of implants of BMP-2, BMP-6, and BMP-2/6 in rat ectopic assay (10 day implants).

| BMP (μg) | C/B | BMP-2 | BMP-6 | BMP-2/6 |
|---|---|---|---|---|
| 0.04 | C | - - - | - - - | - - ± |
|  | B | - - - | - - - | - - ± |
| 0.20 | C | - - 2 | - - - | 1 2 2 |
|  | B | - - 1 | - - - | 2 2 2 |
| 1.0 | C | - ± ± | 2 1 1 | 1 1 1 |
|  | B | - ± ± | 1 ± ± | 3 3 2 |
| 5.0 | C | 2 2 1 | 3 1 3 | ± ± 1 |
|  | B | 1 1 1 | 2 ± 1 | 4 5 4 |
| 25. | C | ± ± ± | ± ± ± | ± ± ± |
|  | B | 5 4 5 | 4 4 5 | 4 5 3 |

Example 7

Expression of BMP Dimer in E. Coli

A biologically active, homodimeric BMP-2 was expressed in E. coli using the techniques described in European Patent Application 433,255 with minor modifications. Other methods disclosed in the above-referenced European patent application may also be employed to produce heterodimers of the present invention from E. coli. Application of these methods to the heterodimers of this invention is anticipated to produce active BMP heterodimeric proteins from E. coli.

A. BMP-2 Expression Vector

An expression plasmid pALBP2-181 (SEQ ID NO: 13) was constructed containing the mature portion of the BMP-2 (SEQ ID NO: 14) gene and other sequences which are described in detail below. This plasmid directed the accumulation of 5-10% of the total cell protein as BMP-2, in an E. coli host strain, GI724, described below.

Plasmid pALBP2-781 contains the following principal features. Nucleotides 1-2060 contain DNA sequences originating from the plasmid pUC-18 [Norrander et al, *Gene*, 26:101-106 (1983)] including sequences containing the gene for β-lactamase which confers resistance to the antibiotic ampicillin in host E. coli strains, and a colE1-derived origin of replication. Nucleotides 2061-2221 contain DNA sequences for the major leftward promoter (pL) of bacteriophage λ [Sanger et al, *J. Mol. Biol.*, 162:729-773 (1982)], including three operator sequences, $O_L1$, $O_L2$ and $O_L3$ The operators are the binding sites for λcI repressor protein, intracellular levels of which control the amount of transcription initiation from pL. Nucleotides 2222-2723 contain a strong ribosome binding sequence included on a sequence derived from nucleotides 35566 to 35472 and 38137 to 38361 from bacteriophage lambda as described in Sanger et al, *J. Mol. Biol.*, 162: 729-773 (1982). Nucleotides 2724-3133 contain a DNA sequence encoding mature BMP-2 protein with an additional 62 nucleotides of 3'-untranslated sequence.

Nucleotides 3134-3149 provide a "Linker" DNA sequence containing restriction endonuclease sites. Nucleotides 3150-3218 provide a transcription termination sequence based on that of the E. coli aspA gene [Takagi et al, *Nucl. Acids Res.*, 13:2063-2074 (1985)]. Nucleotides 3219-3623 are DNA sequences derived from pUC-18.

As described below, when cultured under the appropriate conditions in a suitable E. coli host strain, pALBP2-781 can direct the production of high levels (approximately 10% of the total cellular protein) of BMP-2 protein.

pALBP2-781 was transformed into the E. coli host strain GI724 (F, $lacI^q$, $lacP^{L8}$, ampC::λcI$^+$) by the procedure of Dagert and Ehrlich, *Gene*, 6:23 (1979). [The untransformed host strain E. coli GI724 was deposited with the American Type Culture Collection, 12301 Parklawn Drive, Rockville, Md. on Jan. 31, 1991 under ATCC No. 55151 for patent purposes pursuant to applicable laws and regulations.] Transformants were selected on 1.5% w/v agar plates containing IMC medium, which is composed of M9 medium [Miller, "Experiments in Molecular Genetics", Cold Spring Harbor Laboratory, New York (1972)] supplemented with 0.5% w/v glucose, 0.2% w/v casamino acids and 100 μg/ml ampicillin.

GI724 contains a copy of the wild-type λcI repressor gene stably integrated into the chromosome at the ampC locus, where it has been placed under the transcriptional control of *Salmonella typhimurium* trp promoter/operator sequences. In GI724, λcI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

GI724 transformed with pALBP2-781 was grown at 37° C. to an $A_{550}$ of 0.5 (Absorbence at 550 nm) in IMC medium. Tryptophan was added to a final concentration of 100 μg/ml and the culture incubated for a further 4 hours. During this time BMP-2 protein accumulated to approximately 10% of the total cell protein, all in the "inclusion body" fraction.

BMP-2 is recovered in a non-soluble, monomeric form as follows. Cell disruption and recovery is performed at 4° C. Approximately 9 g of the wet fermented E. coli GI724/pALBP2-781 cells are suspended in 30 mL of 0.1 M Tris/HCl, 10 mM EDTA, 1 mM phenyl methyl sulphonyl fluoride (PMSF), pH 8.3 (disruption buffer). The cells are passed four times through a cell disrupter and the volume is brought to 100 mL with the disruption buffer. The suspension is centrifuged for 20 min. (15,000×g). The pellet obtained is suspended in 50 mL disruption buffer containing 1 M NaCl and centrifuged for 10 min. as above. The pellet is suspended in 50 mL disruption buffer containing 1% Triton X-100 (Pierce) and again centrifuged for 10 min. as above. The washed pellet is then suspended in 25 mL of 20 mM Tris/HCl, 1 mM EDTA, 1 mM PMSF, 1% DTT, pH 8.3 and homogenized in a glass homogenizer. The resulting suspension contains crude monomeric BMP-2 in a non-soluble form.

Ten mL of the BMP-2 suspension, obtained as described above, are acidified with 10% acetic acid to pH 2.5 and centrifuged in an Eppendorf centrifuge for 10 min. at room temperature. The supernatant is chromatographed. Chromatography was performed on a Sephacryl S-100 HR column (Pharmacia, 2.6×83 cm) in 1% acetic acid at a flow rate of 1.4 mL/minute. Fractions containing monomeric, BMP-2 are pooled. This material is used to generate biologically active, homodimer BMP-2.

Biologically active, homodimeric BMP-2 can be generated from the monomeric BMP-2 obtained following solubilization and purification, described above, as follows.

0.1, 0.5 or 2.5 mg of the BMP-2 is dissolved at a concentration of 20, 100 or 500 μg/mL, respectively, in 50 mM Tris/HCl, pH 8.0, 1 M NaCl, 5 mM EDTA, 2 mM reduced glutathione, 1 mM oxidized glutathione and 33 mM CHAPS [Calbiochem]. After 4 days at 4° C. or 23° C., the mixture is diluted 5 to 10 fold with 0.1% TFA.

Purification of biologically active BMP-2 is achieved by subjecting the diluted mixture to reverse phase HPLC on a a Vydac C4 214TP54 column (25×0.46 cm) [The NEST Group, USA] at a flow rate of 1 ml/minute. Buffer A is 0.1% TFA. Buffer B is 90% acetonitrile, and 0.1% TFA. The linear gradient was 0 to 5 minutes at 20% Buffer B; 5 to 10 minutes at 20 to 30% Buffer B; 10 to 40 minutes at 30 to 60% Buffer B; and 40 to 50 minutes at 60 to 100% Buffer B. Homodimeric BMP-2 is eluted and collected from the HPLC column.

The HPLC fractions are lyophilized to dryness, redissolved in sample buffer (1.5 M Tris-HCl, pH 8.45, 12% glycerol, 4% SDS, 0.0075% Serva Blue G, 0.0025% Phenol Red, with or without 100 mM dithiothreitol) and heated for five minutes at 95° C. The running buffer is 1001 mM Tris, 100 mM tricine (16% tricine gel) [Novex], 0.1% SDS at pH 8.3. The SDS-PAGE gel is run at 125 volts for 2.5 hours.

The gel is stained for one hour with 200 ml of 0.5% Coomassie Brilliant Blue R-250, 25% isopropanol, 10% acetic acid, heated to 60° C. The gel is then destained with 10% acetic acid, 10% isopropanol until the background is clear.

```
-continued
CGAGACCTGG GCTGGCAGGA CTGGATCATC GCGCCTGAAG

GCTACGCCGC CTACTACTGT GAGGGGGAGT GTGCCTTCCC

TCTGAACTCC TACATGAACG CCACCAACCA CGCCATCGTG

CAGACGCTGG TCCACTTCAT CAACCCGGAA ACGGTGCCCA

AGCCCTGCTG TGCGCCCACG CAGCTCAATG CCATCTCCGT

CCTCTACTTC GATGACAGCT CCAACGTCAT CCTGAAGAAA

TACAGAAACA TGGTGGTCCG GGCCTGTGGC TGCCACTAGC

TCCTCCGAGA ATTCAGACCC TTTGGGGCCA AGTTTTTCTG

GATCCT
``` and the ribosome binding site found between residues 2707 and 2723 in pALBP2-781 is replaced by a different ribosome binding site, based on that found preceding the T7 phage gene 10, of sequence 5'-CAAGAAGGAGATATACAT-3'. The host strain and growth conditions used for the production of BMP-7 were as described for BMP-2.

C. BMP-3 Expression Vector

For high level expression of BMP-7 a plasmid pALBMP7-981 was constructed. pALBMP7-981 is identical to plasmid pALBP2-781 with two exceptions: the BMP-2 gene (residues 2724-3133 of pALBP2-781) is replaced by the mature portion of the BMP-7 gene, deleted for sequenced encoding the first seven residues of the mature BMP-7 protein sequence:

```
ATGTCTCATAATC GTTCTAAAAC TCCAAAAAAT CAAGAAGCTC TGCGTATGGC    (SEQ ID NO: 32)

CAACGTGGCA GAGAACAGCA GCAGCGACCA GAGGCAGGCC TGTAAGAAGC

ACGAGCTGTA TGTCAGCTTC CGAGACCTGG GCTGGCAGGA CTGGATCATC

GCGCCTGAAG GCTACGCCGC CTACTACTGT GAGGGGGAGT GTGCCTTCCC

TCTGAACTCC TACATGAACG CCACCAACCA CGCCATCGTG CAGACGCTGG

TCCACTTCAT CAACCCGGAA ACGGTGCCCA AGCCCTGCTG TGCGCCCACG

CAGCTCAATG CCATCTCCGT CCTCTACTTC GATGACAGCT CCAACGTCAT

CCTGAAGAAA TACAGAAACA TGGTGGTCCG GGCCTGTGGC TGCCACTAGC

TCCTCCGAGA ATTCAGACCC TTTGGGGCCA AGTTTTTCTG GATCCT
```

The reduced material ran at approximately 13 kD; the non-reduced material ran at approximately 30 kD, which is indicative of the BMP-2 dimer. This material was later active in the W20 assay of Example 8.

B. BMP-7 Expression Vector

For high level expression of BMP-7 a plasmid pALBMP7-981 was constructed. pALBMP7-981 is identical to plasmid pALBP2-781 with two exceptions: the BMP-2 gene (residues 2724-3133 of pALBP2-781) is replaced by the mature portion of the BMP-7 gene, deleted for sequenced encoding the first seven residues of the mature BMP-7 protein sequence:

```
ATGTCTCATAATC GTTCTAAAAC TCCAAAAAAT CAAGAAGCTC

TGCGTATGGC CAACGTGGCA GAGAACAGCA GCAGCGACCA

GAGGCAGGCC TGTAAGAAGC ACGAGCTGTA TGTCAGCTTC
``` and the ribosome binding site found between residues 2707 and 2723 in pALBP2-781 is replaced by a different ribosome binding site, based on that found preceding the T7 phage gene 10, of sequence 5'-CAAGAAGGAGATATACAT-3' (SEQ ID NO: 33). The host strain and growth conditions used for the production of BMP-7 were as described for BMP-2.

C. BMP-3 Expression Vector

For high level expression of BMP-3 a plasmid pAIB3-782 was constructed. This plasmid is identical to plasmid pALBP2-781, except that the BMP-2 gene (residues 2724-3133 of pALBP2-781) is replaced by a gene encoding a form of mature BMP-3. The sequence of this BMP-3 gene is:

```
                                                    (SEQ ID NO: 34)
ATGCGTAAAC AATGGATTGA ACCACGTAAC TGTGCTCGTC

GTTATCTGAA AGTAGACTTT GCAGATATTG GCTGGAGTGA

ATGGATTATC TCCCCCAAGT CCTTTGATGC CTATTATTGC

TCTGGAGCAT GCCAGTTCCC CATGCCAAAG TCTTTGAAGC

CATCAAATCA TGCTACCATC CAGAGTATAG TGAGAGCTGT
```

-continued

```
GGGGGTCGTT CCTGGGATTC CTGAGCCTTG CTGTGTACCA

GAAAAGATGT CCTCACTCAG TATTTTATTC TTTGATGAAA

ATAAGAATGT AGTGCTTAAA GTATACCCTA ACATGACAGT

AGAGTCTTGC GCTTGCAGAT AACCTGGCAA AGAACTCATT

TGAATGCTTA ATTCAAT
```

The host strain and growth conditions used for the production of BMP-3 were as described for BMP-2.

D. Expression of a BMP-2/7 Heterodimer in *E. coli*

Denatured and purified *E. coli* BMP-2 and BMP-7 monomers were isolated from *E. coli* inclusion body pellets by acidification and gel filtration as previously as previously described above. 125 ug of each BMP in 1% acetic acid were mixed and taken to dryness in a speed vac. The material was resuspended in 2.5 ml 50 mM Tris, 1.0 NaCl, 5 mM EDTA, 33 mM CHAPS, 2 mM glutathione (reduced), 1 mM glutathione (oxidized), pH 8.0. The sample was incubated at 23 C for one week.

The BMP-2/7 heterodimer was isolated by HPLC on a 25.times.0.46 cm Vydac C4 column. The sample was centrifuged in a microfuge for 5 minutes, and the supernatant was diluted with 22.5 ml 0.1% TFA.

| A buffer | 0.1% TFA |
|---|---|
| B buffer | 0.1% TFA, 95% acetonitrile, 1.0 ml/minute |
| 0-5' | 20% B |
| 5-10' | 20-30% B |
| 10-90' | 30-50% B |
| 90-100' | 50-100% B |

Figure 9:
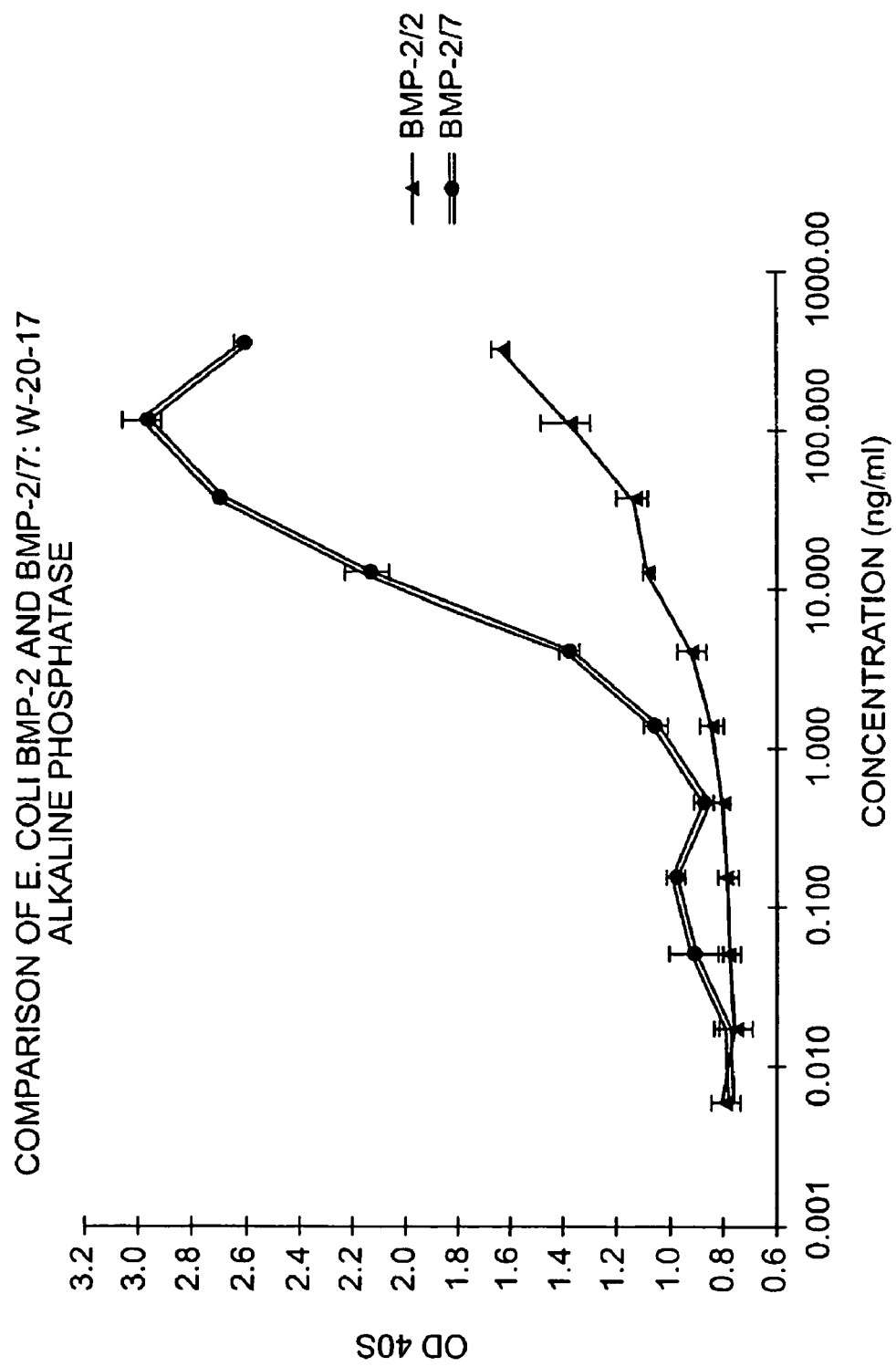
FIG. 9 provides a comparison of the W-20 activity of E. coli produced BMP-2 and BMP-2/7 heterodimer.
Figure 10:
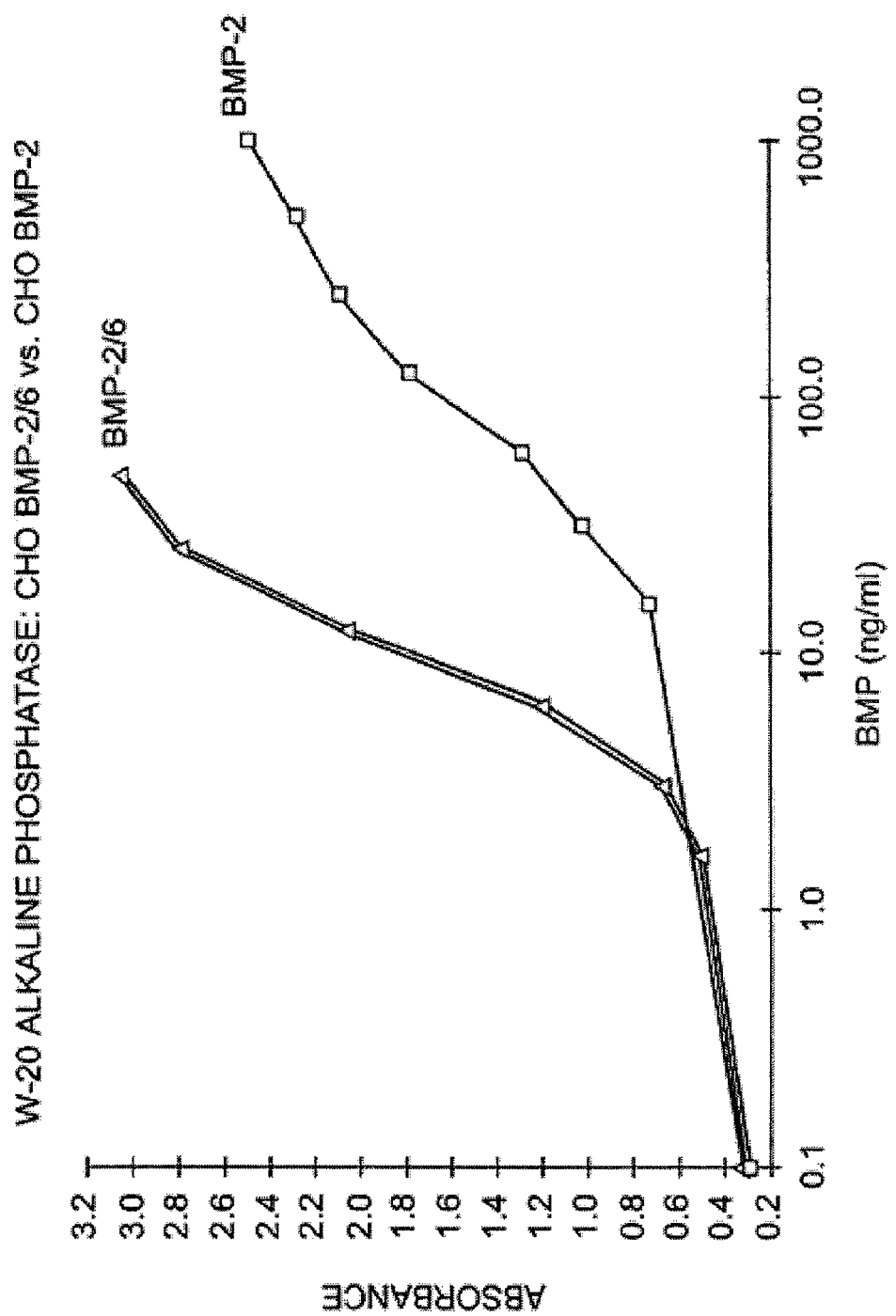
FIG. 10 provides a comparison of BMP-2 and BMP-2/6 in the W-20 assay.

By SDS-PAGE analysis, the BMP-2/7 heterodimer eluted at about 23'. FIG. 9 is a comparison of the W-20 activity of *E. coli* BMP-2 and BMP-2/7 heterodimer, indicating greater activity of the heterodimer.

F. Expression of BMP-2/3 Heterodimer in *E. coli*

BMP-2 and BMP-3 monomers were isolated as follows: to 1.0 g of frozen harvested cells expressing either BMP-2 or BMP-3 was added 3.3 ml of 100 mM Tris, 10 mM EDTA, pH 8.3. The cells were resuspended by vortexing vigorously. 33 ul of 100 mM PMSF in isopropanol was added and the cells lysed by one pass through a French pressure cell. The lysate was centrifuged in a microfuge for 20 minutes at 4 C. The supernatant was discarded. The inclusion body pellet was taken up in 8.0 M quanidine hydrochloride, 0.25 M OTT, 0.5 M Tris, 5 mM EDTA, pH 8.5, and heated at 37 C for one hour.

The reduced and denatured BMP monomers were isolated by HPLC on a Supelco C4 guard column as follows:

| A buffer | 0.1% TFA |
|---|---|
| B buffer | 0.1% TFA, 95% acetonitrile 1.0 ml/minute |
| 0-5' | 1% B |
| 5-40' | 1-70% B |
| 40-45' | 70-100% B |

Monomeric BMP eluted at 28-30'. Protein concentration was estimated by A280 and the appropriate extinction coefficient.

10 ug of BMP-2 and BMP-3 were combined and taken to dryness in a speed vac. To this was added 50 ul of 50 mM Tris, 1.0 M NaCl, 5 mM EDTA, 33 mM CHAPS, 2 mM reduced glutathione, 1 mM oxidized glutathione, pH 8.5. The sample was incubated at 23 for 3 days. The sample was analyzed by SDS-PAGE on a 16% tricine gel-under reducing and nonreducing conditions. The BMP-2/3 heterodimer migrated at about 35 kd nonreduced, and reduced to BMP-2 monomer at about 13 kd and BMP-3 monomer at about 21 kd.

BMP-2/3 heterodimer produced in *E. coli* is tested for in vivo activity. (20 µg) at (ten days) is utilized to compare the in vivo activity of BMP-2/3 to BMP-2. BMP-2/3 implants showed no cartilage or bone forming activity, while the BMP-2 control implants showed the predicted amounts of bone and cartilage formation. The in vivo data obtained with BMP-2/3 is consistent with the in vitro data from the W-20 assay.

Example 8

W-20 Bioassays

A. Description of W-20 Cells

Use of the W-20 bone marrow stromal cells as an indicator cell line is based upon the conversion of these cells to osteoblast-like cells after treatment with BMP-2 [R. S. Thies et al, "Bone Morphogenetic Protein alters W-20 stromal cell differentiation in vitro", *Journal of Bone and Mineral Research*, 5(2):305 (1990); and R. S. Thies et al, "Recombinant Human Bone Morphogenetic Protein 2 Induces Osteoblastic Differentiation in W-20-17 Stromal Cells", *Endocrinology*, in press (1992)]. Specifically, W-20 cells are a clonal bone marrow stromal cell line derived from adult mice by researchers in the laboratory of Dr. D. Nathan, Children's Hospital, Boston, Mass. BMP-2 treatment of W-20 cells results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 µl of media (DME with 10% heat inactivated fetal calf serum, 2 mM glutamine and 100 U/ml+100 µg/ml streptomycin. The cells are allowed to attach overnight in a 95% air, 5% $CO_2$ incubator at 37° C.

The 200 µl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 µl per well of calcium/magnesium free phosphate buffered saline and these washes are discarded.

50 µl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 μl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 μl of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE 1

| Absorbance Values for Known Standards of P-Nitrophenol Phosphate | |
|---|---|
| P-nitrophenol phosphate umoles | Mean absorbance (405 nm) |
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMP-2 can be determined and converted to μmoles of p-nitrophenol phosphate cleaved per unit time as shown in Table II.

TABLE II

| Alkaline Phosphatase Values for W-20 Cells Treating with BMP-2 | | |
|---|---|---|
| BMP-2 concentration ng/ml | Absorbance Reading 405 nmeters | umoles substrate per hour |
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP heterodimers to BMP-2 homodimer.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At the end of 96 hours, 50 μl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

| Osteocalcin Synthesis by W-20 Cells | |
|---|---|
| BMP-2 Concentration ng/ml | Osteocalcin Synthesis ng/well |
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

Example 9

Rosen Modified Sampath-Reddi Assay

A modified version of the rat bone formation assay described in Sampath and Reddi, *Proc. Natl. Acad. Sci. USA*, 80:6591-6595 (1983) is used to evaluate bone and/or cartilage activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21-49 ay old male Long Evans rats. The implants are removed after 7-14 days. Half of each implant is used for alkaline phosphatase analysis [see, A. H. Reddi et al, *Proc. Natl. Acad. Sci.*, 69:1601 (1972)].

The other half of each implant is fixed and processed for histological analysis. 1 μm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

The heterodimeric BMP proteins of this invention may be assessed for activity on this assay.

Numerous modifications and variations in practice of this invention are expected to occur to those skilled in the art. Such modifications and variations are encompassed within the following claims.

What is claimed is:

1. An isolated recombinant dimeric protein having bone stimulating activity comprising a first bone morphogenetic protein-2 (BMP-2) subunit in association with a second BMP-2 subunit, wherein each subunit consists of an amino acid sequence selected from the group consisting of
    (a) amino acids 249-396 of SEQ ID NO:2;
    (b) amino acids 266-396 of SEQ ID NO:2;
    (c) amino acids 283-396 of SEQ ID NO:2; and
    (d) amino acids 296-396 of SEQ ID NO:2,
and wherein the first subunit and the second subunit do not have the same amino acid sequence.

2. A method for producing the dimeric protein of claim 1 comprising (a) co-expressing the first and second subunits of bone morphogenetic protein-2 in a selected host cell; and (b) isolating the dimeric protein from the culture medium.

* * * * *